(12) United States Patent
Quake et al.

(10) Patent No.: US 7,297,518 B2
(45) Date of Patent: *Nov. 20, 2007

(54) METHODS AND APPARATUS FOR ANALYZING POLYNUCLEOTIDE SEQUENCES BY ASYNCHRONOUS BASE EXTENSION

(75) Inventors: Stephen Quake, San Marino, CA (US); Ido Braslavsky, Pasadena, CA (US); Benedict Hebert, Pasadena, CA (US); Emil Kartalov, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 10/099,459

(22) Filed: Mar. 12, 2002

(65) Prior Publication Data

US 2002/0164629 A1    Nov. 7, 2002

Related U.S. Application Data

(60) Provisional application No. 60/275,232, filed on Mar. 12, 2001.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .................. 435/91.2; 435/6; 435/91.1; 536/23.1; 536/24.3; 536/24.33; 536/25.3

(58) Field of Classification Search .................. 435/6, 435/91.1, 183, 287.1, 287.2, 288.4, 288.7; 536/23.1, 24.3, 24.33, 25.3, 25.32
See application file for complete search history.

(56) References Cited

U.S. PATENT DOCUMENTS

| | | |
|---|---|---|
| 3,996,345 A | 12/1976 | Ullman et al. |
| 4,119,368 A | 10/1978 | Yamakazi |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Koster et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki |
| 5,198,540 A | 3/1993 | Koster |
| 5,209,834 A | 5/1993 | Shera |
| 5,224,843 A | 7/1993 | Van Lintel |
| 5,242,797 A | 9/1993 | Hirschfeld |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |

(Continued)

FOREIGN PATENT DOCUMENTS

EP    0 579 997 A1    1/1994

(Continued)

OTHER PUBLICATIONS

Adam, David "Individual genomes targeted in sequencing revolution", Nature. 2001, p. 402, vol. 411.

Ambrose, W.P. et al, "Single-Molecule Detection With Total Internal Reflection Excitation: Comparing Signal-to-Background and Total Signals in Different Geometries" Cytometry, 1999, p. 224-231, vol. 36.

Arndt-Jovin et al. "Immunofluorescence Localization of Z-DNA in Chromosomes: Quantitation by Scanning Microphotometry and Computer-assisted Image Analysis" Journal of Cell Biology, Oct. 1985, pp. 1422-1433, vol. 101.

(Continued)

*Primary Examiner*—Frank W. Lu
(74) *Attorney, Agent, or Firm*—Proskauer Rose LLP

(57) ABSTRACT

The invention provides methods and apparatus for analyzing polynucleotide sequences by asynchronous base extension. Some applications of the invention utilize total internal reflection fluorescence microscopy to image polynucleotide molecules at single molecule resolution.

24 Claims, 15 Drawing Sheets

U.S. PATENT DOCUMENTS

| | | | |
|---|---|---|---|
| 5,376,252 A | 12/1994 | Ekstrom | |
| 5,403,709 A | 4/1995 | Agrawal et al. | |
| 5,405,747 A | 4/1995 | Jett et al. | |
| 5,405,783 A | 4/1995 | Pirrung et al. | |
| 5,409,811 A | 4/1995 | Tabor et al. | |
| 5,424,186 A | 6/1995 | Fodor et al. | |
| 5,449,767 A | 9/1995 | Ward et al. | |
| 5,476,928 A | 12/1995 | Ward et al. | |
| 5,484,701 A | 1/1996 | Cocuzza et al. | |
| 5,492,806 A | 2/1996 | Drmanac et al. | |
| 5,514,256 A | 5/1996 | Douthart et al. | |
| 5,518,900 A | 5/1996 | Nikiforov et al. | |
| 5,525,464 A | 6/1996 | Drmanac et al. | |
| 5,529,465 A | 6/1996 | Zengerle et al. | |
| 5,534,125 A | 7/1996 | Middendorf et al. | |
| 5,547,839 A | 8/1996 | Dower et al. | |
| 5,556,790 A | 9/1996 | Pettit | |
| 5,558,991 A | 9/1996 | Trainor | |
| 5,599,695 A | 2/1997 | Pease et al. | |
| 5,610,287 A | 3/1997 | Nikiforov et al. | |
| 5,631,734 A | 5/1997 | Stern et al. | |
| 5,632,957 A | 5/1997 | Heller et al. | |
| 5,654,149 A | 8/1997 | Mendoza et al. | |
| 5,659,171 A | 8/1997 | Young et al. | |
| 5,670,346 A | 9/1997 | Reeve et al. | |
| 5,674,716 A | 10/1997 | Tabor et al. | |
| 5,675,155 A | 10/1997 | Pentoney, Jr. et al. | |
| 5,688,648 A | 11/1997 | Mathies et al. | |
| 5,695,940 A | 12/1997 | Drmanac et al. | |
| 5,705,018 A | 1/1998 | Hartley | |
| 5,707,506 A | 1/1998 | Douthart et al. | |
| 5,710,628 A | 1/1998 | Waterhouse et al. | |
| 5,712,476 A | 1/1998 | Renfrew et al. | |
| 5,733,729 A | 3/1998 | Lipshutz et al. | |
| 5,741,640 A | 4/1998 | Fuller | |
| 5,741,644 A | 4/1998 | Kambara et al. | |
| 5,744,305 A | 4/1998 | Fodor et al. | |
| 5,744,312 A | 4/1998 | Mamone et al. | |
| 5,750,341 A | 5/1998 | Macevicz et al. | |
| 5,753,788 A | 5/1998 | Fodor et al. | |
| 5,755,943 A | 5/1998 | Middendorf et al. | |
| 5,756,285 A | 5/1998 | Fuller | |
| 5,759,014 A | 6/1998 | Van Lintel | |
| 5,759,374 A | 6/1998 | Takahashi et al. | |
| 5,762,876 A | 6/1998 | Lincoln et al. | |
| 5,776,767 A | 7/1998 | Stevens et al. | |
| 5,776,782 A | 7/1998 | Tsuji | |
| 5,789,168 A | 8/1998 | Leushner et al. | |
| 5,795,722 A | 8/1998 | Lacroix et al. | |
| 5,795,782 A | 8/1998 | Church et al. | |
| 5,807,679 A | 9/1998 | Kamb | |
| 5,830,657 A | 11/1998 | Leushner et al. | |
| 5,831,070 A | 11/1998 | Pease et al. | |
| 5,832,165 A | 11/1998 | Reichert et al. | |
| 5,834,758 A | 11/1998 | Trulson et al. | |
| 5,836,750 A | 11/1998 | Cabuz | |
| 5,837,832 A | 11/1998 | Chee et al. | |
| 5,837,860 A | 11/1998 | Anderson et al. | |
| 5,846,396 A | 12/1998 | Zanzucchi et al. | |
| 5,846,727 A | 12/1998 | Soper et al. | |
| 5,853,979 A | 12/1998 | Green et al. | |
| 5,858,671 A | 1/1999 | Jones | |
| 5,861,287 A | 1/1999 | Metzker et al. | |
| 5,863,722 A | 1/1999 | Brenner | |
| 5,872,244 A | 2/1999 | Hiatt et al. | |
| 5,876,187 A | 3/1999 | Forster et al. | |
| 5,876,934 A | 3/1999 | Duthie et al. | |
| 5,880,473 A * | 3/1999 | Ginestet ............... 250/458.1 | |
| 5,882,904 A | 3/1999 | Riedl et al. | |
| 5,885,813 A | 3/1999 | Davis et al. | |
| 5,889,165 A | 3/1999 | Fodor et al. | |
| 5,902,723 A | 5/1999 | Dower et al. | |
| 5,908,755 A | 6/1999 | Kumar et al. | |
| 5,916,747 A | 6/1999 | Gilchrist et al. | |
| 5,922,591 A | 7/1999 | Anderson et al. | |
| 5,922,608 A | 7/1999 | Farnsworth et al. | |
| 5,928,906 A * | 7/1999 | Koster et al. ............... 435/91.2 |
| 5,928,919 A | 7/1999 | Reha-Krantz et al. | |
| 5,945,283 A | 8/1999 | Kwok et al. | |
| 5,945,284 A | 8/1999 | Livak et al. | |
| 5,945,312 A | 8/1999 | Goodman et al. | |
| 5,945,325 A | 8/1999 | Arnold et al. | |
| 5,948,614 A | 9/1999 | Chatterjee | |
| 5,952,174 A | 9/1999 | Nikiforov et al. | |
| 5,954,932 A | 9/1999 | Takahashi et al. | |
| 5,958,703 A | 9/1999 | Dower et al. | |
| 5,959,781 A | 9/1999 | Kintz et al. | |
| 5,959,837 A | 9/1999 | Yu | |
| 5,965,446 A | 10/1999 | Ishikawa | |
| 5,968,740 A | 10/1999 | Fodor et al. | |
| 5,974,164 A | 10/1999 | Chee | |
| 5,976,338 A | 11/1999 | Fujita et al. | |
| 5,981,186 A | 11/1999 | Gabe et al. | |
| 5,981,956 A | 11/1999 | Stern | |
| 5,994,058 A | 11/1999 | Senapathy | |
| 5,994,085 A | 11/1999 | Cantor | |
| 6,002,471 A | 12/1999 | Quake | |
| 6,005,663 A | 12/1999 | Waterhouse et al. | |
| 6,007,309 A | 12/1999 | Hartley | |
| 6,015,714 A | 1/2000 | Baldarelli et al. | |
| 6,017,702 A | 1/2000 | Lee et al. | |
| 6,018,041 A | 1/2000 | Drmanac et al. | |
| 6,020,457 A | 2/2000 | Klimash et al. | |
| 6,024,925 A | 2/2000 | Little et al. | |
| 6,025,136 A | 2/2000 | Drmanac | |
| 6,028,190 A | 2/2000 | Mathies et al. | |
| 6,030,782 A | 2/2000 | Anderson et al. | |
| 6,043,080 A | 3/2000 | Lipshutz et al. | |
| 6,046,005 A | 4/2000 | Ju et al. | |
| 6,049,380 A | 4/2000 | Goodwin et al. | |
| 6,051,380 A | 4/2000 | Sosnowski et al. | |
| 6,066,454 A | 5/2000 | Lipshutz et al. | |
| 6,071,394 A | 6/2000 | Cheng et al. | |
| 6,077,664 A | 6/2000 | Slater et al. | |
| 6,077,674 A | 6/2000 | Schleifer et al. | |
| 6,087,095 A | 7/2000 | Rosenthal et al. | |
| 6,087,099 A | 7/2000 | Gupte et al. | |
| 6,094,274 A | 7/2000 | Yokoi | |
| 6,107,032 A | 8/2000 | Kilger et al. | |
| 6,107,044 A | 8/2000 | Nikiforov | |
| 6,132,580 A | 10/2000 | Mathies et al. | |
| 6,133,436 A | 10/2000 | Koster et al. | |
| 6,136,212 A | 10/2000 | Mastrangelo et al. | |
| 6,136,962 A | 10/2000 | Shi et al. | |
| 6,140,053 A | 10/2000 | Koster | |
| 6,140,494 A | 10/2000 | Hamilton et al. | |
| 6,141,096 A | 10/2000 | Stern et al. | |
| 6,143,151 A | 11/2000 | Middendorf et al. | |
| 6,147,205 A | 11/2000 | McGall et al. | |
| 6,156,501 A | 12/2000 | McGall et al. | |
| 6,165,694 A | 12/2000 | Liu | |
| 6,177,249 B1 | 1/2001 | Kwok et al. | |
| 6,197,506 B1 | 3/2001 | Fodor et al. | |
| 6,197,595 B1 | 3/2001 | Anderson et al. | |
| 6,207,381 B1 | 3/2001 | Larsson et al. | |
| 6,207,960 B1 | 3/2001 | Stern | |
| 6,210,896 B1 | 4/2001 | Chan | |
| 6,214,246 B1 | 4/2001 | Craighead | |
| 6,221,592 B1 | 4/2001 | Schwartz et al. | |
| 6,221,654 B1 | 4/2001 | Quake et al. | |
| 6,225,052 B1 | 5/2001 | Batz et al. | |
| 6,225,062 B1 | 5/2001 | Dunn et al. | |
| 6,225,092 B1 | 5/2001 | Kilger et al. | |
| 6,225,109 B1 | 5/2001 | Juncosa et al. | |

| | | | | | | |
|---|---|---|---|---|---|---|
| 6,225,567 B1 | 5/2001 | Kester | | 6,416,952 B1 | 7/2002 | Pirrung et al. |
| 6,225,625 B1 | 5/2001 | Pirrung et al. | | 6,420,169 B1 | 7/2002 | Read et al. |
| 6,228,593 B1 | 5/2001 | Lipshutz et al. | | 6,423,273 B1 | 7/2002 | O'Mara |
| 6,232,075 B1 | 5/2001 | Williams | | 6,432,634 B1 | 8/2002 | Digby et al. |
| 6,232,103 B1 | 5/2001 | Short | | 6,436,641 B1 | 8/2002 | Izmailov |
| 6,235,473 B1 | 5/2001 | Friedman et al. | | 6,436,646 B1 | 8/2002 | Nikiforov |
| 6,242,180 B1 | 6/2001 | Chee | | 6,440,664 B1 | 8/2002 | Digby et al. |
| 6,242,528 B1 | 6/2001 | Clark et al. | | 6,440,722 B1 | 8/2002 | Knapp et al. |
| 6,245,506 B1 | 6/2001 | Laugharn, Jr. et al. | | 6,444,106 B1 | 9/2002 | Mcbride et al. |
| 6,245,507 B1 | 6/2001 | Bogdanov | | 6,444,173 B1 | 9/2002 | Sjursen et al. |
| 6,245,518 B1 | 6/2001 | Baier | | 6,444,424 B1 | 9/2002 | Chatterjee et al. |
| 6,251,610 B1 | 6/2001 | Gupte et al. | | 6,444,461 B1 | 9/2002 | Knapp et al. |
| 6,255,083 B1 | 7/2001 | Williams | | 6,447,724 B1 | 9/2002 | Jensen et al. |
| 6,255,475 B1 | 7/2001 | Kwiatkowski | | 6,448,090 B1 | 9/2002 | McBride |
| 6,258,533 B1 | 7/2001 | Jones | | 6,451,536 B1 | 9/2002 | Fodor et al. |
| 6,261,775 B1 * | 7/2001 | Bastian et al. ............... 435/6 | | 6,479,267 B1 | 11/2002 | Davis et al. |
| 6,261,776 B1 | 7/2001 | Pirrung et al. | | 6,485,690 B1 | 11/2002 | Pfost et al. |
| 6,261,848 B1 | 7/2001 | Anderson et al. | | 6,485,909 B1 | 11/2002 | Hong et al. |
| 6,262,838 B1 | 7/2001 | Montagu | | 6,485,944 B1 | 11/2002 | Church et al. |
| 6,263,286 B1 | 7/2001 | Gilmanshin et al. | | 6,495,363 B2 | 12/2002 | Bogdanov |
| 6,268,152 B1 | 7/2001 | Fodor et al. | | 6,506,560 B1 | 1/2003 | Hughes et al. |
| 6,268,219 B1 | 7/2001 | Mcbride et al. | | 6,511,803 B1 | 1/2003 | Church et al. |
| 6,269,846 B1 | 8/2001 | Overbeck et al. | | 6,514,706 B1 | 2/2003 | Von Kalle et al. |
| 6,270,644 B1 | 8/2001 | Mathies et al. | | 6,521,428 B1 | 2/2003 | Senapathy |
| 6,270,961 B1 | 8/2001 | Drmanac | | 6,524,829 B1 | 2/2003 | Seeger |
| 6,274,320 B1 | 8/2001 | Rothberg et al. | | 6,528,258 B1 | 3/2003 | Russell |
| 6,274,351 B1 | 8/2001 | Peponnet | | 6,528,288 B2 | 3/2003 | Senapathy |
| 6,277,604 B1 | 8/2001 | Peponnet | | 6,537,755 B1 | 3/2003 | Drmanac |
| 6,280,954 B1 | 8/2001 | Ulfendahl | | 6,537,757 B1 | 3/2003 | Langmore et al. |
| 6,284,460 B1 | 9/2001 | Fodor et al. | | 6,546,340 B2 | 4/2003 | Lipshutz et al. |
| 6,287,821 B1 | 9/2001 | Shi et al. | | 6,551,784 B2 | 4/2003 | Fodor et al. |
| 6,294,336 B1 | 9/2001 | Boyce-Jacino et al. | | 6,551,817 B2 | 4/2003 | Besemer et al. |
| 6,294,337 B1 | 9/2001 | Hayashizaki | | 6,554,987 B1 | 4/2003 | Gilchrist et al. |
| 6,306,607 B2 | 10/2001 | Williams | | 6,555,349 B1 | 4/2003 | O'Donnell |
| 6,309,601 B1 | 10/2001 | Juncosa et al. | | 6,558,945 B1 | 5/2003 | Kao |
| 6,309,701 B1 | 10/2001 | Barbera-Guillem | | 6,562,566 B1 | 5/2003 | Hoheisel |
| 6,309,824 B1 | 10/2001 | Drmanac | | 6,566,059 B1 | 5/2003 | Stanton, Jr. et al. |
| 6,309,836 B1 | 10/2001 | Kwiatowski | | 6,566,515 B1 | 5/2003 | McGall et al. |
| 6,309,886 B1 | 10/2001 | Ambrose et al. | | 6,573,047 B1 | 6/2003 | Hung et al. |
| 6,310,189 B1 | 10/2001 | Fodor et al. | | 6,573,374 B1 | 6/2003 | Muehlegger et al. |
| 6,312,893 B1 | 11/2001 | Van Ness et al. | | 6,576,424 B2 | 6/2003 | Fodor et al. |
| 6,316,191 B1 | 11/2001 | Drmanac et al. | | 6,576,425 B2 | 6/2003 | McGall et al. |
| 6,322,968 B1 | 11/2001 | Head et al. | | 6,579,704 B2 | 6/2003 | Short |
| 6,322,988 B1 * | 11/2001 | Dawson et al. ............... 435/6 | | 6,582,923 B2 | 6/2003 | Stanton, Jr. et al. |
| 6,331,439 B1 | 12/2001 | Cherukuri et al. | | 6,585,939 B1 | 7/2003 | Dapprich |
| 6,333,183 B1 | 12/2001 | Evans et al. | | 6,607,888 B2 | 8/2003 | Schwartz et al. |
| 6,335,824 B1 | 1/2002 | Overbeck | | 6,610,482 B1 | 8/2003 | Fodor et al. |
| 6,337,185 B1 | 1/2002 | Asp et al. | | 6,613,513 B1 | 9/2003 | Parce et al. |
| 6,337,188 B1 | 1/2002 | Head et al. | | 6,623,928 B2 | 9/2003 | Van Ness et al. |
| 6,342,326 B1 | 1/2002 | Milton | | 6,627,748 B1 | 9/2003 | Ju et al. |
| 6,344,325 B1 | 2/2002 | Quake et al. | | 6,642,001 B1 | 11/2003 | Bolk et al. |
| 6,346,379 B1 | 2/2002 | Gelfand et al. | | 6,664,079 B2 | 12/2003 | Ju et al. |
| 6,346,413 B1 | 2/2002 | Fodor et al. | | 6,719,868 B1 | 4/2004 | Schueller et al. |
| 6,355,420 B1 | 3/2002 | Chan | | 6,750,018 B2 | 6/2004 | Kambara et al. |
| 6,355,432 B1 | 3/2002 | Fodor et al. | | 6,783,938 B2 | 8/2004 | Nygren et al. |
| 6,361,671 B1 | 3/2002 | Mathies et al. | | 6,787,308 B2 | 9/2004 | Balasubramanian et al. |
| 6,361,937 B1 | 3/2002 | Stryer | | 6,818,395 B1 * | 11/2004 | Quake et al. ............... 435/6 |
| 6,368,562 B1 | 4/2002 | Yao | | 2001/0024790 A1 | 9/2001 | Kambara et al. |
| 6,368,699 B1 | 4/2002 | Gilbert et al. | | 2001/0044531 A1 | 11/2001 | McGall et al. |
| 6,387,626 B1 | 5/2002 | Shi et al. | | 2001/0046681 A1 | 11/2001 | Senapathy |
| 6,395,232 B1 | 5/2002 | McBride | | 2002/0009744 A1 | 1/2002 | Bogdanov |
| 6,395,559 B1 | 5/2002 | Swenson | | 2002/0012910 A1 | 1/2002 | Weiss et al. |
| 6,397,150 B1 | 5/2002 | Izmailov | | 2002/0015961 A1 | 2/2002 | Kwiatkowski |
| 6,399,364 B1 | 6/2002 | Reeve et al. | | 2002/0025529 A1 * | 2/2002 | Quake et al. ............... 435/6 |
| 6,401,267 B1 | 6/2002 | Drmanac | | 2002/0032320 A1 | 3/2002 | Burgess et al. |
| 6,403,311 B1 | 6/2002 | Chan | | 2002/0034792 A1 | 3/2002 | Kilger et al. |
| 6,403,315 B1 | 6/2002 | Drmanac | | 2002/0039738 A1 | 4/2002 | Williams et al. |
| 6,403,317 B1 | 6/2002 | Anderson | | 2002/0042112 A1 | 4/2002 | Koster et al. |
| 6,403,320 B1 | 6/2002 | Read et al. | | 2002/0045182 A1 | 4/2002 | Singh et al. |
| 6,403,957 B1 | 6/2002 | Fodor et al. | | 2002/0051992 A1 | 5/2002 | Bridgham et al. |
| 6,404,907 B1 | 6/2002 | Gilchrist et al. | | 2002/0053532 A1 | 5/2002 | Quake et al. |
| 6,406,893 B1 | 6/2002 | Knapp et al. | | 2002/0061529 A1 | 5/2002 | Bridgham et al. |
| 6,407,858 B1 | 6/2002 | Montagu | | 2002/0072055 A1 | 6/2002 | Jones |

| | | |
|---|---|---|
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster |
| 2002/0150938 A1 | 10/2002 | Kneipp et al. |
| 2002/0164629 A1 | 11/2002 | Quake et al. |
| 2002/0168642 A1 | 11/2002 | Drukier |
| 2002/0168678 A1 | 11/2002 | Williams et al. |
| 2002/0172948 A1 | 11/2002 | Perlin |
| 2002/0177129 A1 | 11/2002 | Paabo et al. |
| 2002/0182601 A1 | 12/2002 | Sampson et al. |
| 2002/0192661 A1 | 12/2002 | Paabo et al. |
| 2002/0192662 A1 | 12/2002 | Boyce-Jacino et al. |
| 2002/0192691 A1 | 12/2002 | Drmanac |
| 2002/0197618 A1 | 12/2002 | Sampson |
| 2003/0003498 A1 | 1/2003 | Digby et al. |
| 2003/0008285 A1 | 1/2003 | Fischer |
| 2003/0017461 A1 | 1/2003 | Singh et al. |
| 2003/0022207 A1 | 1/2003 | Balasubramanian et al. |
| 2003/0027140 A1 | 2/2003 | Ju et al. |
| 2003/0036080 A1 | 2/2003 | Jensen et al. |
| 2003/0044778 A1 | 3/2003 | Goelet et al. |
| 2003/0044779 A1 | 3/2003 | Goelet et al. |
| 2003/0044781 A1 | 3/2003 | Korlach et al. |
| 2003/0044816 A1 | 3/2003 | Denison et al. |
| 2003/0054181 A1 | 3/2003 | Swerdlow et al. |
| 2003/0054361 A1 | 3/2003 | Heller |
| 2003/0058440 A1 | 3/2003 | Scott et al. |
| 2003/0058799 A1 | 3/2003 | Yamakawa et al. |
| 2003/0059778 A1 | 3/2003 | Berlin et al. |
| 2003/0060431 A1 | 3/2003 | Simmonds et al. |
| 2003/0064366 A1 | 4/2003 | Hardin et al. |
| 2003/0064398 A1 | 4/2003 | Barnes |
| 2003/0064483 A1 | 4/2003 | Shaw et al. |
| 2003/0087237 A1 | 5/2003 | Hong et al. |
| 2003/0087300 A1 | 5/2003 | Knapp et al. |
| 2003/0092005 A1 | 5/2003 | Levene et al. |
| 2003/0092007 A1 | 5/2003 | Gibbs et al. |
| 2003/0096258 A1 | 5/2003 | Fu et al. |
| 2003/0100006 A1 | 5/2003 | Senapathy |
| 2003/0104437 A1 | 6/2003 | Barnes et al. |
| 2003/0104466 A1 | 6/2003 | Knapp et al. |
| 2003/0108867 A1 | 6/2003 | Chee et al. |
| 2003/0138809 A1 | 7/2003 | Williams et al. |
| 2003/0148344 A1 | 8/2003 | Rothberg et al. |
| 2003/0162213 A1 | 8/2003 | Fuller et al. |
| 2003/0186227 A1 | 10/2003 | Balasubramanian et al. |
| 2003/0186255 A1 | 10/2003 | Williams et al. |
| 2003/0190627 A1 | 10/2003 | Zhao et al. |
| 2003/0190647 A1 | 10/2003 | Odera |
| 2003/0190663 A1 | 10/2003 | Yang et al. |
| 2003/0194722 A1 | 10/2003 | Odedra et al. |
| 2003/0194740 A1 | 10/2003 | Williams |
| 2003/0215862 A1* | 11/2003 | Parce et al. .................. 435/6 |
| 2004/0009487 A1 | 1/2004 | Kadushin et al. |
| 2004/0029115 A9 | 2/2004 | Dower et al. |
| 2004/0054162 A1 | 3/2004 | Hanna |
| 2004/0106110 A1 | 6/2004 | Balasubramanian et al. |
| 2004/0126770 A1 | 7/2004 | Kumar et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 845 603 A1 | 6/1998 |
| EP | 0 932 700 B1 | 8/1999 |
| EP | 0 946 752 B1 | 10/1999 |
| EP | 0955085 A2 | 11/1999 |
| EP | 0 999 055 A2 | 5/2000 |
| EP | 0706004 B1 | 8/2003 |
| GB | 2 155 152 A | 9/1985 |
| GB | 2 308 460 A | 6/1997 |
| GB | 2400518 A | 10/2004 |
| WO | WO 90/13666 A1 | 11/1990 |
| WO | 90/15070 A1 | 12/1990 |
| WO | WO 90/15070 A1 | 12/1990 |
| WO | 91/06678 A1 | 5/1991 |
| WO | WO 91/06678 A1 | 5/1991 |
| WO | 92/10092 A1 | 6/1992 |
| WO | 92/10587 A1 | 6/1992 |
| WO | WO 92/10092 A1 | 6/1992 |
| WO | WO 92/10587 A1 | 6/1992 |
| WO | 93/06121 A1 | 4/1993 |
| WO | WO 93/06121 A1 | 4/1993 |
| WO | WO 93/21340 A1 | 10/1993 |
| WO | 95/12608 A1 | 5/1995 |
| WO | WO 95/12608 A1 | 5/1995 |
| WO | WO 95/27080 A2 | 10/1995 |
| WO | 96/04547 A1 | 2/1996 |
| WO | WO 96/04547 A1 | 2/1996 |
| WO | WO 96/12014 A1 | 4/1996 |
| WO | WO 96/12039 A1 | 4/1996 |
| WO | WO 96/27025 A1 | 9/1996 |
| WO | 97/02488 | 1/1997 |
| WO | 97/22076 | 6/1997 |
| WO | 97/23650 | 6/1997 |
| WO | 97/37041 | 10/1997 |
| WO | 97/39150 | 10/1997 |
| WO | 97/40184 | 10/1997 |
| WO | 97/41258 | 11/1997 |
| WO | 97/41259 | 11/1997 |
| WO | 97/42348 | 11/1997 |
| WO | 98/00708 | 1/1998 |
| WO | 98/02575 | 1/1998 |
| WO | WO 98/07069 A1 | 2/1998 |
| WO | WO 98/13523 A1 | 4/1998 |
| WO | 98/08978 | 5/1998 |
| WO | 98/20019 | 5/1998 |
| WO | 98/20020 A2 | 5/1998 |
| WO | 98/20166 | 5/1998 |
| WO | 98/21361 | 5/1998 |
| WO | WO 98/20020 A2 | 5/1998 |
| WO | 98/27228 | 6/1998 |
| WO | WO 98/28440 A1 | 7/1998 |
| WO | 98/33939 A1 | 8/1998 |
| WO | WO 98/33939 A1 | 8/1998 |
| WO | 98/40520 | 9/1998 |
| WO | 98/41650 | 9/1998 |
| WO | 98/41657 A1 | 9/1998 |
| WO | WO 98/41657 A1 | 9/1998 |
| WO | WO 98/44152 A1 | 10/1998 |
| WO | WO 98/45481 A1 | 10/1998 |
| WO | 98/53300 | 11/1998 |
| WO | 98/54669 | 12/1998 |
| WO | 98/55593 | 12/1998 |
| WO | 99/01768 | 1/1999 |
| WO | 99/05221 | 2/1999 |
| WO | 99/06422 | 2/1999 |
| WO | WO 99/05315 A2 | 2/1999 |
| WO | 99/13109 | 3/1999 |

| | | |
|---|---|---|
| WO | 99/13110 | 3/1999 |
| WO | 99/19516 | 4/1999 |
| WO | WO 99/17093 A1 | 4/1999 |
| WO | 99/24797 | 5/1999 |
| WO | 99/27137 A1 | 6/1999 |
| WO | 99/31278 | 6/1999 |
| WO | WO 99/27137 A1 | 6/1999 |
| WO | WO 99/37810 A1 | 7/1999 |
| WO | 99/39001 | 8/1999 |
| WO | 99/40105 A2 | 8/1999 |
| WO | 99/40223 | 8/1999 |
| WO | 99/41410 | 8/1999 |
| WO | WO 99/40105 A2 | 8/1999 |
| WO | 99/44045 | 9/1999 |
| WO | 99/45153 | 9/1999 |
| WO | 99/47539 | 9/1999 |
| WO | 99/47706 | 9/1999 |
| WO | 99/53423 | 10/1999 |
| WO | 99/64437 | 12/1999 |
| WO | 99/64840 | 12/1999 |
| WO | 99/65938 | 12/1999 |
| WO | 99/66076 A1 | 12/1999 |
| WO | WO 99/61888 A2 | 12/1999 |
| WO | WO 99/66076 A1 | 12/1999 |
| WO | WO 99/66313 A1 | 12/1999 |
| WO | 00/06770 A1 | 2/2000 |
| WO | 00/09753 | 2/2000 |
| WO | WO 00/06770 A1 | 2/2000 |
| WO | 00/11223 A1 | 3/2000 |
| WO | 00/17397 | 3/2000 |
| WO | WO 00/11223 A1 | 3/2000 |
| WO | 00/26935 A2 | 5/2000 |
| WO | WO 00/26935 A2 | 5/2000 |
| WO | 00/34523 A1 | 6/2000 |
| WO | 00/37680 A1 | 6/2000 |
| WO | WO 00/34523 A1 | 6/2000 |
| WO | WO 00/37680 A1 | 6/2000 |
| WO | 00/40750 A1 | 7/2000 |
| WO | 00/40758 | 7/2000 |
| WO | 00/43752 | 7/2000 |
| WO | WO 00/40750 A1 | 7/2000 |
| WO | WO 00/43540 A1 | 7/2000 |
| WO | WO 00/50642 A1 | 8/2000 |
| WO | 00/53812 A2 | 9/2000 |
| WO | 00/56937 | 9/2000 |
| WO | WO 00/53805 A1 | 9/2000 |
| WO | WO 00/53812 A2 | 9/2000 |
| WO | 00/58516 A2 | 10/2000 |
| WO | WO 00/58507 A1 | 10/2000 |
| WO | WO 00/58516 A2 | 10/2000 |
| WO | 00/68410 | 11/2000 |
| WO | 00/70073 A1 | 11/2000 |
| WO | 00/71755 | 11/2000 |
| WO | WO 00/70073 A1 | 11/2000 |
| WO | 00/79007 | 12/2000 |
| WO | WO 01/01025 A2 | 1/2001 |
| WO | 01/16375 | 3/2001 |
| WO | 01/25480 | 4/2001 |
| WO | WO 01/23610 A2 | 4/2001 |
| WO | WO 01/24937 A2 | 4/2001 |
| WO | 01/31055 A2 | 5/2001 |
| WO | 01/38574 | 5/2001 |
| WO | 01/48184 A2 | 5/2001 |
| WO | WO 01/31055 A2 | 5/2001 |
| WO | WO 01/32930 A1 | 5/2001 |
| WO | WO 01/42496 A2 | 6/2001 |
| WO | 01/61044 | 8/2001 |
| WO | WO 01/57248 A2 | 8/2001 |
| WO | WO 01/57249 A1 | 8/2001 |
| WO | 01/64838 | 9/2001 |
| WO | 01/75154 | 10/2001 |
| WO | 01/79536 | 10/2001 |
| WO | 01/85991 | 11/2001 |
| WO | 01/92284 | 12/2001 |
| WO | 01/96607 | 12/2001 |
| WO | 02/02584 | 1/2002 |
| WO | 02/02795 | 1/2002 |
| WO | 02/03305 A2 | 1/2002 |
| WO | 02/04680 A2 | 1/2002 |
| WO | WO 02/00343 A2 | 1/2002 |
| WO | WO 02/02813 A2 | 1/2002 |
| WO | WO 02/03305 A2 | 1/2002 |
| WO | WO 02/04680 A2 | 1/2002 |
| WO | 02/20836 | 3/2002 |
| WO | 02/20837 A2 | 3/2002 |
| WO | WO 02/20837 A2 | 3/2002 |
| WO | 02/27032 | 4/2002 |
| WO | WO 02/29106 A2 | 4/2002 |
| WO | WO 02/30486 A2 | 4/2002 |
| WO | 02/35441 A2 | 5/2002 |
| WO | 02/36832 | 5/2002 |
| WO | WO 02/35441 A2 | 5/2002 |
| WO | 02/44414 | 6/2002 |
| WO | WO 02/061126 A2 | 8/2002 |
| WO | WO 02/061127 A2 | 8/2002 |
| WO | 02/072779 A2 | 9/2002 |
| WO | 02/072892 A1 | 9/2002 |
| WO | WO 02/072779 A2 | 9/2002 |
| WO | 02/077694 | 10/2002 |
| WO | 02/079519 | 10/2002 |
| WO | 02/088381 A2 | 11/2002 |
| WO | 02/088382 A2 | 11/2002 |
| WO | WO 02/088381 | 11/2002 |
| WO | WO 02/088382 | 11/2002 |
| WO | 02/097113 | 12/2002 |
| WO | 02/099398 | 12/2002 |
| WO | 03/002767 | 1/2003 |
| WO | WO 03/016565 A2 | 2/2003 |
| WO | 03/020968 A2 | 3/2003 |
| WO | 03/021010 | 3/2003 |
| WO | WO 03/020968 | 3/2003 |
| WO | 03/031947 A2 | 4/2003 |
| WO | WO 03/031947 | 4/2003 |
| WO | 03/044678 | 5/2003 |
| WO | 03/048991 | 6/2003 |
| WO | 03/062897 | 7/2003 |
| WO | 2004/061119 | 7/2004 |
| WO | 2004/074503 | 9/2004 |

OTHER PUBLICATIONS

Axelrod et al. "Total internal reflection fluorescent microscopy", Journal of Microscopy, Jan. 1983, pp. 19-28, vol. 129, Part 1.

Axelrod, Daniel "Cell-Substrate Contacts Illuminated by Total Internal Reflection Fluorescence" Journal of Cell Biology, Apr. 1981, pp. 141-145, vol. 89.

Basché et al. Chapter 2: "Near-field Optical Imaging and Spectroscopy of SIngle Molecules" and Chapter 3;"Single-Molecule Detection in Analytical Chemistry", *Single Molecule Optical Detection, Imaging, and Spectroscopy*, 1997, Published by Weinheim:VCM, Germany.

Braslavsky et al. "Objective-type dark-field illumination for scattering from microbeads", Applied Optics, Nov. 2001, p. 5650-5657, vol. 40, No. 31.

Braslavsky et al.; "Single Molecule Measurements of DNA Polymerase Activity: A Step Towards Single Molecule Sequencing", Biophysics Journal Abstracts Issue, 2002, p. 507A.

Brechtel et al.; "Control of the electroosmotic flow by metal-salt-containing buffers", J Chromatography A, 1995, pp. 97-105, vol. 716.

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Burghardt et al. "Total Interanl Reflection/Fluorescence Photobleaching Recovery Study of Serum Ablumin Adsorption Dynamics" Biophys. Journal, Mar. 1981, pp. 455-468, vol. 33.

Burghardt et al. "Total Internal Reflection Fluorescence Study of Energy Transfer in Surface-Adsorbed and Dissolved Bovine Serum Albumin" Biochemistry, 1983, pp. 979-985, vol. 22.

Chicurel, "Faster, better, cheaper genotyping", Nature, Aug. 2001, p. 580-582, vol. 412, Issue 6847.

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Chou et al.; "A microfabricated device for sizing and sorting DNA molecules", Applied Physical Sciences, Biophysics, Proc. Natl. Acad. Sci., 1999, pp. 11-13, vol. 96, U.S.A.

Close, D. & Anderson, R. "Ultraviolet Photobleaching of Free Radicals Created in γ-Irradiated Amino Acids" Radiation Research, 1973, pp. 349-357, vol. 53.

Cooper, J. & Hagerman, P. "Analysis of Fluorescence Energy Transfer in Duplex and Branched DNA Molecules" Biochemistry, 1990, pp. 9261-9268, vol. 29.

Decher et al.; "Buildup of ultrathin multilayer films by a self-assembly process .3, consecutively alternating adsorption of anionic and cationic polyelectrolytes on charged surfaces", Thin Solid Films, Apr. 1992, pp. 831-835, vol. 210 (1-2).

Delamarche et al.; "Patterned delivery of immunoglobulins to surfaces using microfluidic networks", Science, 1997, pp. 779-781, vol. 276.

Duffy et al.; "Patterning Electroluminescence Materials with Feature Sizes as Small as 5μm Using Elastomeric Membranes as Masks for Dry Lift-Off", Advanced Materials, 1999, pp. 546-552, vol. 11, No. 7.

Duffy et al.; "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al.; "Rapid Prototyping of Microfluidic Systems in Poly(dimethylsiloxane)", Analytical Chemistry, 1998, pp. 4974-4984, vol. 70, No. 23.

Effenhauser et al.: "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrophoresis, 1997, pp. 2203-2213, vol. 18.

Fahrenberg et al.; "A microvalve system fabricated by thermoplastic molding", J Micromech Microeng, 1995, pp. 169-171, vol. 5.

Fu et al.; "A microfabricated fluorescence-activated cell-sorter", Nature Biotechnology, 1999, pp. 1109-1111, vol. 17.

Funatsu et al.; "Imaging of Single Fluorescent Molecules and Individual ATP Turnovers by Single Myosin Molecules in Aqueous Solution", Nature, Apr. 1995, pp. 555-559, vol. 374, Issue 6522.

Goll et al., "Microvalves with bistable buckled polymer diaphragms," J. Micromech. Microeng., 1996, pp. 77-79, vol. 6.

Gravesen et al.; "Microfluids- A Review", Journal Micromech Microeng, 1993, pp. 168-192, vol. 3.

Harrison et al., "Micromachining a Miniaturized Capillary Electrophoresis-Based Chemical Analysis System on a Chip," Science, 1993, pp. 895-897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem., 1999, 71(20):4781-4785.

Houseal et al. "Real Time Imaging of Single DNA Molecules with Fluorescent Microscopy", Biophysical Journal, 1989, p. 507-516, vol. 56.

Hultman et al. "Bidirectional Solid-Phase Sequencing of In Vitro-Amplified Plasmid DNA" BioTechniques, 1991, pp. 84-93, vol. 10, No. 1.

Ikuta et al., "Three dimensional micro integrated fluid systems (MIFS) fabricated by stereo lithography," IEEE Kyushu Institute of Technology, 1994, pp. 1-6.

Ishijima, A. et al. "Simultaneous Observation of Individual ATPase and Mechanical Events by a Single Myosin Molecule During Interaction with Actin", Cell, Jan. 1998, p. 161-171, vol. 92.

Ishikawa, M. et al.; "Single-molecule detection by laser-induced fluorescence technique with a position-sensitive photon-counting apparatus", Jpn. Journal Appl. Phys, 1994, pp. 1571-1576, vol. 33, Part 1, No. 3A.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jacobson, K. et al.; "International Workshop on the Application of Fluorescence Photobleaching Techniques to Problems in Cell Biology", Workshop Summary, Federation Proceedings, 1983, pp. 72-79, vol. 42.

Jett, J. et al. "High-Speed DNA Sequencing: An Approach Based Upon Fluorescence Detection of Single Molecules", Journal of Bimolecular Structure & Dynamics, 1989, pp. 301-309, vol. 7, No. 2.

Kanbara et al. "Optimization of Parameters in a DNA Sequenator Using Fluorescence Detection", Bio/Technology, 1988, p. 816-821, vol. 6.

Kenis et al. "Microfabrication Inside Capillaries Using Multiphase Laminar Flow Patterning," Science, 1999, 285:83-85.

Khrapko et al. "A method for DNA sequencing by hybridization with oligonucleotide matrix" DNA Sequence-J. DNA Sequencing and Mapping, 1991, p. 375-388, vol. 1, Harwood Academic Publishers GmbH, Printed in the United Kingdom.

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lazowski et al. "Highly Sensitive Detection of Hybridization of Oligonucleotides to Specific Sequence of Nucleic Acids by Application of Fluorescence Resonance Energy Transfer", Antisense Nucleic Acid Drug Development, 2000, pp. 97-103, vol. 10.

Lee et al. "Laser-Induced Fluorescence Detection of a Single Molecule in a Capillary", Analytical Chemistry, 1994, pp. 4142-4149, vol. 66.

Lin et al. "Free-Space Micromachined Optical Switches for Optical Networking," IEEE J. Selected Topics in Quantum Electronics, 1999, pp. 4-9, vol. 5, No. 1.

Lötters et al. "The mechanical properties of the rubber elastic polymer polydimethylsiloxane for sensor applications," J. Micromech. Microeng., 1997, 7:145-147.

Lucy et al., "Characterization of the Cationic Surfactant Induced Reversal of Electroosmotic Flow in Capillary Electrophoresis," Anal. Chem., 1996, 68:300-305.

Macklin et al.; "Imaging and Time-Resolved Spectroscopy of Single Molecules at an Interface", Science, Apr. 12, 1996; pp. 255-258, vol. 272, No. 5259.

Marriott, G et al, "Time Resolved Imaging Microscopy", Biophys Journal, Dec. 1991, pp. 1374-1387, vol. 60.

Mertz, J. et al. "Single Molecule Detection by Two-Photon Excited Fluorescence", Optics Letters, 1995, p. 2532-2534, vol. 20, No. 24.

Muller et al., "Surface-Micromachined Microoptical Elements and Systems," Proceedings of IEEE, 1998, 86(8): 1705-1720.

Nie et al.; "Probing Individual Molecules with Confocal Fluorescence Microscopy", Science, Nov. 1994, p. 1018-1021, vol. 266, No. 5187.

Nyrén et al.; "Solid Phase DNA Minisequencing by an Enzymatic Luminometric Inorganic Pyrophosphate Detection Assay", Analytical Biochemistry, 1993, pp. 171-175, vol. 208.

Ohara, T et al. "Wired" Enzyme Electrodes for Amperometric Determination of Glucose or Lactate in the Presence of Interfering Substances, Anal. Chemistry, 1994, pp. 2451-2457, vol. 66.

Ohara, T. et al. "Glucose Electrodes Based on Cross-Linked [Os9bpy)$_2$Cl]$^{+/2+}$Complexed Poly(1-vinylimidazole) Films" Analytical Chemistry, 1993, pp. 3512-3517, vol. 65.

Okabe et al, "Do Photobleached Fluorescent Microtubules Move?: Re-evaluation of Fluorescence Laser Photobleaching both in Vitro and in Growing *Xenopus* Axon", Journal of Cellular Biology, 1993, pp. 1177-1186, vol. 120, No. 5, Rockefeller University Press.

Pethig, R. & Markx, G. "Applications of dielectrophoresis in biotechnology", Tibtech, Oct. 1997, pp. 426-432, vol. 15.

Plakhotnik, T. et al. "Single-molecule spectroscopy", Ann. Rev. Phys. Chem., 1997, pp. 181-212, vol. 48.

Qin et al., "Elastomeric Light Valves", Adv. Mater., 1997, pp. 407-410, vol. 9, No. 5.

Quake S.R. and Scherer A.; "From micro- to nanofacrication with soft materials", Science, Nov. 24, 2000; pp. 1536-1540, vol. 290, No. 5496.

Rapp. R., "LIGA micropump for gases and liquids," Sensors and Actuators A, 1994, pp. 57-61, vol. 40.

Ronaghi et al.; "Sequencing Method Based on Real-Time Pyrophosphate", Science, Jul. 1998, p. 363-365, vol. 281.

Roylance et al., "A Batch-Fabricated Silicon Accelerometer", IEEE Transactions on Electron Devices, Dec. 1979, pp. 1911-1917, vol. ED-26, No. 12.

Schasfoort et al., "Field-Effect Flow Control for Microfabricated Fluidic Networks," Science, 1999, 286:942-945.

Selvin, Paul "Fluorescence Resonance Energy Transfer", Methods in Enzymology, 1995, pp. 300-335, vol. 246.

Shoji et al.; "Smallest Dead Volume Microvalves for Integrated Chemical Analyzing Systems", Proceedings of Transducers '91, 1991, pp. 1052-1055, San Francisco.

Shoji, S., "Fluids for Sensor Systems", Topics in Current Chemistry, 1998, pp. 162-188, vol. 194, Springer Verlag Berlin Heidelberg.

Smith et al. "Fluorescence detection in automated DNA sequence analysis", Nature, Jun. 1986, pp. 674-679, vol. 321.

Smith et al. "The synthesis of oligonucleotides containing an aliphatic amino group at the 5' terminus: synthesis of fluorescent DNA primers for use in DNA sequence analysis" Nucleic Acids Research, 1985, pp. 2399-2412, vol. 13, No. 7.

Smith et al.; "Direct Mechanical Measurements of the Elasticity of Single DNA Molecules by Using Magnetic Beads", Science, Nov. 1992, p. 1122-1126, vol. 258, No. 5085.

Smits, J.G., "Piezoelectric Micropump with Three Valves Working Peristaltically", Sensors and Actuators, 1990, pp. 203-206, vol. A21-A23.

Thompson, N. & Axelrod, D. "Immunoglobulin Surface-Binding Kinetics Studied by Total Internal Reflection with Fluorescence Correlation Spectroscopy", Biophys Journal, Jul. 1983, pp. 103-114, vol. 43.

Thompson, N. et al. "Measuring Surface Dynamics of Biomolecules by Total Internal Reflection Fluorescence with Photobleaching Recovery or Correlation Spectroscopy", Biophys Journal, Mar. 1981, pp. 435-454, vol. 33.

Tokunaga, M. et al. "Single Molecule Imaging of Fluorophores and Enzymatic Reactions Achieved by Objective-Type Total Internal Reflection Fluorescence Microscopy", Biochemical and Biophysical Research Communications, 1997, pp. 47-53, vol. 235.

Toneguzzo, F. et al, "Use of a Chemically Modified T7 DNA Polymerase for Manual and Automated Sequencing of Supercoiled DNA", BioTechniques, 1988, p. 460-469, vol. 6, No. 5.

Tufte et al., "Silicon Diffused-Element Piezoresistive Diaphragms," J. Appl. Phys., Nov. 1962, pp. 3322-3327, vol. 33, No. 11.

Ullmann's Encyclopedia of Industrial Chemistry, Sections 6 to 6.3, Topic: Carbon Black, Sixth Edition, 1999.

Unger et al.; "Monolithic Microfabricated Valves and Pups by Multilayer Soft Lithography", Science, Apr. 2000, pp. 113-116, vol. 288.

Unger et al.; "Single-molecule fluorescence observed with mercury lamp illumination", Biotechniques, Nov. 1999, p. 1008-1014, vol. 27, No. 5.

Vale et al.; "Direct observation of single kinesin molecules moving along microtubules", Nature, Apr. 1996, p. 451-453, vol. 380, Issue 6573.

Van De Pol et al., "Micro Liquid Handling Devices—A Review", Micro Systems Technologies, 1990, pp. 799-805, vol. 90.

Vieider et al.; "A Pneumatically Actuated Micro Valve with a Silicon Rubber Membrane for Integration with Fluid Handling Systems", Proceedings of Transducers '95, 1995, pp. 284-286, Stockholm, Sweden.

Washizu et al., "Molecular Dielectrophoresis of Biopolymers," IEEE Transactions on Industry Applications, 1994, 30(4):835-843.

Watkins, R. et al. "A Total Internal-Reflection Technique for the Examination of Protein Adsorption" J. Biomedical Mater. Res., 1977, pp. 915-938, vol. 11.

Wedekind, P. et al. "Scanning microphotolysis: a new photobleaching technique based on fast intensity modulation of a scanned laser beam and confocal imaging", Journal of Microscopy, Oct. 1994, pp. 23-33, vol. 176, Part 1.

Weiss, Shimon "Fluorescence Spectroscopy of Single Biomolecules", Science, Mar. 1999, p. 1676-1683, vol. 283, No. 5408.

Xia et al., "Complex Optical Surfaces Formed by Replica Molding Against Elastomeric Masters," Science, 1996, 273:347-349.

Xia et al., "Soft Lithography," Angew. Chem. Int. Ed., 1998, 37:551-575.

Xu, Xiao-Hong & Yeung, E. "Direct Measurement of Single-Molecule Diffusion and Photodecomposition in Free Solution", Science, Feb. 1997, pp. 1106-1109, vol. 275, No. 5303.

Xu, Xiao-Hong & Yeung, E. "Long-Range Elecrostatic Trapping of Single-Protein Molecules at a Liquid-Solid Interface", Science, Sep. 1998, p. 1650-1653, vol. 281, No. 5383.

Yang et al. "A Mems Thermopneumatic Silicone Membrane Valve", Proceedings of IEEE 10th Annual International Workshop on MicroElectro Mechanical Systems, Sensors and Actuators, 1998, A64(1):101-108.

Yazdi et al. "Micromachined Inertial Sensors," Proceedings of IEEE, 1998, 86(8):1640-1659.

Yershov et al. "DNA analysis and diagnostics on oligonucleotide microchips", Proc. National Academy of Science, May 1996, p. 4913-4918, vol. 93, U.S.A.

Young et al. "Contoured elastic-membrane microvalves for microfluidic network integration," J. Biomechanical Engineering, 1999, 121:2-6.

Zdeblick et al. "A Microminiature Electric-to-Fluidic Valve", *Transducers '87, The 4th International Conference on Solid State Sensors and Actuators*. Reprinted in *Micromechanics and MEMS Classic and Seminal Papers to 1990*, 1997, IEEE Press, USA.

Agrawal, S. et al., "Site Specific Functionalization of Oligodeoxynucleotides for Non-Radioactive Labelling", *Tetrahedron Letters*, vol. 31, No. 11, pp. 1543-1546 (1990).

Amit, B. et al., "Photosensitive Protecting Groups of Amino Sugars and Their Use in Glycoside Synthesis . . . Derivatives", *J. Org. Chem.*, 39(2):192-6(1974).

Beaucage, S. et al., "Advances in the Synthesis of Oligonucleotides by the Phosphoramidite Approach" *Tetrahedron*, 48:2223-2311 (1992).

Beese, L. et al., "Structure of DNA Polymerase I Klenow Fragment Bound to Duplex DNA", *Science*, 260:352-355 (1993).

Braslavsky, I. et al., "Sequence information can be obtained from single DNA molecules", *PNAS*, vol. 100, No. 7, pp. 3960-3964 (Apr. 2003).

Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, pp. 199-209 (1996).

Butler, D. et al., "Draft data leave geneticists with a mountain still to climb", *Nature*, vol. 405, Issue 6782, pp. 984-985 (May 2000).

Chen et al., *Prog. in Biochem. and Biophys.*, 22:223-227 (1995).

Chidgeavadze, Z. et al., "3'-Fluro-2',3'-dideoxyribonucleoside 5'-triphosphates: terminators of DNA synthesis", *FEBS Letters*, 183(2):275-278 (1985).

Chiu, D. et al., "Patterned deposition of cells and proteins onto surfaces by using three-dimensional microfluidic systems", *PNAS*, vol. 97, No. 6, pp. 2408-2413 (2000).

Chou, H. et al., "A microfabricated device for sizing and sorting DNA molecules", *PNAS*, vol. 96, pp. 11-13 (1999).

Decher, G. et al., "Buildup of ultrathin multiplayer films by a self-assembly process: III. Consecutively alternating adsorption of anionic and cationic polyelectrolytes on charged surfaces", *Thin Solid Films*, 210:831-835 (1992).

Delamarche, E. et al., "Patterned Delivery of Immunoglobulins to Surfaces Using Microfluidic Networks", *Science*, 276:779-781 (1997).

Doktycz, M. et al., Automation Technologies for Genome Characterization, Ch. 10 "Genosensors and Model Hybridization Studies", T. Beugelsdijk (Ed), John Wiley & Sons, Inc. (1997), pp. 205-225.

Doublie, S. et al., "Crystal structure of a bacteriophage T7 DNA replication complex at 2.2 Å resolution", *Nature*, vol. 391, pp. 251-258 (Jan. 1998).

Drmanac, R. et al., "Sequencing by hybridization: Towards an automated sequencing of one million M13 clones arrayed on membranes", *Electrophoresis*, 13:566-573 (1992).

Duffy, D. et al., "Patterning Electroluminescent Materials with Feature Sizes as Small as 5μm Using Elastomeric Membranes as Masks for Dry Lift-Off", *Advanced Materials*, vol. 11, No. 7, pp. 546-552 (1999).

Duffy, D. et al., "Rapid Prototyping of Microfluidic Systems in Poly(dimethylsiloxane)" *Anal. Chem.*, vol. 70, No. 23, pp. 4974-4984 (1998).

Duffy, D. et al., "Rapid prototyping of microfluidic switches in poly(dimethyl siloxane) and their actuation by electro-osmotic flow", *J. Micromech. Microeng.*, vol. 9, pp. 211-217 (1999).

Effenhauser, C. et al., "Integrated Capillary Electrophoresis on Flexible Silicone Microdevices: Analysis of DNA Restriction Fragments and Detection of Single DNA Molecules on Microchips", *Anal. Chem.*, vol. 69, No. 17, pp. 3451-3457 (1997).

Effenhauser, C. et al., "Integrated chip-based capillary electrophoresis", *Electrophoresis*, vol. 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Fahrenburg, J. et al., "A microvalve system fabricated by thermoplastic molding", *J. Micromech. Microeng.*, vol. 5, pp. 169-171 (1995).

Felicia, Y. et al., "Synthesis and Properties of Adenosine-5'-triphosphoro-γ-1-(5-sulfonic acid)naphthyl Ethylamidate: A Fluorescent Nucleotide Substrate for DNA-Dependent RNA Polymerase from *E. coli*", *Arch. Biochem. Biophys.*, 246(2):564-571 (1986).

Firtz, J. et al., "Electronic detection of DNA by its intrinsic molecular charge", *PNAS*, vol. 99, No. 22, pp. 14142-14146 (Oct. 2002).

Förster, T., "Delocalized Excitation and Excitation Transfer", Modem Quantum Chem., Istanbul Lectures, Part III, pp. 93-137, Academic Press, New York (1965).

Fu, A. et al., "A microfabricated fluorescence-activated cell sorter", *Nature Biotechnology*, vol. 17, pp. 1109-1111 (Nov. 1999).

Garcia, A., "Determination of Ion Permeability by Fluorescence Quenching", *Meth. in Enzymology*, 207:501-511 (1992).

Giusti, W. et al., "Synthesis and Characterization of 5'-Fluorescent-dye-labeled Oligonucleotides", *PCR Methods and Applications*, 2:223-227 (1993).

Goll, C. et al., "Microvalves with bistable buckled polymer diaphragms", *J. Micromech. Microeng.*, vol. 6, pp. 77-79 (1996).

Graveson, P. et al., "Microfluidics—a Review", *J. Micromech. Microeng.*, vol. 3, pp. 168-182 (1993).

Guilbault, G., Practical Fluorescence—Theory, Methods and Techniques, Chapters 1 and 3, and pp. 521-524, Marcel Dekker, Inc., New York (1973).

Gyllenstein, U. et al., "Generation of single-stranded DNA by the polymerase chain reaction and its application to direct sequencing of the HLA-DQA locus", *PNAS* 85:7652-56 (1988).

Hanna, M. et al., "Synthesis and characterization of a new photocrosslinking CTP analog and its use in photoaffinity labeling *E. coli* and T7 RNA polymerases", *Nucleic Acids Res.*, 21(9):2073-2079 (1993).

Harrison, D. et al., "Micromachining a Miniaturized Capillary Electrophoresis-Based Chemical Analysis System on a Chip", *Science*, 261:895-897 (1993).

Hasan, A. et al., "Photolabile Protecting Groups for Nucleosides: Synthesis and Photodeprotection Rates", *Tetrahedron*, 53(12):4247-4264 (1997).

Hosokawa, K. et al., "Handling of Picoliter Liquid Samples in a Poly(dimethylsiloxane) Based Microfluidic Device", *Anal. Chem.*, vol. 71, No. 20, pp. 4781-4785 (1999).

Hyman, E., "A New Method of Sequencing DNA", *Anal. Biochem.*, 174:423-436 (1988).

Ikuta, K. et al., "Three Dimensional Micro Integrated Fluid Systems (MIFS) Fabricated by Stereo Lithography", *IEEE Kyushu Institute of Tech.*, pp. 1-6 (1994).

Jacobs, J. et al., "Combinatorial chemistry—applications of light-directed chemical synthesis", *TIBTech*, vol. 12, pp. 19-26 (Jan. 1994).

Jacobson, S. et al., "High-Speed Separations on a Microchip", *Anal. Chem.*, vol. 66, No. 7, pp. 1114-1118 (1994).

Jacobson, S. et al., "Microfluidic Devices for Electrokinetically Driven Parallel and Serial Mixing", *Anal. Chem.*, vol. 71, No. 20, pp. 4455-4459 (1999).

Johnston, R. et al., "Autoradiography using storage phosphor technology", *Electrophoresis*, 11:355-360 (1990).

Joos, B. et al., "Covalent Attachment of Hybridizable Oligonucleotides to Glass Supports", *Anal. Biochem.* 247(1):96-101 (1997).

Kenis, P. et al., "Microfabrication Inside Capillaries Using Multiphase Laminar Flow Patterning", *Science*, 285:83-85 (1999).

Khandjian, E., "UV crosslinking of RNA to nylon membrane enhances hybridization signals", *Mole. Bio. Rep.* 11:107-115 (1986).

Kiefer, J. et al., "Crystal structure of a thermostable *Bacillus* DNA polymerase I large fragment at 2.1 Å resolution", *Structure*, 5:95-108 (1997).

Kim, Y. et al., "Crystal structure of *Thermus aquaticus* DNA polymerase", *Nature*, 376:612-616 (1995).

Kopp, M. et al., "Chemical Amplification: Continuous-Flow PCR on a Chip", *Science*, vol. 280, pp. 1046-1048 (May 1998).

Korolev, S. et al., "Crystal structure of the large fragment of *Thermus aquaticus* DNA polymerase I at 2.5 Å resolution: Structural basis for thermostability", *PNAS*, 92:9264-9268 (1995).

Kricka et al., Molecular Probing, Blotting and Sequencing, Ch. 1 and Table iX, Academic Press, New York (1995).

Krider, E. et al., "2'-Modified Nucleosides for Site-Specific Labeling of Oligonucleotides", *Bioconjug. Chem.*, vol. 13, No. 1, pp. 155-162 (2002).

Kutateladze et al., "2',3'-Dideoxy-3' aminonucleoside 5'-triphosphates are the terminators of DNA synthesis catalyzed by DNA polymerases", *Nuc. Acids Res.*, 12(3):1671-1686 (1984).

Lacoste, T. et al., "Ultrahigh-resolution multicolor colocalization of single fluorescent probes", *PNAS*, 97(17):9461-6 (2000).

Levene, M. et al., "Zero-Mode Waveguides for Single-Molecule Analysis at High Concentrations", *Science*, 299:682-686 (Jan. 2003).

Li, H. et al., "Ultrasensitive Coincidence Fluorescence Detection of Single DNA Molecules", *Anal. Chem.*, 75:1664-1670 (2003).

Li, H. et al., "Design, Synthesis, and Spectroscopic Properties of Peptide-Bridged Fluorescence Energy-Transfer Cassettes", *Bioconjugate Chem.*, 10:241-245 (1999).

Li, H. et al., "Structural Studies of the Klentaq 1 DNA Polymerase", *Current Organic Chem.*, 5:871-883 (2001).

Li, Z. et al., "A photocleavable fluorescent nucleotide for DNA sequencing and analysis", *PNAS*, vol. 100, No. 2, pp. 414-419 (2003).

Loh, E. et al., "Polymerase Chain Reaction with Single-Sided Specificity: Analysis of T Cell Receptor δ Chain", *Science* 243:217-220 (1989).

Lopez, G. et al., "Fabrication and Imaging of Two-Dimensional Patterns of Proteins Adsorbed on Self-Assembled Monolayers by Scanning Electron Microscopy", *J. Amer. Chem. Soc.*, 115:10774-81 (1993).

Lotters, J. et al., "The mechanical properties of the rubber elastic polymer polydimethyl-siloxane for sensor applications", *J. Micromech. Microeng.*, vol. 7, pp. 145-147 (1997).

Lucy, C. et al., "Characterization of the Cationic Surfactant Induced Reversal of Electroosmotic Flow in Capillary Electrophoresis", *Anal. Chem.*, 68:300-305 (1996).

Mastrangelo, C. et al., "Vacuum-Sealed Silicon Micromachined Incandescent Light Source", *IDEM*, 89:503-506 (1989).
Muller, R. et al., "Surface-Micromachined Microoptical Elements and Systems", *IEEE* vol. 86, No. 8, pp. 1705-1720 (1998).
Nelson, P. et al., "Bifunctional oligonucleotide probes synthesized using a novel CPG support are able to detect single base pair mutations", *NAR*, 17(18):7187-7194 (1989).
Ochman, H. et al., "Genetic Applications of an Inverse Polymerase Chain Reaction", *Genetics* 120:621-623 (1988).
Ollis, D. et al., Structure of large fragment of *E. coli* DNA polymerase I complexed with dTMP, *Nature*, 313:762-766 (1985).
Oroskar, A. et al., "Detection of immobilized amplicons by ELISA-like techniques" *Clin. Chem.*, 42(9):1547-1555 (1996).
Patchornik, A. et al., "Photosensitive Protecting Groups" *J. Amer. Chem. Soc.*, 92(21):6333-37 (1970).
Perkins, T. et al., "Relaxation of a Single DNA Molecule Observed by Optical Microscopy", *Science*, 264:822-826 (May 1994).
Pisani, F. et al., "Domain Organization and DNA-Induced Conformational Changes of an Archaeal Family B DNA Polymerase", *Biochemistry*, vol. 35, pp. 9158-9166 (Jul. 1996).
Ploem, J., Ch. 1 "Fluorescence Microscopy", Fluorescent and Luminescent Probes for Biol. Activity, Mason, T. Ed., Academic Press, London, pp. 1-11 (1993).
Qin, D. et al., "Elastomeric Light Valves", *Advanced Materials*, vol. 9, No. 5, pp. 407-410 (1997).
Qin, P. et al., "Site-Specific Labeling of RNA with Fluorophores and Other Structural Probes", *Methods*, vol. 18, No. 1, pp. 60-70 (May 1999).
Quake, S. et al., "Fluorescent Photobleaching Method for Sequencing DNA", pp. 1-10, circa 1996.
Quake, S. et al., "Polymer Physics with Single Molecules of DNA" (Dept. of Physics), a colloquim by Stephen Quake, Stanford University, Feb. 22, 1996. (Presented at Laser Spectroscopy XII Intl. Conference, Italy, Jun. 1995.).
Rigler, R., "Enzymatic single molecule DNA sequencing—by deposition of individual nucleic acid bases on solid substrate", Abstract from SE patent appl. No. SE 9500589, 1 page, filed Aug. 18, 1996.
Rigler, R., "Fluorescence correlations, single molecule detection and large number screening—Applications in Biotechnology", *J. Biotech.*, 41:177-186 (1995).
Rosenblum, B. et al., "New dye-labeled terminators for improved DNA sequencing patterns", *Nucleic Acids Research*, vol. 25, No. 22, pp. 4500-4504 (Nov. 1997).
Rosenblum, B. et al., "Improved single-strand DNA sizing accuracy in capillary electrophoresis", *Nucleic Acids Research*, vol. 25, No. 19, pp. 3925-3929 (Oct. 1997).
Ruth, J. et al., "Nucleoside Analogues with Clinical Potential in Antivirus Chemotherapy", *Molecular Pharmacology*, 20:415-422 (1981).
Sanger, F. et al., "DNA sequencing with chain-terminating inhibitors", *PNAS*, 74(12):5463-67 (Dec. 1977).
Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).
Schasfoort, R. et al., "Field-Effect Flow Control for Microfabricated Fluidic Networks", *Science*, vol. 286, pp. 942-945 (1999).
Seeger, S. et al., "Single molecule fluorescence—High Performance Molecular Diagnosis and Screening", translated from *BIOforum*, pp. 179-185, Apr. 1998.
Shackelford, James F., Intro. to Materials Science for Engineers, 3rd Edition, Prentice-Hall, Inc., Macmillan Publ. Co. (1992).
Sharma, P., Gupta, K. et al., "A general method for the synthesis of 3'-sulfhydryl and phosphate group containing oligonucleotides", *Nucleic Acids Res.*, 19(11):3019-25 (1991).
Smith, S. et al., "Direct Mechanical Measurements of the Elasticity of Single DNA Molecules by Using Magnetic Beads", *Science* 258:1122-26 (1992).
Sproat, B. et al., "The synthesis of protected 5'-mercapto-2',5'-dideoxyribonucleoside-3'-O-phosphoramidities; uses of 5'-mercapto-oligodeosyribonucleotides", *Nucleic Acids Res.*, 15(12):4837-48 (1987).
Taveira, N. et al., "Detection of HIV1 proviral DNA by PCR and hybridization with digoxigenin labeled probes", *Mol. Cell Probes*, vol. 6, No. 4, pp. 265-270 (1992).
Taylor, D. et al., "Characterization of chemisorbed monolayers by surface potential measurements", *J. Phys. D. Appl. Phys.* 24:1443-50 (1991).
Terry, S. et al., "A Gas Chromatographic Air Analyzer Fabricated on a Silicon Wafer", *IEEE Trans. on Electron Dev.*, vol. ED-26, No. 12, pp. 1880-1886 (1979).
Theisen, P. et al., "Fluorescent dye phosphoramidite labeling of oligonucleotides", *Nucleic Acids Symp. Ser.*, vol. 27, pp. 99-100 (1992).
Tyagi, S. et al., "Multicolor molecular beacons for allele discrimination", *Nat. Biotechnol.*, 16:49-53 (1998).
Unger, M. et al., "Monolithic Microfabricated Valves and Pumps by Multilayer Soft Lithography", *Science*, 288:113-116 (2000).
Wang, G. et al., "Design and Synthesis of New Fluorogenic HIV Protease Substrates Based on Resonance Energy Transfer", *Tetrahedron Lett.*, 31(45):6493-96 (1990).
Washizu, M. et al., "Molecular Dielectrophoresis of Biopolymers", *IEEE Trans. on Industry Applications*, vol. 30, No. 4, pp. 835-843 (1994).
Webster, J. et al., "Monolithic Capillary Gel Electrophoresis Stage with On-Chip Detector", Intl. Conf. on MEMS (MEMS 96), pp. 491-496 (1996).
Williams, N. et al., "Exploring the Adenine Nucleotide Binding Sites on Mitochondrial F1-ATPase with a New Photoaffinity Probe,3'-O-(4-Benzoyl)benzoyl Adenosine 5'-Triphosphate", *J. Biol. Chem.*, 237(6):2834-41 (1982).
Wuite, G. et al., "Single-molecule studies of the effect of template tension on T7 DNA polymerase activity", *Nature*, 404:103-6 (2000).
Xia, Y. et al., "Soft Lithography", Angew. Chem. Int. Ed., vol. 37, pp. 550-575 (1998).
Xia, Y. et al., "Complex Optical Surfaces Formed by Replica Molding Against Elastomeric Masters", *Science*, 273:347-349 (1996).
Yang, X. et al., "A MEMS thermopneumatic silicone rubber membrane valve", Proc. of the IEEE 10th Annual Intl. Workshop on MicroElectro Mech. Systems, Sensors and Actuators, vol. A64, No. 1, pp. 101-108 (1998).
Young, A. et al., "Contoured Elastic-Membrane Microvalves for Microfluidic Network Integration", *J. Biomech. Eng.*, 121:2-6 (1999).
Zhu, Z. et al., "Molecular Mechanism Controlling the Incorporation of Fluorescent Nucleotides into DNA by PCR", *Cytometry*, 28:206-211 (1997).
Zhu, Z. et al., "Directly labeled DNA probes using fluorescent nucleotides with different length linkers", *Nucleic Acids Res.*, vol. 22, No. 16, pp. 3418-3422 (1994).
Zuckerman, R. et al., "Efficient methods for attachment of thiol specific probes to the 3' ends of synthetic oligodeoxyribonucleotides", *Nucleic Acids Res.*, 15(13):5305-5321.
Stephen R. Quake et al., "Methods and Apparatuses For Analyzing Polynucleotide Sequences", pending U.S. Appl. No. 09/707,737, filed Nov. 6, 2000.
Amit, B. et al., "Photosensitive Protecting Groups of Amino Sugars and Their Use in Glycoside Synthesis . . . Derivatives", 1. *Org. Chem.*, 39(2):192-6 (1974).
Augustin, M.A., W. Ankenbauer, and B. Angerer, "Progress towards single-molecule sequencing: enzymatic synthesis of nucleotide-specifically labeled DNA." Journal of Biotechnology, 2001. 8(13): p. 289.
Bai, X., et al., "Photocleavage of a 2-nitrobenzyl linker bridging a fluorophore to the 5' end of DNA." Proc Natl Acad Sci USA, 2003, vol. 100(2). p. 409-13.
Bennett et. al., "Solexa Sequencing chemistry can be applied to different platforms which will have common elements in detection and data processing." Pharmacogenomics (2004) 5(4).
Biesalski et al., "Preparation and Characterization of a Polyelectrolyte Monolayer Covalently Attached to a Planar Solid Surface." Macromolecules 111, 32, 2309-2316. Article was published on the web Mar. 10, 1999.

Black, D.L., Protein diversity from alternating splicing: A challenge for bioinformatics and post genome biology. Cell, 2000. 103(3): p. 367-370.

Blattner, F.R., et al., "The Complete genome sequence of *Escherichia coli* K-12." Science, 1997.277(5331):p. 1453-74.

Boles et. al., "High-Resolution Mapping of Carcinogen Binding Sites on DNA" 1986, 25, 3039-3043.

Brakmann, S. and P. Nieckchen, "The large fragment of *Escherichia coli* DNA polymerase I can synthesize DNA exclusively from fluorescently labeled nucleotides." Chembiochem, 2001. 2(10):p. 773-777.

Brackmann et. al, "Optimal Enzymes for Single-Molecule Sequencing" 18, D-04103.

Bridgman, A. et al., "An improved method for the synthesis of mercurated Dutp. Enzymatic synthesis of Hg-Iabelled DNA of high molecular weight suitable for use in an image based DNA sequencing strategy", *DNA Seq.*, vol. 6, No. 4, pp. 199-209 (1996).

Canard, B., B. Cardona, .and R.S. Sarfati, "Catalytic editing properties of DNA polymerases." Proc Natl Acad Sci USA, 1995. 92(24): p. 10859-63.

Chou et al., "A Microfabricated Rotary Pump". Biomedical Microdevices. vol. 3: p. 323 (2001).

Crocker, J.C. and D.G. Grier, "Methods of digital video microscopy for colloidal studies." Journal of Colloid and Interface Science, 1996. 179(1): p. 298-310.

Dapprich, J., "Single-molecule DNA digestion by lambda-exonuclease." Cytometry, 1999.36(3): p.163-168.

Debenham, J.S., et al., "Two New Orthogonal Amine-Protecting Groups that can be Cleaved under Mild or Neutral Conditions." Journal of the American Chemical Society, 1995. 117(11): p. 3302-3.

Decher G.;et al., "Fuzzy nanoassemblies : Toward layered polymeric multicomposites." Science, 1997.277(5330): p. 1232-1237.

Dickson et al., "Simultaneous Imaging of Individual Molecules aligned both parallel and perpendicular to the optic axis" vol. 81, No. 24, 1998.

Doktycz, M. et al., "Genosensors and Model Hybridization Studies", Automation Technologies for Genome Characterization, Ch. 10 T. Beugelsdijk (Ed), John Wiley & Sons, Inc. (1997), pp. 205-225.

Doublie, S. et al., "Crystal structure of a bacteriophage T7 DNA replication complex at 2.2 A resolution", *Nature*, vol. 391, pp. 251-258 (Jan. 1998).

Evangelista, R.A., et al. "Characterization of fluorescent nucleoside triphosphates by capillary electrophoresis with laser-induced fluorescence detection: action of alkaline phosphatase and DNA polymerase." Anal Biochem, 1996.235(1): p. 89-97.

Fahrenberg et al., "A microvalve system fabricated by thermoplastic molding," J. Micromech. Microeng., vol. 5, pp. 169-171 (1995).

Ferguson, et al., "A fiber-optic DNA biosensor microarray for the analysis of gene expression," Nature Biotechnology, vol. 14, pp. 1681-1684 (1996).

Firtz, I. et al., "Electronic detection of DNA by its intrinsic molecular charge", *PNAS*, vol. 99, No. 22, pp. 14142-14146 (Oct. 2002).

Forster, T., "Delocalized Excitation and Excitation Transfer", Modern Quantum Chem., *Istanbul Lectures*, Part TII, pp. 93-137, Academic Press, New York (1965).

Fu e al., "An integrated microfabricated cell sorter". Anal Cherm, 2002. 74(11): p. 451-7.

Garcia, A., "Detennination of Ion Penneability by Fluorescence Quenching", *Meth. in Enzymology*, 207:501-511 (1992).

Gardner et al., "Comparative kinetics of nucleotide analog incorporation by Vent DNA polymerase," J. Biol. Chem., 279, No. 12, Mar. 19, 2004, 11834-11842.

Giller et al., "Incorporation of reporter molecule-labeled nucleotides by DNA polymerases. 1. Chemical synthesis of various reporter group-labeled 2'deoxyribonucleoside-5'-triphosphates," Nucleic Acids Res., 31, No. 10, 2003, 2630-2635.

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA." Proceedings of the National Academy of Sciences of the United States of America, 2002. 99(9): p. 6005-6010.

Guilbault, G., "Practical Fluorescence—Theory, Methods and Techniques," Chapters 1 and 3, and pp. 521-524, Marcel Dekker, Inc., New York (1973).

Ha, "Single molecule dynamics studied by polarization modulation," Phys. Rev. Lett., 77, No. 19, Nov. 4, 1996, 39793982.

Ha, "Single molecule spectroscopy with automated positioning," Appl. Phys. Lett. 70, No. 6, Feb. 10, 1997, 782-784.

Ha, T., "Single-molecue fluorescence resonance energy transfer." Methods, 2001. 25(1): p. 78-86.

Hanna, M. et al., "Synthesis and characterization of a new photocrosslinking CTP analog and its use in photoaffrnity labeling *E. coli* and T7 RNA polymerases", *Nucleic Acids Res.*, 21(9):2073-2079 (1993).

Hansen, C.J , et al., "A robust and scalable microfluidic metering method that allows Protein crystal growth by free interface diffusion". Proc Natl Acad Sci U S A, 2002. 99 (26): p. 16531-6.

Harris, J.M., "Introduction to Biochemical and biomedical applications of poly(ethylene glycol)." poly(ethylene glycol) chemistry, Harris, J. M., Ed.; Plenum Press: New York, 1992: pp. 1-14.

Hubner et al., "Direct observation of the triplet lifetime quenching of single dye molecules by molecular oxygen," J. Chem. Physics, 115, No. 21, Dec. 1, 2001, 9619-9622.

Ishii et al., "Fluorescence resonance energy transfer between single fluorophores attached to a coiled-coil protein in aqueous solution," Chemical Physics, 247, 1999, 163-173.

Jacobs et al., "Combinatorial chemistry—applications oflight-directed chemical synthesis", *TIBTech*, vol. 12, pp. 19-26 (Jan. 1994).

Jongeneel, C.V., et al., "Comprehensive sampling of gene expression in human cell lines with massively parallel signature sequencing". Proc Natl Acad Sci U S A, 2003.100(8): p. 636-639.

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kawai et al., "A simple method of detecting amplified DNA with immobilized probes on microtiter wells" 209, 63-69 (1993) Analytical Biochemistry.

Kelso et al., "Single-cell analysis by RT-PCR reveals differential expression of multiple type 1 and 2 cytokine genes among cells within polarized CD4+ T cell populations," International Immunology, 11, No. 4, 1999, 617-621.

Kenney, et al., "Mutation Typing Using Electrophoresis and Gel-Immobilized Acrydite™ Probes," BioTechniques, vol. 25, No. 3, pp. 516-521, (1998).

Khandflan, E., "UV cross linking of RNA to nylon membrane enhances hybridization signals", Mole. Bio, Rep. 11: 107-115 (1986).

Kiefer, J. et al., "Crystal structure of a thermostable *Bacillus* DNA polymerase I large fragment at 2.1 A resolution", *Structure*, 5:95-108 (1997).

Kirkland, T.A., D.M. Lynn, and R.H. Grubbs, "Ring-Closing Metathesis in Methanol and Water." Journal of Organic Chemistry, 1998.63(26): p. 9904-9909.

Knerr, L. and R.R. Schmidt, "Application of a ring-closing-metathesis-based linker to the solidphase synthesis of oligosaccharides" Synlett, 1999. 11: p. 1802-1804.

Korolev, S. et al., "Crystal structure of the large fragment of *Thermus aquaticus* DNA polymerase I at 2.5 A resolution: Structural basis for thermo stability", *PNAS*, 92:9264-9268 (1995).

Kricka et al., "Labels, Labeling, Analytical Strategies, and Applications." Ch. 1 and Table Ix, Academic Press, New York (1995).

Krider, E. et al., "2'-Modified Nucleosides for Site-Specific Labeling of Oligonucleotides", Bioconjuf{. Chern., vol. 13, No. 1, pp. 155-162 (2002).

Chidgeavadze et al., '2',3'-Dideoxy-3'aminonucleoside 5'-triphosphates are the terminators of DNA synthesis catalyzed by DNA polymerases, *Nuc. Acids Res.*, 12(3):1671-1686 (1984).

Lander, E.S., et al., "Initial sequencing and analysis of the human genome." Nature, 2001. 409(6822): p. 860-921.

Levsky et al., "Single-cell gene expression profiling," Science, 297, Aug. 2, 2002, 836-840.

Li, Y. et al., "Design, Synthesis, and Spectroscopic Properties of Peptide-Bridged Fluorescence Energy-Transfer Cassettes", Bioconjuate Chern., 10:241-245 (1999).

Li, Y. et al., "Structural Studies of the Klentaq1 DNA Polymerase", Current Organic Chern., 5:871-883 (2001).

Lin, L. et al., "Free-Space Micromachined Optical Switches for Optical Networking", IEEE J. of Selected Topics in Quantunm Electronics, vol. 5, No. 1, pp. 4-9 (Jan. 1999).

Liu, J., M.. Enzelberger, and S. Quake, "A nanoliter rotary device for polymerase chain reaction" Electrophoresis, 2002.23(10): p. 1531-6.

Lodder, M., et al., "Misacylated Transfer RNAs Having a Chemically Removable Protecting Group." Journal of Organic Chemistry, 1998.63(3): p. 794-803.

Loh, E. et al., "Polymerase Chain Reaction with Single-Sided Specificity: Analysis of T Cell Receptor D Chain", Science 243:217-220 (1989).

Lopez, G. et al., "Fabrication and Imaging of Two-Dimensional Patterns of Proteins Adsorbed on Self-Assembled Monolayers by Scanning Electron Microscopy", J. Arner. Chern. Soc., 115:10774-81 (1993).

Ludwig, J and F. Eckstein, "Rapid and efficient synthesis of nucleoside 5'-0-(1 thiotriphosphates), 5'-triphosphates and 2',3'-cyclophosphorothioates using 2-chloro-4H-1,3,2benzodioxaphosphorin- 4-one." Journal of Organic Chemistry, 1989. 54(3): p. 631-635.

Maier, B., D. Bensimon, and V. Croquette, "Replication by a single DNA polymerase of a stretched single-stranded DNA." Proceedings of the National Academy of Sciences of the United States of America, 2000.97(22): p. 12002-12007.

Marziali, A. and M. Akeson, "New DNA sequencing methods." Annual Review of Biomedical Engineering, 2001. 3: p. 195-223.

Meiners, J.C and S.R. Quake, "Fernonewton force spectroscopy of single extended DNA. molecules." Phys Rev Lett, 2000. 84(21): p. 5014-7.

Meller, A., et al., "Rapid nanopore discrimination between single polynucleotide molecules." Proceedings of the National Academy of Sciences of the United States of America, 2000.97(3): p. 1079-1084.

Metzker et al., "Elimination of residual natural nucleotides from 3'-O-modified-dNTP syntheses by enzymatic mop-up," BioTechniques, 25, Nov. 1998, 814-817.

Metzker, M.L., et al., "Termination of DNA synthesis by novel 3'-modified-deoxyribonucleoside 5'-triphosphates." Nucleic Acids Res, 1994.22(20): p. 4259-67.

Moe et al., Rapid Detection of Clinically Relevant Bacteria in Platelets Using the Hybriscan Bacetrial Detection system, Journal of the American Society of Hematology, 96, No. 11, 2000, 4155.

Ollis, D. et al., Structure of large fragment of E. coli DNA polymerase I complexed with Dtmp, Nature, 313:762-766 (1985).

Patchornik, A. et al., "Photosensitive Protecting Groups" J. Arner. Chern. Soc., 92(21):6333-37 (1970).

Padmaja, T., et al., "Enzymatically degradable prodrugs: a novel methodology for drug linkage." Journal of Applied Polymer Science, 2002.85(10): p. 2108-2118.

Pennisi, E., "Gene researchers hunt bargins, fixer-uppers." Science, 2002. 298(5594): p. 735-736.

Perales et al., "Enhancement of DNA, cDNA synthesis and fidelity at high temperatures by a dimeric single-stranded DNA-binding protein," Nucleic Acids Res., 31, No. 22, 2003, 6473-6480.

Pisani, F. et at, "Domain Organization and DNA-Induced Conformational Changes of an Archaeal Family B DNA Polymerase", Biochemistry, vol. 35, pp. 9158-9166 (Jul. 1996).

Ploem, J., Ch. 1 "Fluorescence Microscopy", Fluorescent and Luminescent Probes for BioL Activity, Mason, T. Ed., Academic Press, London, pp. 1-11 (1993).

Quake, Stephen R. et al., "Methods and Apparatuses For Analyzing Polynucleotide Sequences", pending U.S. Appl. No. 09/707,737, filed Nov. 6, 2000.

Guillier, F., D. Orain, and M. Bradley, "Linkers and Cleavage Strategies in Solid-Phase Organic Synthesis and Combinatorial Chemistry." Chemical Reviews, 2000. 100(6): p. 2091-2157.

Rosenblum, B. et al., "New dye-labeled terminators for improved DNA sequencing patterns",Nucleic Acids Research, vol. 25, No. 22, pp. 4500-4504 (Nov. 1997).

Sarfati, S.R., et al., "Synthesis of fluorescent derivatives of 3'-O-(6-aminohexanoyl)pyrimidine nucleosides 5'-triphosphztes that act as DNA polymerase substrates reversibly tagged at C-3'." Journal of the Chemical Society, Perkin Transactions 1: Organic and Bio-Organic Chemistry, 1995.9: p. 1163-71.

Sato, E. et al., "Bimane Conjugates of 5-Halogenouridylic Acids as Fluorogenic Substrates for Phosphodiesterase I", J. Chern. Research (S), Issue 10, pp. 390-391 (1994).

Sauer, M., et al.., "Single molecule DNA sequencing in submicrometer channels: state of the art and future prospects." Journal of Biotechnology, 2001. 86(3): p. 181.

Sharma, P., Gupta, K. etal., "A general method for the synthesis of3'-sulfhydryl and phosphate group containing oligonucleotides", Nucleic Acids Res., 1901):3019-25 (1991).

Shendure et al., "Advanced sequencing technologies: Methods and goals," Nature, 5, May 2004, pp. 335-344.

Song et al., "Influence of the triplet excited state on the photobleaching kinetics of fluorescein in microscopy," Biophysics J., 70, Jun. 1996, 2959-2968.

Strausberg, R L, et al., "The mammalian gene collection." Science, 1999.286(5439): p. 455-7.

Tasara et al., "Incorporation of reporter molecule-labeled nucleotides by DNA polymerases. II. High-density labeling of natural DNA," Nucleic Acids Res., 31, No. 10, 2003, 2636-2646.

Taveira, N. et al., "Detection of HI VI proviral DNA by PCR and hybridization with digoxigenin labeled probes", Mol. Cell Probes, vol. 6, No. 4, pp. 265-270 (1992).

Taylor, D. et al., "Characterization of chemisorbed monolayers by surface potential measurements",J. Phys. D. Appl. Phys. 24:1443-50 (1991).

Thorsen, T. S.J. Maerkl, and S.R. Quake, "Microfluidic large-scale integration." Science, 2002 298(5593): p. 580-4.

Trager, R. S., "DNA sequencing—Venter's next goal: 1000 human genomes." Science, 2002. 298(5595): p. 947-947.

Van Dam, R.M. and S.R Quake, "Gene expression analysis with universal n-mer arrays." Genome Res, 2002. 12(1): p. 145-52.

Van Oijen et al., "Single molecule kinetics of λ exonuclease reveal base dependence and dynamic disorder," Science, 301, Aug. 29, 2003, 1235-1238.

Venter, J.L., et al., "The sequence of the human genome." Science, 2001. 291(5507): p. 1304-1351.

Walker, M.G., et al., "Prediction of gene function by genome-scale expression analysis: Prostate cancer-associated genes.": Genome Researce, 1999. 9(12): p. 1198-1203.

Wang, M.D., et al., "Force and Velocity measured for single molecules of RNA polymerase." Science, 1998.282(5390): p. 902-907.

Weber, J.L. and E.W. Myers, "Human whole-genome shotgun sequencing." Genome Research, 1997.7(5): p. 401-409.

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Welch, M.B. and K. Burgess, "Synthesis of fluorescent, photolabile 3'-O-protected nucleoside triphosphates for the base addition sequencing scheme." Nucleosides Nucleotides, 1999. 18(2): p. 197-201.

Williams, N. et al., "Exploring the Adenine Nucleotide Binding Sites on Mitochondrial FI-ATPase with a New Photoaffmity Probe, 3'-0-(4-Benzoyl)benzoyl Adenosine 5'-Triphosphate", J. Bioi. Chem., 237(6):2834-41 (1982).

Winter et al., "Direct gene expression analysis," Curr. Pharm. Biotech., 5, 2004, 191-197.

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the. effect of template tension on T7 DNA polymerase activity", *Nature*, 404:103-6 (2000).

Xia, G., et al., "Directed evolution of novel polymerase activities: mutation of a DNA polymerase into a efficient RNA polymerase." Proc Natl Acad Sci USA; 2002. 99(10) p. 6597-602.

Xie, "Single molecule approach to dispersed kinetics and dynamic disorder: Probing conformational fluctuation and enzymatic dynamics," J. Chem. Physics, 117, No. 24, Dec. 22, 2002, 11024-11032.

Yu., et al., "Cyanine dye dUTP analogs for enzymatic labeling of DNA probes." Nucleic Acids Res, 1994.22(15): p. 3226-32.

Zuckerman, R. et al., "Efficient methods for attachment ofthiol specific probes to the 3' ends of synthetic oligodeoxyribonucleotides", *Nucleic Acids Res.*, 15(13):5305-5321.

Canard, et al., "DNA polymerase fluorescent substrates with reversible 3'-tags". Gene, 1994. 148(1): p. 1-6.

Cheng et al., "High-speed DNA sequence analysis," *Prog. in Biochem. and Biophys.*, vol. 22, pp. 223-227 (1995).

Driscoll et al., "Atomic-Scale Imaging of DNA Using Scanning Tunneling Microscopy." Nature, 1990.346(6281): p. 294-296.

Goodwin, P.M., et al., "Application of single molecule detection to DNA sequencing." Nucleosides & Nucleotides, 1997. 16(5-6): p. 543-550.

Ha, "Single-molecule fluorescence methods for the study of nucleic acids," Current Opinion in Struct Bio, 11, 2001, 287-292.

Ha et al., "Single-molecule fluorescence spectroscopy of enzyme conformational dynamics and cleavage mechanism." Proceedings of the National Academy of Sciences of the United States of America, 1999.96(3): p. 893-898.

Harding et al., "Single-molecule detection as an approach to rapid DNA sequencing," Trends in Biotechnology, vol. 10, 1992.

Howorka, et al., "Sequence-specific detection of individual DNA strands using engineered nanopores." Nature Biotechnology, 2001. 19(7): p. 636-639.

Ishijima, A. et al., "Simultaneous Observation of Individual ATPase and Mechanical Events by a Single Myosin Molecule during Interaction with Actin", *Cell*, vol. 92, pp. 161-171, (Jan. 1998).

Kovacs et al., "Simple synthesis of 5-vinyl-and 5-ethynyl-2' deoxyuridine 5'-triphosphates". Tetrahedron Letters, 1988. 29(36): p. 4525-8.

Macklin, J. et al., "Imaging and Time-Resolved Spectroscopy of Single Molecules at an Interface", *Science*, vol. 272, No. 5259, pp. 255-258 (Apr. 1996).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 1998.17(9-11): p. 2021-2025.

Rasolonjatovo, I. and Sarfati, "Development of a new DNA sequencing method: 3'-ester cleavage catalyzed by Taq DNA polymerase." Nucleosides & Nucleotides, 1999. 18(4 & 5): p. 1021-1022.

Rigler, R, et al, "DNA-sequencing at the single molecule level." Journal of Biotechnology, 2001. 86(3): p. 161.

Ronaghi, M et al., "Real-Time DNA Sequencing Using Detection of Pyrophosphate Release." Analytical BioChemistry, 242, No. 0432, 1996.

Tufte, O. et al., "Silicon Diffused-Element Piezoresistive Diaphragms", *J. Applied Phys.*, vol. 31, No. 11, pp. 3322-3327 (Nov. 1962).

Watkins, R. et al., "A Total Internal-Reflection Technique for the Examination of Protein Adsorption", *J. Biomed. Mater. Res.*, vol. 11, pp. 915-938 (1977).

Werner et al "Progress towards single-molecule DNA sequencing: a one color demonstration." J Biotechnol, 2003. 102(1): p. 1-14.

* cited by examiner

The Polymerase Is Active on the Surface

About 40% of the red spots map on to green spots. With these concentrations the probability for this correlation to occur randomly calculated to be about $10^{-50}$ DNA primer location (Cy5)

dCTP Incorporation location (Cy3)

Bleaching in Steps Proves Multiple Incorporation

SEQUENCE LISTING

```
<160> NUMBER OF SEQ ID NOS: 9

<210> SEQ ID NO 1
<211> LENGTH: 100
<212> TYPE: DNA
<213> ORGANISM: artificial sequence
<220> FEATURE:
<221> NAME/KEY: misc_feature
<223> OTHER INFORMATION: 7G oligonucleotide template

<400> SEQUENCE: 1
tcagtcatca gtcatcagtc atcagtcatc agtcatcagt catcagtcat cagtcatcag        60
tcatcagtca tcagtcatca gtcatcacac ggaggttcta                             100

<210> SEQ ID NO 2
<211> LENGTH: 14
<212> TYPE: DNA
<213> ORGANISM: artificial sequence
<220> FEATURE:
<221> NAME/KEY: misc_feature
<223> OTHER INFORMATION: p7G primer

<400> SEQUENCE: 2
tagaacctcc gtgt                                                         14

<210> SEQ ID NO 3
<211> LENGTH: 50
<212> TYPE: DNA
<213> ORGANISM: artificial sequence
<220> FEATURE:
<221> NAME/KEY: misc_feature
<223> OTHER INFORMATION: Mu50 oligonucleotide template

<400> SEQUENCE: 3
ctccagcgtg ttttatctct gcgagcataa tgcctgcgtc atccgccagc                  50

<210> SEQ ID NO 4
<211> LENGTH: 13
<212> TYPE: DNA
<213> ORGANISM: artificial sequence
<220> FEATURE:
<221> NAME/KEY: misc_feature
```

```
<223> OTHER INFORMATION: Cy5 labeled primer

<400> SEQUENCE: 4
gctggcggat gac                                                    13

<210> SEQ ID NO 5
<211> LENGTH: 100
<212> TYPE: DNA
<213> ORGANISM: artificial sequence
<220> FEATURE:
<221> NAME/KEY: misc_feature
<223> OTHER INFORMATION: 7G7A oligonucleotide template

<400> SEQUENCE: 5
tttgcttctt attctttgct tcttattctt tgcttcttat tctttgcttc ttattctttg    60
cttcttattc tttgcttctt attcttacac ggaggttcta                        100

<210> SEQ ID NO 6
<211> LENGTH: 79
<212> TYPE: DNA
<213> ORGANISM: artificial sequence
<220> FEATURE:
<221> NAME/KEY: misc_feature
<223> OTHER INFORMATION: 6TA6CG oligonucleotide template

<400> SEQUENCE: 6
ccattttttg cccccattt tttgccccc atttttgcc cccattttt tgcccccat         60 tttttacacg gaggttcta                                               79

<210> SEQ ID NO 7
<211> LENGTH: 14
<212> TYPE: DNA
<213> ORGANISM: artificial sequence
<220> FEATURE:
<221> NAME/KEY: misc_feature
<223> OTHER INFORMATION: 6TA6GC partial template

<400> SEQUENCE: 7 gcccccccatt tttt                                                   14

<210> SEQ ID NO 8
<211> LENGTH: 14
<212> TYPE: RNA
<213> ORGANISM: artificial sequence
<220> FEATURE:
<221> NAME/KEY: misc_feature
<223> OTHER INFORMATION: p7G primer extended product

<400> SEQUENCE: 8
aaaaaauggg gggc                                                    14

<210> SEQ ID NO 9
<211> LENGTH: 36
<212> TYPE: DNA
<213> ORGANISM: artificial sequence
<220> FEATURE:
<221> NAME/KEY: misc_feature
<223> OTHER INFORMATION: 7G7A oligonucleotide template

<400> SEQUENCE: 9
attctttgct tcttattctt tgcttcttat tctttg                            36
```

METHODS AND APPARATUS FOR ANALYZING POLYNUCLEOTIDE SEQUENCES BY ASYNCHRONOUS BASE EXTENSION

CROSS-REFERENCES TO RELATED APPLICATIONS

This nonprovisional patent application claims the benefit of U.S. Provisional Patent Application No. 60/275,232, filed Mar. 12, 2001, the disclosure of which is hereby incorporated by reference in its entirety and for all purposes.

STATEMENT AS TO RIGHTS TO INVENTIONS MADE UNDER FEDERALLY SPONSORED RESEARCH AND DEVELOPMENT

Work described herein has been supported, in part, by National Institutes of Health Grant HG 01642-04. The U.S. Government may therefore have certain rights in the invention.

TECHNICAL FIELD

The present invention relates to novel methods and apparatus for analyzing polynucleotide sequences with high sensitivity and parallelism.

BACKGROUND OF THE INVENTION

Methods for analyzing polynucleotide sequences can be grouped to two major fields: electrophoretic and non-electrophoretic methods. The electrophoretic methods include slab gel electrophoresis, capillary electrophoresis, microfabricated capillary arrays, and free solution electrophoresis. All these methods rely on the Sanger method in which polynucleotide chain elongation inhibitors are incorporated into the polynucleotide strands which are then separated according to their sizes, usually on a polyacrylamide gel. These methods are the common means for analyzing polynucleotide sequences nowadays. However, the process is time-consuming, requires large amount of target polynucleotides and reaction reagents, and has limited ability to read long sequences that are inherent in the gel electrophoresis methods. The non-electrophoretic methods include pyrosequencing, sequencing by hybridization, massively parallel signature sequencing, and sequencing by mass spectrometry. These methods also have a number of disadvantages. For example, they usually require synchronization of the polynucleotide templates which inevitably decay with each cycle of sequencing reaction.

Thus, there is a need in the art for better methods for analyzing polynucleotide sequences, e.g., methods with high throughput, parallelism, and resolution. The present invention fulfills this and other needs.

SUMMARY OF THE INVENTION

In one aspect, the present invention provides methods for analyzing the sequence of a target polynucleotide. The methods include the steps of (a) providing a primed target polynucleotide immobilized to a surface of a substrate; wherein the target polynucleotide is attached to the surface with single molecule resolution; (b) In the presence of a polymerase, adding a first fluorescently labeled nucleotide to the surface of the substrate under conditions whereby the first nucleotide attaches to the primer, if a complementary nucleotide is present to serve as template in the target polynucleotide; (c) determining presence or absence of a fluorescence signal on the surface where the target polynucleotide is immobilized, the presence of a signal indicating that the first nucleotide was incorporated into the primer, and hence the identity of the complementary base that served as a template in the target polynucleotide; and (d) repeating steps (b)-(c) with a further fluorescently labeled nucleotide, the same or different from the first nucleotide, whereby the further nucleotide attaches to the primer or a nucleotide previously incorporated into the primer.

In some methods, a plurality of different primed target polynucleotides are immobilized to different portions of the substrate. In some methods, steps (b)-(c) are performed at least four times with four different types of labeled nucleotides. In some methods, steps (b)-(c) are performed until the identity of each base in the target polynucleotide has been identified. In some methods, there is an additional step of removing the signal after step (c). In some methods, all ingredients are present simultaneously and a continues monitoring of the incorporation is facilitated.

In some methods of the invention, the presence or absence of a fluorescence signal is determined with total internal reflection fluorescence (TIRF) microscopy. In some methods, the target polynucleotide is primed with a fluorescently labeled primer (e.g., with Cy5 or Cy3). Some methods of the invention employ nucleotides that are labeled with Cy3 or Cy5.

Various materials can be used to immobilize the target polynucleotides. In some methods, a fused silica or glass slide is used. In some methods, the substrate surface is coated with a polyelectrolyte multilayer (PEM). The PEM can be terminated with a polyanion, which helps to repel nucleotides from the surface and reduce non-specific binding to the surface. The polyanion can bear pendant carboxylic acid groups. In some of these methods, the target polynucleotide is biotinylated, and the substrate surface is coated with streptavidin. Often the surface is coated with biotin prior to coating with streptavidin. In some methods, the surface is coated with a polyelectrolyte multilayer (PEM) terminated with carboxylic acid groups prior to attachment of biotin.

In some methods of the invention, a light source for illuminating the surface of said substrate and a detection system for detecting a signal from said surface are employed. Optionally, an appropriately programmed computer is also employed for recording identity of a nucleotide when the nucleotide becomes incorporated into the immobilized primer.

In another aspect, the invention provides apparatus for carrying out the methods of the invention. Typically, the apparatus contain (a) a flow cell which houses a substrate for immobilizing target polynucleotide(s) with single molecule resolution; (b) an inlet port and an outlet port in fluid communication with the flow cell for flowing fluids into and through the flow cell; (c) a light source for illuminating the surface of the substrate; and (d) a detection system for detecting a signal from said surface. Some of the apparatus are microfabricated. In some of these apparatus, the substrate is a microfabricated synthesis channel.

A further understanding of the nature and advantages of the present invention may be realized by reference to the remaining portions of the specification, the figures and claims.

All publications, patents, and patent applications cited herein are hereby expressly incorporated by reference in

DETAILED DESCRIPTION

I. Overview

Figure 1:
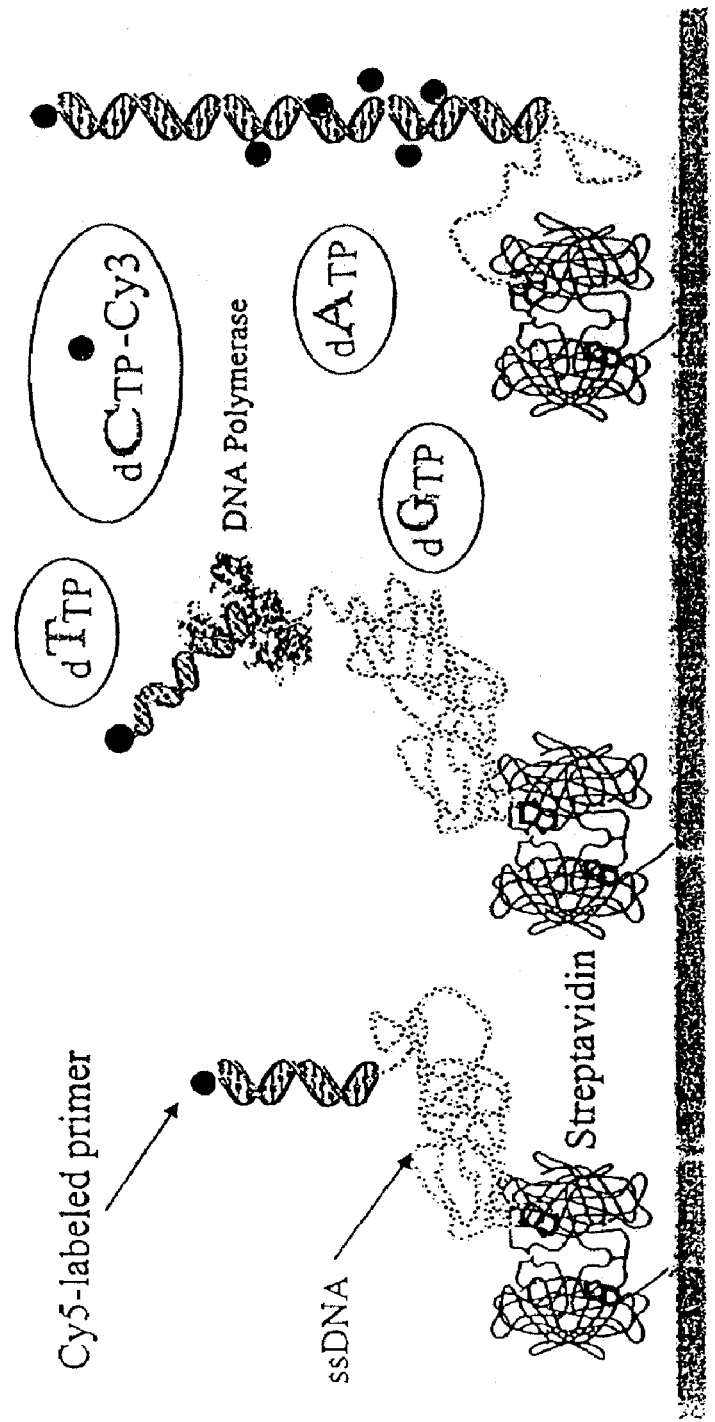
FIG. 1 shows schematically immobilization of a primed polynucleotide and incorporation of labeled nucleotides.

The present invention provides methods and apparatus for analyzing polynucleotides with high sensitivity, parallelism, and long read frames. The invention is predicated in part on visualization of incorporation of labeled nucleotides into immobilized polynucleotide template molecules in a time resolved manner with single molecule resolution. As each of the immobilized template molecules is read individually, no synchronization is needed between the different molecules. Instead, with methods of the present invention, asynchronous base extension is sufficient for analyzing a target polynucleotide sequence.

In some aspects of the invention, single molecule resolution was achieved by immobilizing the template molecules at very low concentration to a surface of a substrate, coating the surface to create surface chemistry that facilitates template attachment and reduces background noise, and imaging nucleotide incorporation with total internal reflection fluorescence microscopy. Analysis with single molecule resolution provides the advantage of monitoring the individual properties of different molecules. It allows identification of properties of an individual molecule that can not be revealed by bulk measurements in which a large number of molecules are measured together. Furthermore, to determine kinetics, bulk measurements require synchronization of the molecules or system state, while in single molecule analysis there is no need for synchronization.

The polynucleotides suitable for analysis with the invention can be DNA or RNA. The analysis can be for sequence analysis, DNA fingerprinting, polymorphism identification, or gene expression measurement. The methods can also be used to analyze activities of other biomacromolecules such as RNA translation and protein assembly. In a preferred embodiment, the method entails immobilization of primed polynucleotide templates to the surface of a solid substrate (e.g., a glass slide). The templates are pre-hybridized to a labeled primer (e.g., with a fluorescent dye) so that their location on the surface can be imaged with single molecule sensitivity. An evanescent light field is set up at the surface in order to image the fluorescently labeled polynucleotide molecules. The evanescent field is also used to image fluorescently labeled nucleotide triphosphates (dNTPs or NTPs) upon their incorporation into the immobilized primer when a polymerase is present.

Methods of the present invention find various applications in polynucleotide sequence analysis. In some applications, a static approach is employed. Such an approach involves adding just one type of labeled nucleotide to the extension reaction at any given time. The signal is incorporated into the primer if the next template residue in the target polynucleotide is the complementary type. Otherwise, a different type of labeled nucleotide is used until the correct residue is incorporated. In other applications, a dynamic approach is employed. In these methods, all four types of nucleotides (at least one type labeled) are simultaneously present in the reaction, and incorporation of the signals into the primer is monitored dynamically. For example, incorporated signals are imaged continuously, preferably at a rate faster than the rate at which the nucleotides are incorporated into the primer.

Preferably, visualization of the templates or incorporated nucleotides are realized with total internal reflection (TIR) fluorescence microscopy. With TIR technology, the excitation light (e.g., a laser beam) illuminates only a small volume of liquid close to the substrate (excitation zone). Signals from free nucleotides in solution that are not present in the excitation zone are not detected. Signals from free nucleotides that diffuse into the excitation zone appear as a broad band background because the free nucleotides move quickly across the excitation zone. Optionally, the fluorescence signals are removed by photobleaching or by chemical means after one or more rounds of incorporation. The methods can also employ microfluidic means to control flow of reaction reagents. In such methods, labeled nucleotides and other reaction reagents can be exchanged in a fast and economic way.

Further, employing a microfluidic device which allows fast fluid exchange, concentrations of nucleotides and/or other reaction reagents can be alternated at different time points of the analysis. This could lead to increased incorporation rate and sensitivity of the analysis. For example, when all four types of nucleotides are simultaneously present in the reaction to monitor dynamic incorporation of nucleotides, concentrations of the nucleotides can be alternated between μM range and sub-nM range. This leads to both better visualization of the signals when low concentrations of nucleotides are present, and increased polymerization rate when higher concentrations of nucleotides are present. Using a microfluidic device, the rate at which the concentrations can be alternated can be as high as a few tens of Hertz. Alternating concentrations of nucleotides is also beneficial to improving signal visualization and polymerization rate in the static approach of sequence analysis. In this approach, after adding a given type of labeled nucleotide to the immobilized template/primer complex and sufficient time for incorporation, free nucleotides (as well as other reaction reagents in solution) can be flown out using a microfluidic device. This will leave a much lower concentration of free nucleotide when the signals are visualized. Optionally, an additional washing step can be employed to further reduce the free nucleotide concentration before the signals are imaged.

In some methods, polynucleotide sequence analysis is accomplished by using four different fluorescent labels on the four nucleotide triphosphates. Incorporated signals are imaged and then photobleached before the next incorporation cycle. Runs of identical bases (e.g., AAAAA) can be identified by, e.g., monitoring the intensity of the signal so that the number of fluorophores at the emitting spot can be determined. Further, signals due to fluorescence resonance energy transfer (FRET) can be detected from individual DNA strands when two different type of fluorescent dyes are incorporated into the same DNA. Such signals are useful to determine sequence information of the immobilized template polynucleotide.

Thus, in some methods, multiple types of labeled nucleotides (e.g., 2 to 4 types each labeled with a different fluorescent dye) can be added at the same time for the extension reactions. In some methods, one type of labeled nucleotide is added at a step, and each extension cycle may comprise four such steps in order to observe the incorporation of a complementary nucleotide. In some methods, less than all four dNTPs are labeled. For example, the analysis can have only two of the nucleotides labeled. By repeating the experiment with different pairs (e.g., AT, AG, AC, TG, TC, GC), the original nucleotide sequence can be delineated. In some methods, the incorporation/extension reaction is performed with multiple copies of the template polynucleotide. Alternatively, one immobilized template molecule can be used repeatedly, by denaturing the extended molecule, removing the newly synthesized strand, annealing a new primer, and then repeating the experiment in situ with fresh reagents.

The present invention is also useful to obtain partial sequence information of a target polynucleotide, e.g., by using only two or three labeled nucleotide species. The relative positions of two or three nucleotide species in the sequence in conjunction with known sequence databases can facilitate determination of the identity of the target sequence, i.e., whether it is identical or related to a known sequence. Such an approach is useful, for example, in determining gene expressions by sequencing cDNA libraries.

The present methods avoid many of the problems observed with the prior art sequencing methods. For example, the methods are highly parallel since many molecules are analyzed simultaneously and in high density (e.g., one template molecule per ~10 $\mu m^2$, of surface area). Thus, many different polynucleotides can be sequenced or genotyped on a single substrate surface simultaneously. In addition, stepwise addition of nucleotides is unnecessary in some methods, as all four nucleotides can be added simultaneously. Rather, sequence information is produced continuously as polymerases continually incorporate all four nucleotides into growing polynucleotide chains. The methods are also extremely sensitive because information obtained from only a single copy of the template molecule is needed in order to determine its sequence. Releasing the extension product from the polynucleotide template, e.g., by denaturing and annealing the template with a different primer provides the opportunity to read again the same template molecule with different sets of nucleotides (e.g., different combinations of two types of labeled nucleotide and two types of unlabeled nucleotides).

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. The following definitions are provided to assist the reader in the practice of the invention.

"Array" refers to a solid support having more than one site or location having either a target polynucleotide or a polymerase bound thereto.

A "base" or "base-type" refers to a particular type of nucleoside base. Typical bases include adenine, cytosine, guanine, uracil, or thymine bases where the type refers to the subpopulation of nucleotides having that base within a population of nucleotide triphosphates bearing different bases. Other rarer bases or analogs can be substituted such as xanthine or hypoxanthine or methylated cytosine.

"Complements a region of the target nucleic acid downstream of the region to be sequenced" in the context of sequencing or genotyping refers to the fact that the primers are extended in a 3' direction by a polymerase. Therefore the primer binds to a subsequence of the target 3' (downstream) to the target sequence that is to be determined as the 3' end of the primer is extended.

"Genotyping" is a determination of allelic content of a target polynucleotide without necessarily determining the sequence content of the entire polynucleotide. It is a subset of sequencing. For example the identification of single nucleotide polymorphisms by determination of single base differences between two known forms of an allele is a form of sequencing that does not require all the target polynucleotide to be sequenced.

"Immobilizing" refers to the attachment of a target nucleic acid or polymerase to a solid support by a means that prevents its release in a reaction solution. The means can be covalent bonding or ionic bonding or hydrophobic bonding.

"Nucleoside" includes natural nucleosides, including ribonucleosides and 2'-deoxyribonucleosides, as well as nucleoside analogs having modified bases or sugar backbones.

The terms "nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides. Unless otherwise noted, "nucleic acid" and "polynucleotide" are used interchangeably.

"Oligonucleotide" or "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptide-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100 kb). ( . . . if a whole chromosome is targeted . . . Thought 100 kb will be already nice . . . ) ["e.g." means it is not exclusive. Also, "100 Mb" probably does not make practical sense]

"Optical reader" or "detection system" refers to a device that can detect and record light emitted from the labeled dNTP (or NTP) or immobilized polynucleotide template (and/or primer) molecules.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature, buffer and pH). The primer is preferably single stranded for maximum efficiency in amplification, but can alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers depend on many factors, including temperature, source of primer and the use of the method.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment can be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer. The use of random primer is used in some cases. For example, when the terminal sequence of the target or template polynucleotide is not known, random primer combinations can be used.

The term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe can be single-stranded or double-stranded. Probes are useful in the detection, identification and isolation of particular gene sequences. It is contemplated that any probe used in the present invention can be labeled with any "reporter molecule," so that is detectable in any detection system, including, but not limited to fluorescent, enzyme (e.g., ELISA, as well as enzyme-based histochemical assays), radioactive, quantum dots, and luminescent systems. It is not intended that the present invention be limited to any particular detection system or label.

"Sequencing" refers to the determination of the order and position of bases in a polynucleotide molecule.

"Single molecule configuration" refers to an array of molecules on a solid support where members of the array are present as an individual molecule located in a defined location. The members can be the same or different.

"Single molecule resolution" refers to the ability of a system to resolve one molecule from another. For example, in far field optical system the detection limit is in the order of a micron. This implies that the distance between two identical molecules to be resolved is at least few microns apart.

"Specific hybridization" refers to the binding, duplexing, or hybridizing of a molecule only to a particular nucleotide sequence under stringent conditions. Stringent conditions are conditions under which a probe can hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide or tetraalkyl ammonium salts. For example, conditions of 5×SSPE (750 mM NaCl, 50 mM Na Phosphate, 5 mM EDTA, pH 7.4) and a temperature of 25-30° C. are suitable for allele-specific probe hybridizations. (See Sambrook et al., *Molecular Cloning* 2001).

The term "template" or "target" refers to a polynucleotide of which the sequence is to be analyzed. In some cases "template" is sought to be sorted out from other polynucleotide sequences. "Substantially single-stranded template" is polynucleotide that is either completely single-stranded (having no double-stranded areas) or single-stranded except for a proportionately small area of double-stranded polynucleotide (such as the area defined by a hybridized primer or the area defined by intramolecular bonding). "Substantially double-stranded template" is polynucleotide that is either completely double-stranded (having no single-stranded region) or double-stranded except for a proportionately small area of single-stranded polynucleotide.

III. Template Preparation and Immobilization

A. Introduction

This invention provides novel methods and apparatus to analyze polynucleotide sequences (e.g., sequencing and genotyping). Preferably, the target or template polynucleotide to be analyzed is immobilized to the surface of a solid substrate (e.g., a fused silica slide) at single molecule resolution. Preferably, the polynucleotide is pre-hybridized to a labeled primer. A DNA or RNA polymerase, four different types of nucleotide triphosphates (NTPs or dNTPs, depending on the template and polymerase used), and other reaction reagents are then applied to the immobilized polynucleotide. At least one type of the nucleotides are fluorescently labeled. When more than one type of NTPs are labeled, the labels are preferably different for different NTPs. Using TIR fluorescent microscopy, incorporation of the labeled nucleotide into a target or template polynucleotide is detected by imaging fluorescence signal from the immobilized polynucleotide with single molecule resolution. Preferably, all four labeled NTPs are present simultaneously. As the polymerase continues to move along the target polynucleotide, the polynucleotide sequence is read from the order of the incorporated labels.

B. Target or Template Polynucleotide

The target polynucleotide is not critical and can come from a variety of standard sources. It can be mRNA, ribosomal RNA, genomic DNA or cDNA. They can comprise naturally occurring and or non-naturally occurring nucleotides. Templates suitable for analysis according to the present invention can have various sizes. For example, the template can have a length of 100 bp, 200 bp, 500 bp, 1 kb, 3 kb, 10 kb, or 20 kb and so on. When the target is from a biological source, there are a variety of known procedures for extracting polynucleotide and optionally amplified to a concentration convenient for genotyping or sequence work. Polynucleotide can be obtained from any living cell of a person, animal or plant. Humans, pathogenic microbes and viruses are particularly interesting sources.

Polynucleotide amplification methods are known in the art. Preferably, the amplification is carried out by polymerase chain reaction (PCR). See, U.S. Pat. Nos. 4,683,202. 4,683,195 and 4,889,818; Gyllenstein et al., 1988, Proc. Natl. Acad. Sci. USA 85: 7652-7656; Ochman et al., 1988, Genetics 120: 621-623; Loh et al., 1989, Science 243: 217-220; Innis et al., 1990, PCR Protocols, Academic Press, Inc., San Diego, Calif. Other amplification methods known in the art that can be used in the present invention include ligase chain reaction (see EP 320,308), or methods disclosed in Kricka et al., 1995, *Molecular Probing, Blotting, and Sequencing,* Chap. 1 and Table IX, Academic Press, New York.

C. Primer Annealing

Primers in combination with polymerases are used to sequence target polynucleotide. Primer length is selected to provide for hybridization to complementary template polynucleotide. The primers will generally be at least 10 bp in length, usually between 15 and 30 bp in length. If part of the template sequence is known, a specific primer can be constructed and hybridized to the template. Alternatively, if sequence of the template is completely unknown, the primers can bind to synthetic oligonucleotide adaptors joined to the ends of target polynucleotide by a ligase.

In some methods, the primer is labeled. When hybridized to the immobilized template, the labeled primer facilitates imaging location of the template. As exemplified in the Examples below, the primer can be labeled with a fluorescent label (e.g., Cy5). Preferably, the label used to label the primer is different from the labels on the nucleotides in the subsequent extension reactions.

The primers can be synthetically made using conventional nucleic acid synthesis technology. For example, the primers can be conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the polymerase. The primers can also be ordered commercially from a variety of companies which specialize in custom oligonucleotides such as Operon Inc (Alameda, Calif.).

Primer annealing is performed under conditions which are stringent enough to achieve sequence specificity yet sufficiently permissive to allow formation of stable hybrids at an acceptable rate. The temperature and length of time required for primer annealing depend upon several factors including the base composition, length and concentration of the primer, and the nature of the solvent used, e.g., the concentration of DMSO, formamide, or glycerol, and counter ions such as magnesium. Typically, hybridization with synthetic polynucleotides is carried out at a temperature that is approximately 5 to 10° C. below the melting temperature of the target-primer hybrid in the annealing solvent. In some methods, the annealing temperature is in the range of 55 to 75° C. and the primer concentration is approximately 0.2 μM. Other conditions of primer annealing are provided in the Examples below. Under these preferred conditions, the annealing reaction can be complete in only a few seconds.

D. Immobilization of Template Polynucleotide

Preferably, the template or target polynucleotide molecules are provided as single molecule arrays immobilized to the surface of a solid substrate. The substrate can be glass, silica, plastic or any other conventionally non-reactive material that will not create significant noise or background for the fluorescent detection methods. Substrate surface to which the template polynucleotides are to be immobilized can also be the internal surface of a flow cell in a microfluidic apparatus, e.g., a microfabricated synthesis channel of the apparatus as described in the PCT application of Quake et al. (WO 01/32930; which is incorporated herein by reference). In some preferred embodiments, the solid support is made from fused silica slide (e.g., a fused silica glass slide from Esco, Cat. R130110). Compared to other support materials (e.g., a regular glass slide), fused silica has very low auto-fluorescence.

In some applications of the present invention, the template or target polynucleotides are immobilized to the substrate surface with single molecule resolution. In such methods, as exemplified in the Examples below, single molecule resolution is achieved by using very low concentration of the polynucleotide in the immobilization reaction. For example, a 10 pM concentration for a 80-mer polynucleotide template allows attachment of the polynucleotide to the surface of a silica slide at single molecule resolution (see Example 1). Template immobilization with single molecule resolution can also be verified by measuring bleach pattern of the fluorescently labeled templates (see Example 5).

In some methods, the templates are hybridized to the primers first and then immobilized to the surface. In some methods, the templates are immobilized to the surface prior to hybridization to the primer. In still some methods, the primers are immobilized to the surface, and the templates are attached to the substrates through hybridization to the primers. In still some methods, the polymerase is immobilized to the surface.

Various methods can be used to immobilize the templates or the primers to the surface of the substrate. The immobilization can be achieved through direct or indirect bonding of the templates to the surface. The bonding can be by covalent linkage. See, Joos et al., Analytical Biochemistry 247:96-101, 1997; Oroskar et al., Clin. Chem 42:1547-1555, 1996; and Khandjian, Mole. Bio. Rep. 11:107-115, 1986. The bonding can also be through non-covalent linkage. For example, Biotin-streptavidin (Taylor et al., *J. Phys. D. Appl. Phys.* 24:1443, 1991) and digoxigenin and anti-digoxigenin (Smith et al., *Science* 253: 1122, 1992) are common tools for attaching polynucleotides to surfaces and parallels. Alternatively, the bonding can be achieved by anchoring a hydrophobic chain into a lipidic monolayer or bilayer. When biotin-streptavidin linkage is used to immobilize the templates, the templates are biotinylated, and one surface of the substrates are coated with streptavidin. Since streptavidin is a tetramer, it has four biotin binding sites per molecule. Thus, it can provide linkage between the surface and the template. In order to coat a surface with streptavidin, the surface can be biotinylated first, and then parts of the four binding sites of streptavidin can be used to anchor the protein to the surface, leaving the other sites free to bind the biotinylated template (see, Taylor et al., *J. Phys. D. Appl Phys.* 24:1443, 1991). Such treatment leads to a high density of streptavidin on the surface of the substrate, allowing a correspondingly high density of template coverage. Surface density of the template molecules can be controlled by adjusting concentration of the template which is applied to the surface. Reagents for biotinylating a surface can be obtained, for example, from Vector laboratories. Alternatively, biotinylation can be performed with BLCPA: EZ-Link Biotin LC-PEO-Amine (Pierce, Cat. 21347).

In some methods, labeled streptavidin (e.g., with a fluorescent label) of very low concentration (e.g., in the $\mu M$, nM or pM range) is used to coat the substrate surface prior to template immobilization. This facilitates immobilization of the template with single molecule resolution. It also allows monitoring of spots on the substrate to which the template molecules are attached, and subsequent nucleotide incorporation events.

While diverse polynucleotide templates can be each immobilized to and sequenced in a separate substrate, multiple templates can also be analyzed on a single substrate. In the latter scenario, the templates are attached at different locations on the substrate. This can be accomplished by a variety of different methods, including hybridization of primer capture sequences to oligonucleotides immobilized at different points on the substrate, and sequential activation of different points down the substrate towards template immobilization.

Methods of creation of surfaces with arrays of oligonucleotides have been described, e.g., in U.S. Pat. Nos. 5,744,305, 5,837,832, and 6,077,674. Primers with two domains, a priming domain and a capture domain, can be used to anchor templates to the substrate. The priming domain is complementary to the target template. The capture domain is present on the non-extended side of the priming sequence. It is not complementary to the target template, but rather to a specific oligonucleotide sequence present on the substrate. The target templates can be separately hybridized with their primers, or (if the priming sequences are different) simultaneously hybridized in the same solution. Incubation of the primer/template duplexes with the substrate under hybridization conditions allows attachment of each template to a unique spot. Multiple substrates can be charged with templates in this fashion simultaneously.

Another method for attaching multiple templates to the surface of a single substrate is to sequentially activate portions of the substrate and attach template to them. Activation of the substrate can be achieved by either optical or electrical means. Optical illumination can be used to initiate a photochemical deprotection reaction that allows attachment of the template to the surface (see, e.g., U.S. Pat. Nos. 5,599,695, 5,831,070, and 5,959,837). For instance, the substrate surface can be derivitized with "caged biotin", a commercially available derivative of biotin that becomes capable of binding to avidin only after being exposed to light. Templates can then be attached by exposure of a site to light, filling the channel with avidin solution, washing, and then flowing biotinylated template into the channel. Another variation is to prepare avidinylated substrate and a template with a primer with a caged biotin moiety; the template can then be immobilized by flowing into the channel and illumination of the solution above a desired area. Activated template/primer duplexes are then attached to the first wall they diffused to, yielding a diffusion limited spot.

Electrical means can also be used to direct template to specific locations on a substrate. By positively charging one electrode in the channel and negatively charging the others, a field gradient can be created which drives the template to a single electrode, where it can attach (see, e.g., U.S. Pat. Nos. 5,632,957, 6,051,380, and 6,071,394). Alternatively, it can be achieved by electrochemically activating regions of the surface and changing the voltage applied to the electrodes. Patterning of particular chemicals, include proteins and DNA is possible with a stamp method, in which a microfabricated plastic stamp is pressed on the surface (see, e.g., Lopez et al., J. Amer. Chem. Soc. 115:10774-81, 1993). Different templates can also be attached to the surface randomly as the reading of each individual is independent from the others.

E. Treatment of Substrate Surface

In some applications, surface of the substrate is pretreated to create surface chemistry that facilitates attachment of the polynucleotide templates and subsequent synthesis reactions. The surface chemistry also reduces the background from non specific attachment of free labeled nucleotide to the surface of the substrate.

In some methods, the surface is coated with a polyelectrolyte multilayer (PEM). In some methods, non-PEM based surface chemistry can be created prior to template attachment. Preferably, the substrate surface is coated with a polyelectrolyte multilayer (PEM). Attachment of templates to PEM-coated surface can be accomplished by light-directed spatial attachment (see, e.g., U.S. Pat. Nos. 5,599, 695, 5,831,070, and 5,959,837). Alternatively, the templates can be attached to PEM-coated surface entire chemically (see below for detail).

PEM formation has been described in Decher et al. (Thin Solid Films, 210:831-835, 1992). PEM formation proceeds by the sequential addition of polycations and polyanions, which are polymers with many positive or negative charges, respectively. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to poly(+) and poly(−) generates a polyelectrolyte multilayer structure with a surface charge determined by the last polyelectrolyte added; in the case of incompletely-charged surfaces, multiple-layer deposition also tends to increase surface charge to a well defined and stable level.

An exemplified scheme of coating a substrate with PEM for immobilizing polynucleotide is provided in PCT publication WO 01/32930. Detailed procedures are also disclosed in the Examples below. Briefly, the surface of the substrate (e.g., a glass cover slip) is cleaned with a RCA solution. After cleaning, the substrate is coated with a polyelectrolyte multilayer (PEM). Following biotinylation of the carboxylic acid groups, streptavidin is then applied to generate a surface capable of capturing biotinylated molecules. Biotinylated polynucleotide templates are then added to the coated glass cover slip for attachment. The surface chemistry thus created provides various advantages for the methods of the present invention, because it generates a strong negatively-charged surface which repels the negatively-charged nucleotides. First, a polyelectrolyte multilayer terminated with carboxylic acid-bearing polymer is easy to attach polynucleotide to because carboxylic acids are good targets for covalent bond formation. In addition, the attached template is active for extension by polymerases—most probably, the repulsion of like charges prevents the template from "laying down" on the surface. Finally, the negative charge repels the fluorescent nucleotides, and nonspecific binding is low.

The attachment scheme described here is easy to generalize on. Without modification, the PEM/biotin/streptavidin surface that is produced can be used to capture or immobilize any biotinylated molecule. A slight modification can be the use of another capture pair, e.g., substituting digoxygenin (dig) for biotin and labeling the molecule to be immobilized with anti-digoxygenin (anti-dig). Reagents for biotinylation or dig-labeling of amines are all commercially available.

Another generalization is that the chemistry is nearly independent of the surface chemistry of the support. Glass, for instance, can support PEMs terminated with either positive or negative polymer, and a wide variety of chemistry for either. But other substrates such as silicone, polystyrene, polycarbonate, etc, which are not as strongly charged as glass, can still support PEMs. The charge of the final layer of PEMs on weakly-charged surfaces becomes as high as that of PEMs on strongly-charged surfaces, as long as the PEM has sufficiently-many layers. This means that all the advantages of the glass/PEM/biotin/Streptavidin/biotin-DNA surface chemistry can be applied to other substrates.

IV. Primer Extension Reaction

Once templates are immobilized to the surface of a substrate, primer extension reactions are performed, e.g., as described in Sambrook, supra; Ausubel, supra; and Hyman, Anal. Biochem., 174, p. 423, 1988. In some methods; the primer is extended by a polynucleotide polymerase in the presence of a single type of labeled nucleotide. In other methods, all four types of differently labeled nucleotides are present. In some applications of the present invention, a combination of labeled and non-labeled nucleotides are used in the analysis. A label is incorporated into the template/primer complex only if the specific labeled nucleotide added to the reaction is complementary to the nucleotide on the template adjacent the 3' end of the primer. Optionally, the template is subsequently washed to remove any unincorporated label, and the presence of any incorporated label is determined. As some errors can be caused by the polymerase, the reaction conditions and incubation time should minimize these errors.

A. Labeled Nucleotides

To facilitate detection of nucleotide incorporation, at least one and usually all types of the deoxyribonucleotides (dATP, dTTP, dGTP, dCTP, dUTP/dTTP) or nucleotides (ATP, UTP, GTP, and CTP) are labeled with fluorophores. When more than one type of nucleotides are labeled, a different kind of label can be used to label each different type of nucleotide. However, in some applications, the different types of nucleotides can be labeled with the same kind of labels.

Various fluorescent labels can be used to label the nucleotides in the present invention. The fluorescent label can be selected from any of a number of different moieties. The preferred moiety is a fluorescent group for which detection is quite sensitive. The affinity to the surface could be changed between different dyes. Low affinity to the surface is preferred. For example, Cy3 and Cy5 are used to label the primer or nucleotides in some methods of the invention. However, Cy5 has higher affinity to the surface under certain experimental condition than Cy3.

Other factors that need to be considered include stability of the dyes. For example, Cy5 is less stable and tends to bleach faster than Cy3. Such property can be of advantage or disadvantage, depending on the circumstances. In addition, different sizes of the dyes can also affect efficiency of incorporation of labeled nucleotides. Further, length of the linker between the dye and the nucleotide can impact efficiency of the incorporation (see, Zhu and Waggoner, Cytometry 28: 206, 1997).

An exemplary list of fluorophores, with their corresponding absorption/emission wavelength indicated in parenthesis, that can be used in the present invention include Cy3 (550/565), Cy5 (650/664), Cy7 (750/770), Rho123 (507/529), R6G (528/551), BODIPY 576/589 (576/589), BODIPY TR (588/616), Nile Blue (627/660), BODIPY 650/665 (650/665), Sulfo-IRD700 (680/705), NN382 (778/806), Alexa488 (490/520), Tetramethylrhodamine (550/570). and Rodamine X (575/605).

The fluorescently labeled nucleotides can be obtained commercially (e.g., from NEN DuPont, Amersham, or BDL). Alternatively, fluorescently labeled nucleotides can also be produced by various fluorescence-labeling techniques, e.g., as described in Kambara et al. (1988) "Optimization of Parameters in a DNA Sequenator Using Fluorescence Detection," Bio/Technol. 6:816-821; Smith et al. (1985) Nucl. Acids Res, 13:2399-2412; and Smith et al. (1986) Nature 321:674-679. Acyl fluoride of Cy5 cyanine dye can also be synthesized and labeled as described in U.S. Pat. No. 6,342,326.

There is a great deal of practical guidance available in the literature for providing an exhaustive list of fluorescent and chromogenic molecules and their relevant optical properties (see, for example, Berlman, *Handbook of Fluorescence Spectra of Aromatic Molecules,* 2nd Edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes and Research Chemicals* (Molecular Probes, Eugene, 1992) Pringsheim,

*Fluorescence and Phosphorescence* (Interscience Publishers, New York, 1949); and the like. Further, there is extensive guidance in the literature for derivatizing fluorophore and quencher molecules for covalent attachment via common reactive groups that can be added to a nucleotide, as exemplified by the following references: Haugland (supra); Ullman et al., U.S. Pat. No. 3,996,345; Khanna et al., U.S. Pat. No. 4,351,760.

There are many linking moieties and methodologies for attaching fluorophore moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305-5321 (1987) (3' thiol group on oligonucleotide); Sharma et al., *Nucleic Acids Research*, 19: 3019 (1991) (3' sulfhydryl); Giusti et al., *PCR Methods and Applications*, 2: 223-227 (1993) and Fung et al., U.S. Pat. No. 4,757,141 (5' phosphoamino group via Aminolink™. II available from Applied Biosystems, Foster City, Calif.) Stabinsky, U.S. Pat. No. 4,739,044 (3' aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5' mercapto group); Nelson et al., *Nucleic Acids Research*, 17: 7187-7194 (1989) (3' amino group); and the like.

In instances where a multi-labeling scheme is utilized, a wavelength which approximates the mean of the various candidate labels' absorption maxima may be used. Alternatively, multiple excitations may be performed, each using a wavelength corresponding to the absorption maximum of a specific label.

B. Other Reaction Reagents

1. Polymerases

Many polymerases can be selected for use in this invention. Preferred polymerases are able to tolerate labels on the nucleobase. For example, some applications of the present invention employ polymerases that have increased ability to incorporate modified, fluorophore-labeled, nucleotides into polynucleotides. Examples of such polymerases, e.g., mutant bacteriophage T4 DNA polymerases, have been described in U.S. Pat. No. 5,945,312.

Depending on the template, either RNA polymerase, DNA polymerases or reverse transcriptase can be used in the primer extension. For analysis of DNA templates, many DNA polymerases are available. Examples of suitable DNA polymerases include, but are not limited to, Sequenase 2.0.RTM., T4 DNA polymerase or the Klenow fragment of DNA polymerase 1, or Vent polymerase. In some methods, polymerases which lack 3'→5' exonuclease activity can be used (e.g., T7 DNA polymerase (Amersham) or Klenow— exo fragment of DNA polymerase I (New England Biolabs)). In some methods, when it is desired that the polymerase have proof-reading activity, polymerases lacking 3'→5' exonuclease activity are not used. In some methods, thermostable polymerases such as ThermoSequenase™ (Amersham) or Taquenase™ (ScienTech, St Louis, Mo.) are used.

In general, the polymerase should have a fidelity (incorporation accuracy) of at least 99% and a processivity (number of nucleotides incorporated before the enzyme dissociates from the DNA) of at least 20 nucleotides, with greater processivity preferred. Examples include T7 DNA polymerase, T5 DNA polymerase, HIV reverse transcriptase, *E. coli* DNA pol I, T4 DNA polymerase, T7 RNA polymerase, Taq DNA polymerase and *E. coli* RNA polymerase, Phi29 DNA polymerase.

The nucleotides used in the methods should be compatible with the selected polymerase. Procedures for selecting suitable nucleotide and polymerase combinations can be adapted from Ruth et al. (1981) Molecular Pharmacology 20:415-422; Kutateladze, T., et al. (1984) Nuc. Acids Res., 12:1671-1686; Chidgeavadze, Z., et al. (1985) FEBS Letters, 183:275-278.

The polymerase can be stored in a separate reservoir and flowed onto the substrates (or into a flow chamber/cell which houses the substrate) prior to each extension reaction cycle. The enzyme can also be stored together with the other reaction agents (e.g., the nucleotide triphosphates). Alternatively, the polymerase can be immobilized onto the surface of the substrate while the polynucleotide template is added to the solution.

2. Blocking Agents

In some methods, it may be desirable to employ a chain elongation inhibitor in the primer extension reaction (see, e.g., Dower et al., U.S. Pat. No. 5,902,723). Chain elongation inhibitors are nucleotide analogues which either are chain terminators which prevent further addition by the polymerase of nucleotides to the 3' end of the chain by becoming incorporated into the chain themselves. In some methods, the chain elongation inhibitors are dideoxynucleotides. Where the chain elongation inhibitors are incorporated into the growing polynucleotide chain, they should be removed after incorporation of the labeled nucleotide has been detected, in order to allow the sequencing reaction to proceed using different labeled nucleotides. Some 3' to 5' exonucleases, e.g., exonuclease III, are able to remove dideoxynucleotides.

Other than chain elongation inhibitors, a blocking agent or blocking group can be employed on the 3' moiety of the deoxyribose group of the labeled nucleotide to prevent nonspecific incorporation. Optimally, the blocking agent should be removable under mild conditions (e.g., photosensitive, weak acid labile, or weak base labile groups), thereby allowing for further elongation of the primer strand with a next synthetic cycle. If the blocking agent also contains the fluorescent label, the dual blocking and labeling functions are achieved without the need for separate reactions for the separate moieties. For example, the labeled nucleotide can be labeled by attachment of a fluorescent dye group to the 3' moiety of the deoxyribose group, and the label is removed by cleaving the fluorescent dye from the nucleotide to generate a 3' hydroxyl group. The fluorescent dye is preferably linked to the deoxyribose by a linker arm which is easily cleaved by chemical or enzymatic means.

Examples of blocking agents include, among others, light sensitive groups such as 6-nitoveratryloxycarbonyl (NVOC), 2-nitobenzyloxycarbonyl (NBOC), .α,.α-dimethyl-dimethoxybenzyloxycarbonyl (DDZ), 5-bromo-7-nitroindolinyl, o-hydroxy-2-methyl cinnamoyl, 2-oxymethylene anthraquinone, and t-butyl oxycarbonyl (TBOC). Other blocking reagents are discussed, e.g., in U.S. Ser. No. 07/492,462; Patchornik (1970) J. Amer. Chem. Soc. 92:6333; and Amit et al. (1974) J. Org. Chem. 39:192. Nucleotides possessing various labels and blocking groups can be readily synthesized. Labeling moieties are attached at appropriate sites on the nucleotide using chemistry and conditions as described, e.g., in Gait (1984) Oligonucleotide Synthesis: A Practical Approach, IRL Press, Oxford.

C. Reaction Conditions

The reaction mixture for the sequencing comprises an aqueous buffer medium which is optimized for the particular polymerase. In general, the buffer includes a source of monovalent ions, a source of divalent cations and a buffering agent. Any convenient source of monovalent ions, such as KCl, K-acetate, NH$_4$-acetate, K-glutamate, NH$_4$Cl, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micromhos.

The divalent cation may be magnesium, manganese, zinc and the like, where the cation will typically be magnesium. Any convenient source of magnesium cation may be employed, including MgCl$_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

D. Removal of Labels and Blocking Group

By repeating the incorporation and label detection steps until incorporation is detected, the nucleotide on the template adjacent the 3' end of the primer can be identified. Once this has been achieved, the label should be removed before repeating the process to discover the identity of the next nucleotide. Removal of the label can be effected by removal of the labeled nucleotide using a 3'-5' exonuclease and subsequent replacement with an unlabeled nucleotide. Alternatively, the labeling group can be removed from the nucleotide. Release of the fluorescence dye can be achieved if a detachable connection between the nucleotide and the fluorescence molecule is used. For example, the use of disulfide bonds enables one to disconnect the dye by applying a reducing agent like dithiothreitol (DTT). In a further alternative, where the label is a fluorescent label, it is possible to neutralize the label by bleaching it with radiation. Photobleaching can be performed according to methods, e.g., as described in Jacobson et al., "International Workshop on the Application of Fluorescence Photobleaching Techniques to Problems in Cell Biology", Federation Proceedings, 42:72-79, 1973; Okabe et al., J Cell Biol 120:1177-86, 1993; Wedekind et al., J Microsc. 176 Pt 1): 23-33, 1994; and Close et al., Radiat Res 53:349-57, 1973.

If chain terminators or 3' blocking groups have been used, these should be removed before the next cycle can take place. 3' blocking groups can be removed by chemical or enzymatic cleavage of the blocking group from the nucleotide. For example, chain terminators are removed with a 3'-5' exonuclease, e.g., exonuclease III. Once the label and terminators/blocking groups have been removed, the cycle is repeated to discover the identity of the next nucleotide.

E. Sample Housing

The solid substrate is optionally housed in a flow chamber having an inlet and outlet to allow for renewal of reactants which flow past the immobilized moieties. The flow chamber can be made of plastic or glass and should either be open or transparent in the plane viewed by the microscope or optical reader. Electro-osmotic flow requires a fixed charge on the solid substrate and a voltage gradient (current) passing between two electrodes placed at opposing ends of the solid support. Pressure driven flow can be facilitated by microfluidic device with an external pressure source or by microfluidic peristaltic pump (see, e.g., Unger et al., Science 288: 113-116, 2000).

The flow chamber can be divided into multiple channels for separate sequencing. Examples of micro flow chambers are described in Fu et al. (Nat. Biotechnol. (1999) 17:1109) which describe a microfabricated fluorescence-activated cell sorter with 3 μm×4 μm channels that utilizes electro-osmotic flow for sorting. Preferably, the flow chamber contains microfabricated synthesis channels as described in WO01/32930. The polynucleotide templates can be immobilized to the surface of the synthesis channels. These synthesis channels can be in fluid communication with a microfluidic device which controls flow of reaction reagents. Preferred microfluidic devices that can be employed to control flow of reaction reagents in the present invention have been described in WO01/32930.

The present invention also provide apparatus for carrying out the methods of the invention. Other than the substrate to which the target polynucleotides or primers are attached, the apparatus usually comprise a flow chamber in which the substrate is housed. In addition, the apparatus can optionally contain plumbing devices (e.g., an inlet and an outlet port), a light source, and a detection system described herein. Preferably, a microfabricated apparatus as described in WO01/32930 is adapted to house the substrate of the present invention.

V. Detection of Incorporated Signals

A. Detection System in General

Methods for visualizing single molecules of DNA labeled with an intercalating dye include, e.g., fluorescence microscopy as described in Houseal et al., Biophysical Journal 56: 507, 1989. While usually signals from a plurality of molecules are to be detected with the sequencing methods of the present invention, fluorescence from single fluorescent dye molecules can also be detected. For example, a number of methods are available for this purpose (see, e.g., Nie et al., Science 266: 1013, 1994; Funatsu et al., Nature 374: 555, 1995; Mertz et al., Optics Letters 20: 2532, 1995; and Unger et al., Biotechniques 27:1008, 1999). Even the fluorescent spectrum and lifetime of a single molecule excited-state can be measured (Macklin et al., Science 272: 255, 1996). Standard detectors such as a photomultiplier tube or avalanche photodiode can be used. Full field imaging with a two stage image intensified CCD camera can also used (Funatsu et al., supra). Low noise cooled CCD can also be used to detect single fluorescence molecules (see, e.g., Unger et al., Biotechniques 27: 1008-1013, 1999; and SenSys spec: http://www.photomet.com/pdfs/datasheets/sensys/ ss1401e.pdf).

The detection system for the signal or label can also depend upon the label used, which can be defined by the chemistry available. For optical signals, a combination of an optical fiber or charged couple device (CCD) can be used in the detection step. In those circumstances where the matrix is itself transparent to the radiation used, it is possible to have an incident light beam pass through the substrate with the detector located opposite the substrate from the polynucleotides. For electromagnetic labels, various forms of spectroscopy systems can be used. Various physical orientations for the detection system are available and discussion of important design parameters is provided in the art (e.g., Arndt-Jovin et al., J Cell Biol 101: 1422-33, 1985; and Marriott et al., Biophys J 60: 1374-87, 1991).

Many applications of the invention require the detection of incorporation of fluorescently labeled nucleotides into single template molecules in a solution. The single-molecule fluorescence detection of the present invention can be practiced using optical setups including near-field scanning microscopy, far-field confocal microscopy, wide-field epi-illumination, and total internal reflection fluorescence (TIRF) microscopy. General reviews are available describing this technology, including, e.g., Basche et. al., eds., 1996, Single molecule optical detection, imaging, and spectroscopy, Weinheim:VCM; and Plakhotnik, et. al., Single-molecule spectroscopy, *Ann. Rev. Phys, Chem.* 48: 181-212. In general, the methods involve detection of laser activated fluorescence using microscope equipped with a camera. It is sometimes referred to as a high-efficiency photon detection system (see, e.g., Nie, et. al., 1994, Probing individual molecules with confocal fluorescence microscopy, *Science* 266:1018-1019. Other suitable detection systems are discussed in the Examples below.

Suitable photon detection systems include, but are not limited to, photodiodes and intensified CCD cameras. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images (movies) of fluorophores. In certain aspects, each of the dNTPs or NTPs employed in the methods has a unique fluorophore associated with it, as such, a four-color instrument can be used having four cameras and four excitation lasers. Preferably the image could be split to four quarters and imaged by a single camera. For example, the micro-imager of Optical Insights LTD is a simple device that splits the image to four different images in four different spectra just in front of the port of the camera. Illumination with only one laser excitation for the four colors is possible if suitable dyes are used (see, e.g., Rosenblum et al, Nucleic Acids Research 25:4500, 1997). For example, the BigDyes have single excitation wavelength spectrum and four different emission wavelength spectrums. They can be obtained from Applied Biosystems (see, http://www.appliedbiosystems.com/products/productdetail.cfm?ID=82). Nanocrystals are also found to have a variety of emission wavelengths for a given excitation (see, e.g., U.S. Pat. No. 6,309,701; and Lacoste et al., Proc. Natl. Acad. Sci. USA 97: 9461-6, 2000). Thus, it is possible to use such optical setup to sequence DNA. In addition, many different DNA molecules spread on a solid support (e.g., a microscope slide) can be imaged and sequenced simultaneously.

B. Total Internal Reflection Fluorescence (TIRF) Microscopy

In some preferred embodiments, the present invention uses total internal reflection fluorescence (TIRF) microscopy for two-dimensional imaging fluorescence detection. TIRF microscopy is well known in the art. See, e.g., Watkins et al., J Biomed Mater Res 11:915-38, 1977; and Axelrod et al., J Microsc, 129:19-28, 1983. TIRF microscopy uses totally internally reflected excitation light. When a laser beam was totally reflected at the interface between a liquid and a solid substrate (e.g., a glass), the excitation light beam penetrates only a short distance into the liquid. In other words, the optical field does not end abruptly at the reflective interface, but its intensity falls off exponentially with distance. This surface electromagnetic field, called the 'evanescent wave', can selectively excite fluorescent molecules in the liquid near the interface. The thin evanescent optical field at the interface provides low background and enables the detection of single molecules with high signal-to-noise ratio at visible wavelengths (see, M. Tokunaga et al., *Biochem. and Biophys. Res. Comm.* 235, 47 (1997) and P. Ambrose, *Cytometry,* 36, 244 (1999)).

TIRF microscopy has been used to examine various molecular or cellular activities, e.g., cell/substrate contact regions of primary cultured rat myotubes with acetylcholine receptors labeled by fluorescent alpha-bungarotoxin, and human skin fibroblasts labeled with a membrane-incorporated fluorescent lipid (see, e.g., Thompson et al., Biophys J. 33:435-54, 1981; Axelrod, J. Cell. Biol. 89: 141-5, 1981; and Burghardt et al., Biochemistry 22:979-85, 1983). TIRF examination of cell/surface contacts dramatically reduces background from surface autofluorescence and debris. TIRF has also been combined with fluorescence photobleaching recovery and correlation spectroscopy to measure the chemical kinetic binding rates and surface diffusion constant of fluorescent labeled serum protein binding (at equilibrium) to a surface (see, e.g., Burghardt et al., Biophys J. 33:455-67, 1981); and Thompson et al., Biophys J, 43:103-14, 1983). Additional examples of TIRR detection of single molecules have been described in Vale et. al., 1996, Direct observation of single kinesin molecules moving along microtubules, *Nature* 380: 451; and Xu et al., 1997, Direct Measurement of Single-Molecule Diffusion and Photodecomposition in Free Solution, *Science* 275: 1106-1109.

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface which corresponds to the contour length of about 600 base pairs of DNA. In some embodiments, when longer polynucleotide templates are analyzed, the polymerase rather than the template is immobilized to the surface so the reaction occurs near the surface at all time. In some embodiments, a prism-type TIRF geometry for single-molecule imaging as described by Xu and Yeung is used (see, X-H.N. Xu et al., *Science,* 281, 1650 (1998)). In some embodiments, an objective type TIRF is used to provide space above the objective so that a microfluidic device can be used (see, e.g., Tokunaga et al., Biochem Biophy Res Commu 235: 47-53, 1997; Ambrose et al., Cytometry 36:224;1999; and Braslavsky et al, Applied Optics 40:5650, 2001).

Total internal reflection can be utilized with high numerical aperture objectives (ranging between 1.4 and 1.65 in aperture), preferentially using an inverted microscope. The numerical aperture of an objective is a function of the max angle that can be collected (or illuminated) with the objective in a given refractive index of the media (i.e., NA=n*sin (tetaMax)). If tetaMax is larger than teta Critic for reflection, some of the illuminated rays will be totally internal reflected. So using the peripheral of a large NA objective one can illuminate the sample with TIR through the objective and use the same objective to collect the fluorescence light. Therefore, the objective plays double roles as a condenser and an imaging objective.

Single molecule detection can be achieved using flow cytometry where flowing samples are passed through a focused laser with a spatial filter used to define a small volume. U.S. Pat. No. 4,979,824 describes a device for this purpose. U.S. Pat. No. 4,793,705 describes a detection system for identifying individual molecules in a flow train of the particles in a flow cell. It further describes methods of arranging a plurality of lasers, filters and detectors for detecting different fluorescent nucleic acid base-specific labels. U.S. Pat. No. 4,962,037 also describes a method for detecting an ordered train of labeled nucleotides for obtaining DNA and RNA sequences using an exonuclease to cleave the bases. Single molecule detection on solid supports is also described in Ishikawa, et al. (1994) Single-molecule detection by laser-induced fluorescence technique with a position-sensitive photon-counting apparatus, *Jan. J Apple. Phys.* 33:1571-1576. Ishikawa describes a typical apparatus involving a photon-counting camera system attached to a fluorescence microscope. Lee et al. (*Anal. Chem.*, 66:4142-4149, 1994) describes an apparatus for detecting single molecules in a quartz capillary tube. The selection of lasers is dependent on the label and the quality of light required. Diode, helium neon, argon ion, argon-krypton mixed ion, and double Nd:YAG lasers are useful in this invention.

C. Excitation and Scanning

In some applications, fluorescent excitation is exerted with a Q-switched frequency doubled Nd YAG laser, which has a KHz repetition rate, allowing many samples to be taken per second. For example, a wavelength of 532 nm is ideal for the excitation of rhodamine. It is a standard device that has been used in the single molecule detection scheme (Smith et al., *Science* 253:1122, 1992). A pulsed laser allows time resolved experiments, which are useful for rejecting extraneous noise. In some methods, excitation can be performed with a mercury lamp and signals from the incorporated nucleotides can be detected with an CCD camera (see, e.g., Unger et al., Biotechniques 27:1008, 1999).

Incorporated signals can be detected by scanning the substrates. The substrates can be scanned simultaneously or serially, depending on the scanning method used. The signals can be scanned using a CCD camera (TE/CCD512SF, Princeton Instruments, Trenton, N.J.) with suitable optics (Ploem, J. S., in Fluorescent and Luminescent Probes for Biological Activity, Mason, T. W., Ed., Academic Press, London, pp. 1-11, 1993), such as described in Yershov et al. (Proc. Natl. Acad. Sci. 93:4913, 1996), or can be imaged by TV monitoring (Khrapko et al., DNA Sequencing 1:375, 1991). The scanning system should be able to reproducibly scan the substrates. Where appropriate, e.g., for a two dimensional substrate where the substrates are localized to positions thereon, the scanning system should positionally define the substrates attached thereon to a reproducible coordinate system. It is important that the positional identification of substrates be repeatable in successive scan steps.

Various scanning systems can be employed in the methods and apparatus of the present invention. For example, electro-optical scanning devices described in, e.g., U.S. Pat. No. 5,143,854, are suitable for use with the present invention. The system could exhibit many of the features of photographic scanners, digitizers or even compact disk reading devices. For example, a model no. PM500-A1 x-y translation table manufactured by Newport Corporation can be attached to a detector unit. The x-y translation table is connected to and controlled by an appropriately programmed digital computer such as an IBM PC/AT or AT compatible computer. The detection system can be a model no. R943-02 photomultiplier tube manufactured by Hamamatsu, attached to a preamplifier, e.g., a model no. SR440 manufactured by Stanford Research Systems, and to a photon counter, e.g., an SR430 manufactured by Stanford Research System, or a multichannel detection device. Although a digital signal can usually be preferred, there can be circumstances where analog signals would be advantageous.

The stability and reproducibility of the positional localization in scanning determine, to a large extent, the resolution for separating closely positioned polynucleotide clusters on a two dimensional substrate. Since the successive monitoring at a given position depends upon the ability to map the results of a reaction cycle to its effect on a positionally mapped polynucleotides, high resolution scanning is preferred. As the resolution increases, the upper limit to the number of possible polynucleotides which can be sequenced on a single matrix also increases. Crude scanning systems can resolve only on the order of 1000 µm, refined scanning systems can resolve on the order of 100 µm, more refined systems can resolve on the order of about 10 µm, and with optical magnification systems a resolution on the order of 1.0 µm is available. The limitations on the resolution can be diffraction limited and advantages can arise from using shorter wavelength radiation for fluorescent scanning steps. However, with increased resolution, the time required to fully scan a matrix can increased and a compromise between speed and resolution can be selected. Parallel detection devices which provide high resolution with shorter scan times are applicable where multiple detectors are moved in parallel.

In some applications, resolution often is not so important and sensitivity is emphasized. However, the reliability of a signal can be pre-selected by counting photons and continuing to count for a longer period at positions where intensity of signal is lower. Although this decreases scan speed, it can increase reliability of the signal determination. Various signal detection and processing algorithms can be incorporated into the detection system. In some methods, the distribution of signal intensities of pixels across the region of signal are evaluated to determine whether the distribution of intensities corresponds to a time positive signal.

D. Detection of Incorporation of Multiple Fluorescent Labels: FRET

In some aspects of the present application, incorporation of different types of nucleotides into a primer is detected using different fluorescent labels on the different types of nucleotides. When two different labels are incorporated into the primer in close vicinity, signals due to fluorescence resonance energy transfer (FRET) can be detected. FRET is a phenomenon that has been well documented in the literature, e.g., in T. Foster, Modem Quantum Chemistry, Istanbul Lectures, Part III, 93-137, 1965, Academic Press, New York; and Selvin, "Fluorescence Resonance Energy Transfer," Methods in Enzymology 246: 300-335, 1995. In FRET, one of the fluorophores (donor) has an emission spectrum that overlaps the excitation spectrum of the other fluorophore (acceptor) and transfer of energy takes place from the donor to the acceptor through fluorescence resonance energy transfer. The energy transfer is mediated by dipole-dipole interaction. Spectroscopically, when the donor is excited, its specific emission intensity decreases while the acceptor's specific emission intensity increases, resulting in fluorescence enhancement.

Detection of single molecule FRET signal reveals sequence information and facilitates interpretation of the sequencing data. Detection of FRET signal in the present invention can be performed accordingly to various methods described in the art (e.g., U.S. Pat. No. 5,776,782). FRET has been used to studying various biological activities of biomacromolecules including polynucleotides. For example, Cooper et al. disclosed fluorescence energy transfer in duplex and branched DNA molecules (Biochemistry 29: 9261-9268, 1990). Lazowski et al. reported highly sensitive detection of hybridization of oligonucleotides to specific sequences of nucleic acids by FRET (Antisense Nucleic Acid Drug Dev. 10: 97-103, 2000). Methods for nucleic acid analysis using FRET were also described in U.S. Pat. Nos. 6,177,249 and 5,945,283. Efficacy of using FRET to detect multiple nucleotides incorporation into single polynucleotide molecules is also exemplified in Example 8 of the present application.

Any of a number of fluorophore combinations can be selected for labeling the nucleotides in the present invention for detection of FRET signals (see for example, Pesce et al,. eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; which are incorporated by reference). In general, a preferred donor fluorophore is selected that has a substantial spectrum of the acceptor fluorophore. Furthermore, it may also be desirable in certain applications that the donor have an excitation maximum near a laser frequency such as Helium-Cadmium 442 nm or Argon 488 nm. In such applications the use of intense laser light can serve as an effective means to excite the donor fluorophore. The acceptor fluorophore has a substantial overlap of its excitation spectrum with the emission spectrum of the donor fluorophore. In addition, the wavelength of the maximum of the emission spectrum of the acceptor moiety is preferably at least 10 nm greater than the wavelength of the maximum of the excitation spectrum of the donor moiety. The emission spectrum of the acceptor fluorophore is shifted compared to the donor spectrum.

Suitable donors and acceptors operating on the principle of fluorescence energy transfer (FET) include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethyl-couluarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy5; Cy5.5; Cy7; IRD 700; IRD 800; La Jolla Blue; phthalo cyanine; and naphthalo cyanine.

Many modifications and variations of this invention can be made without departing from its spirit and scope. The specific embodiments described below are for illustration only and are not intended to limit the invention in any way.

EXAMPLES

Example 1

Basic Materials and Methods

1. Materials and Reaction Reagents
(1) Solutions and buffers
  RCA: $H_2O:NH_4OH:H_2O_2$ (6:4:1) boiling for an hour.
  PEI: PolyEthylenImine (Sigma P-3143) (positive charged)
  PALL: Poly(allylamine hydrochloride) (Sigma 283223)
  PACr: Poly(acrylic acid, sodium salt) (Sigma 416045) (negative charged)
  EDC: 9.6 mg/ml; 50 mM (×10) 1-{3-(Dimethylamino) propyl]-3-ethylcarbodiimide,
  hydrochloride), Activator for the BLCPA (Sigma-161462)
  BLCPA: EZ-Link Biotin LC-PEO-Amine (Pierce 21347)
    Stock solution 50 mM in MES 10 mM (21 mg/ml) (×10)
  Streptavidin plus—1 mg/ml in Tris. PROzyme, Code: SA20 (×10)
  Buffers:
  MES (N-morpholinoethanesulfonic acid) PH 5.5 1M (100×)
  TRIS 10 mM
  TRIS-$MgCl_2$ 10 mM Tris, 100 mM $MgCl_2$ (×1)
  TKMC (10 mM Tris•HCl, 10 mM KCl, 10 mM $MgCl_2$, 5 mM Ca $Cl_2$, pH 7.0)
  EcoPol: 10 mM Tris•HCl, 5 mM $MgCl_2$, 7.5 mM DTT pH@ 25° C.; buffer come with the polymerase at (×10)
(2) Other materials and reagents
  Nucleotides: dTTP, dGTP, dATP, and dCTP-Cy3 at 10 μM concentration
  Polymerase: a) Klenow Polymerase I (5 units/μl), New England BioLabs Cat. 210S
    b) Klenow—exo, New England BioLabs Cat. 212S
    c) TAQ
    d) Sequenase
  Hybridization Chamber: Sigma H-1409
  Polynucleotide templates and primers:
  7G: Biotin—5'-tcagtcatca gtcatcagtc atcagtcatc agtcatcagt catcagtcat cagtcatcag tcatcagtca tcagtcatca gtcatcACAC GGAGGTTCTA-3' (SEQ ID NO:1)
  Primer p7G: 5'-TAGAACCTCCGTGT-3' (SEQ ID NO:2); the primer can be labeled with Cy5 or Cy3.
  Mu50: Biotin 5'-ctccagcgtgttttatctctgcgagcat-aatgcctgcgtcatccgccagc 3' (SEQ ID NO:3)
  Cy5 labeled primer (PMu50Cy5): Cy5 5'-gctggcggatgac-3' (SEQ ID NO:4)

7G7A—Biotin—5'-tttGcttcttAttctttGcttcttAt-
tctttGcttcttAttctttGcttcttAt-
tctttGcttcttAttctttGcttcttAttcttACACGGA GGTTCTA-3' (SEQ ID NO:5)

6TA6CG: Biotin—5'-ccAtttttGccccccAtttttGc-
ccccAtttttGccccAtttttGccccccAtttttA-CACGGAGGT-TCTA-3', (SEQ ID NO:6)

2. Substrate Treatment and Template Attachment

A fused silica microscope slide (1 mm thick, 25×75 mm size, Esco Cat. R130110) was used to attach DNA templates. The slides was first cleaned with the RCA method as described above and in WO 01/32930. Multilayer of poly-allylamine/polyAcrylic were absorbed to the slide. An EZ link connector was then attached to the slides as follows: the slide was dried, scratched with diamond pencil, and then covered with a hybridization chamber. 120 µl of a mixture of 1:1:8 EDC: BLCPA: MES (50 mM EDC, 50 mM BLCPA, 10 mM MES) was applied to each slide. Following incubation for 20 minutes, 120 µl of Streptavidin Plus diluted to 0.1 mg/ml was added to the slide. After 20 min of incubation, the slide was washed with 200 µl of Tris 10 mM.

Preparation of 10 pM Oligo: the 7G oligonucleotide template (SEQ ID NO:1) was pre-hybridized with Cy5-labeled primer (SEQ ID NO:2) (in stock at 7 µM) in TRIS-MgCl$_2$ buffer. The treated slide was examined for contamination with the TIR microscope. 200 µl of the oligonucleotide/primer mixture was applied to each slide. Following incubation for 10 min, the slide was washed with 200 µl ml of Tris 10 mM.

Addition of nucleotides and polymerase: nucleotides dTTP, dATP, dGTP, and Cy3-dCTP each of 20-100 nM were mixed in the ECOPOL buffer. 1 µl Klenow 210S from stock solution (kept in −20° C.) was added to 200 microliters of the nucleotide mixture. 120 µl of the mixture was then added on each slide. After incubation for 0 to 30 min (for different experiments), the slide was examined with the TIR microscope. Unless otherwise noted, all reactions were performed at room temperature, while the reaction reagents were kept at 4° C. or −20° C. The primer/oligonucleotide hybridization reaction was carried out with a thermocycler machine.

Single molecule resolution was achieve by using very low concentration of the polynucleotide template which ensured that only one template molecule is attached to a distinct spot on the slide. Single molecule attachment to a distinct is also confirmed by the observation of single bleaching pattern of the attached fluorophores. In the reaction described above, a concentration of about 10 pM of a 80-mer oligonucleotide template was used for immobilizing to the slide. The space between different DNA molecules attached to the surface slide was measured at a few micrometers.

3. Imagine with Single Molecule Resolution

As illustrate in FIG. 1, the single stranded oligonucleotide template (SEQ ID NO:1) primed with a Cy5 labeled primer sequence (SEQ ID NO:2) was immobilized at a single molecule resolution to the surface of a silica slide using a biotin-streptavidin bond. The surface is coated with polymers on which biotin (EZ link) is tethered. The oligonucleotide template, with a biotin molecule attached to one of its ends, was able to attach to the streptavidin-linked surface. The slide surface was negatively charged which helps to repeal unbound nucleotides The DNA is specifically attached to the surface by its 5' side, meaning that the primer—which the polymerase extends—is away from the surface.

The template and incorporation of labeled nucleotides were visualized by fluorescence imaging. Location of the oligonucleotide was monitored by fluorescence from the Cy5 labeled primer (SEQ ID NO:2). Incorporation of nucleotides was detected because the nucleotides were labeled with Cy3. After incorporation, the incorporated labels were illuminated. Illumination of Cy3 was at a wavelength of 532 nm. Following a typical time of a few seconds of continued illumination, the signals were bleached, typically in a single step.

Figure 2:
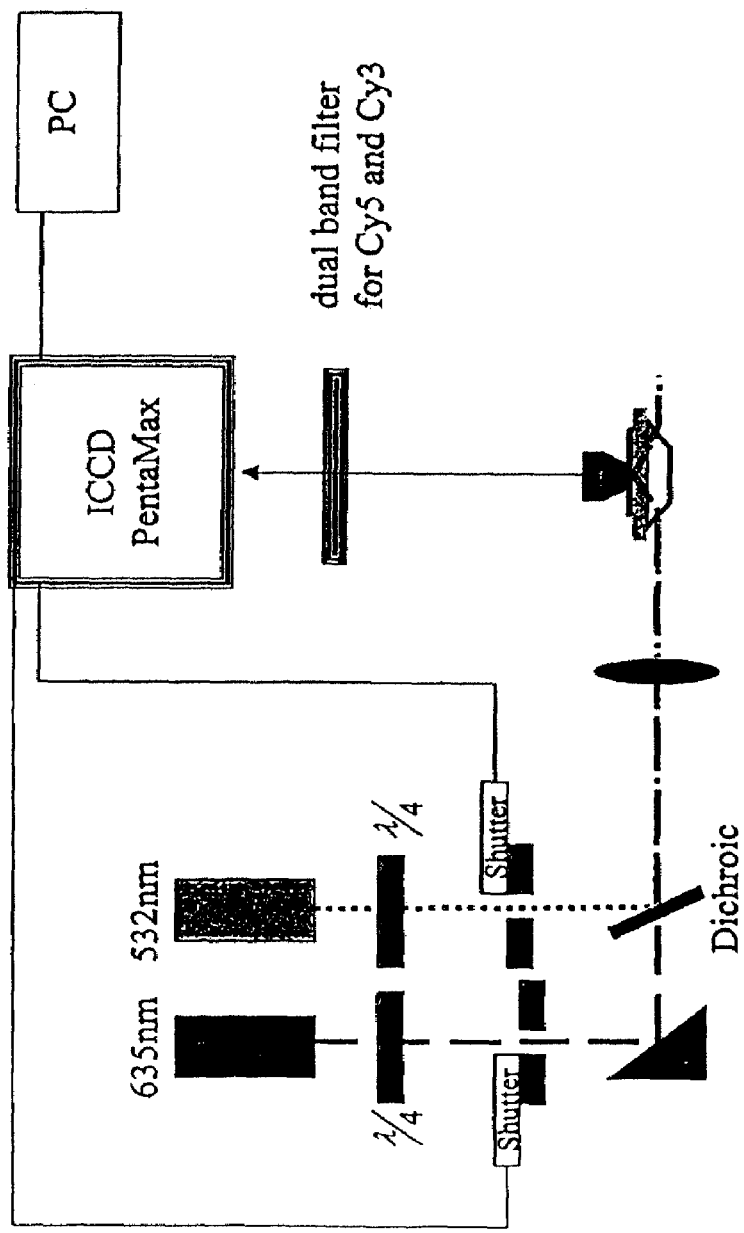
FIG. 2 shows schematically the optical setup of a detection system for total internal reflection microscopy.

As shown in FIG. 2, imaging of fluorescent signals with single molecule resolution was enabled with surface illumination by total internal reflection (TIR). Ishijima et al. (Cell 92:161-71, 1998) showed that it is possible to observe the fluorescence of single molecules immobilized to a surface in a wet environment even when there are free molecules in the solution. Here, the TIR was facilitated by a dove prism coupling of the laser beam to the silica slide surface. An upright microscope with an immersion oil objective was used to image the surface with an intensified CCD (PentaMax). A filter set (Chroma) was used to reject the illumination frequency and let the fluorescence frequency to reach the ICCD.

Example 2

Test for Specific Attachment of Template Molecules to Substrate Surface

Figure 3:
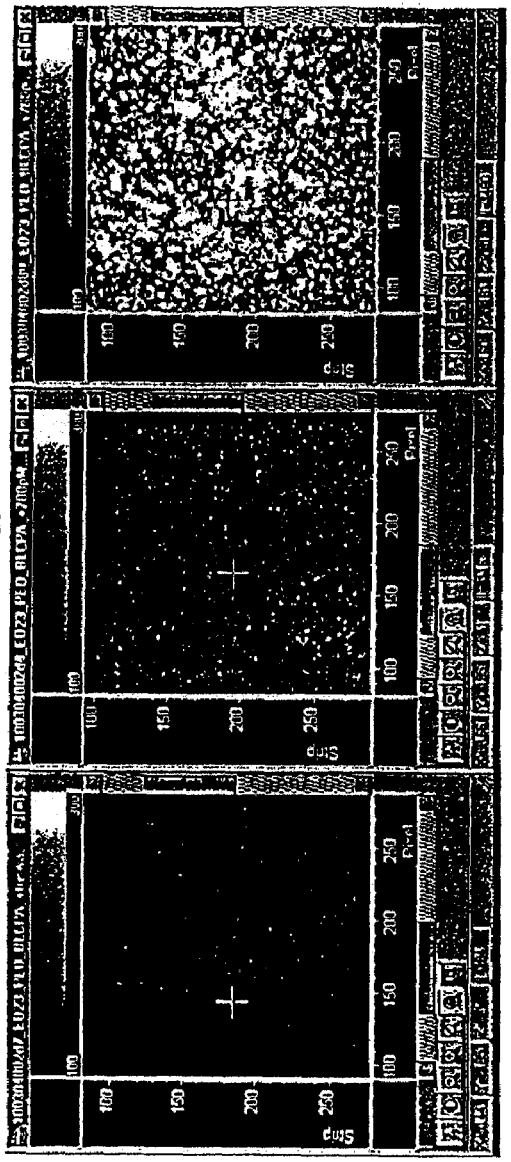
FIG. 3 shows results which indicate that streptavidin is required for immobilizing the polynucleotide template in an exemplified embodiment.

This experiment was performed to determine whether the polynucleotide templates are attached to the surface as desired. FIG. 3 shows that streptavidin is required for binding the template to the surface and hence detection of incorporated fluorescence signal. The left panel shows that there is no fluorescence signal when only streptavidin-attached surface but no fluorescent labels were present. The middle panel shows that there is no incorporated fluorescent signals when no streptavidin was present on the surface to attach biotin-labeled oligonucleotide template, even though Cy5-labeled primer was present. The right panel shows that detection of incorporated fluorescent signal when the streptavidin-attached surface, labeled primers, and biotin-labeled oligonucleotide template were present.

Example 3

Figure 5:
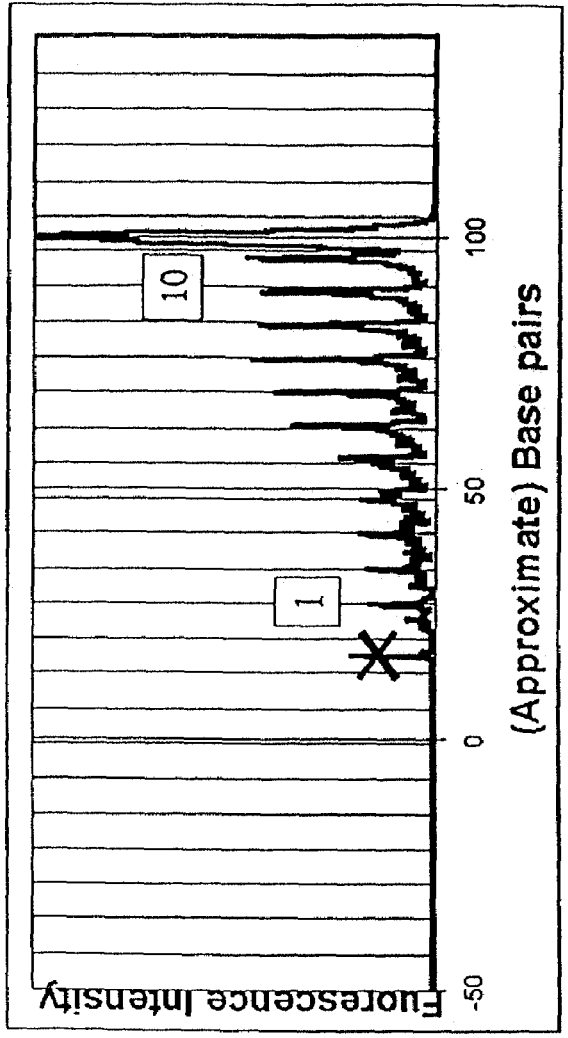
FIG. 5 shows incorporation of multiple labeled nucleotides in a bulk experiment in solution, using biotin-labeled 7G oligonucleotide template (SEQ ID NO:1) and p7G primer (SEQ ID NO:2).

Determining Processivity of DNA Polymerase in the Presence of Labeled Nucleotides To determine whether the DNA polymerase accurately incorporates labeled nucleotides into the template, a bulk extension experiment was performed in a test tube rather than on the surface of a substrate. As shown in FIG. 5, the results indicate that the polymerase incorporate all the labeled nucleotides into the correct positions. In this experiment, incorporation of dCTP-Cy3 and a polymerization terminator, ddCTP, were detected using a 7G DNA template (a DNA strand having a G residue every 7 bases; SEQ ID NO:1). The annealed primer was extended in the presence of non-labeled dATP, dGTP, dTTP, Cy3-labeled dCTP, and ddCTP. The ratio of Cy3-dCTP and ddCTP was 3:1. The reaction products were separated on a gel, fluorescence excited, and the signals detected, using an automatic sequencer ABI-377. The results reveal that incorporation of Cy3-dCTP did not interfere with further extension of the primer along the 7G oligomer template.

FIG. 5 shows fluorescence intensity from primer extension products of various lengths which were terminated by incorporation of ddCTP at the different G residues in the 7G oligomer template (SEQ ID NO:1). The first band is the end of the gel and should not be counted as it is in the very beginning of the gel. The full length of the template is 100 residues. The first band (marked "1" in the graph) corresponds to extension products which were terminated by incorporation of non-labeled ddCTP at the second G residue (position 27) and has incorporated Cy3-dCTP at the first G residue (position 20). Similarly, the tenth band (marked "10" in the graph) represents extension products which were terminated by incorporation of non-labeled ddCTP at the 10th G residue (position 90) and has incorporated Cy3-dCTP at the previous G residue (i.e., positions 20, 27, 34, 41, 48, 55, 62, 69, 76, and 83). The results showed a nice agreement between the expected positions for Cy3 incorporation in the polynucleotide template and the positions of the fluorescence intensity bands.

Example 4

Detection of Single Nucleotide Incorporation by TIR

Total internal reflection (TIR) fluorescence microscopy allows detection of real-time incorporation of labeled nucleotide into single immobilized polynucleotide template. This illumination method reduce the background from the sample by illuminating only a thin layer (e.g., in the order of 150 nm) near the surface. Even in the presence of free dyes in the solution (up to 50 nM), single molecules can be observed. Using TIR, we visualized single molecules of labeled nucleotide bound to DNA in the presence of up to 50 nM free dye in solution. Though this concentration is low compared to the concentration needed for a high rate of incorporation of nucleotides by the DNA polymerase, it was sufficient for its operation.

1. Optical Setup

The lasers source is shown in FIG. 2, the light sources (e.g., laser) are coupled to the surface by prism. The surface is imaged by a regular 1.3 NA microscope objective onto an Intensified CCD (Pentamax). A fluorescent filter in the optical way block the laser intensity and allow the fluorescent signals from the dye molecules pass through(Chroma filters). Optionally, the camera and the shutters for the lasers are controlled by the computer.

2. Illumination

Figure 6:
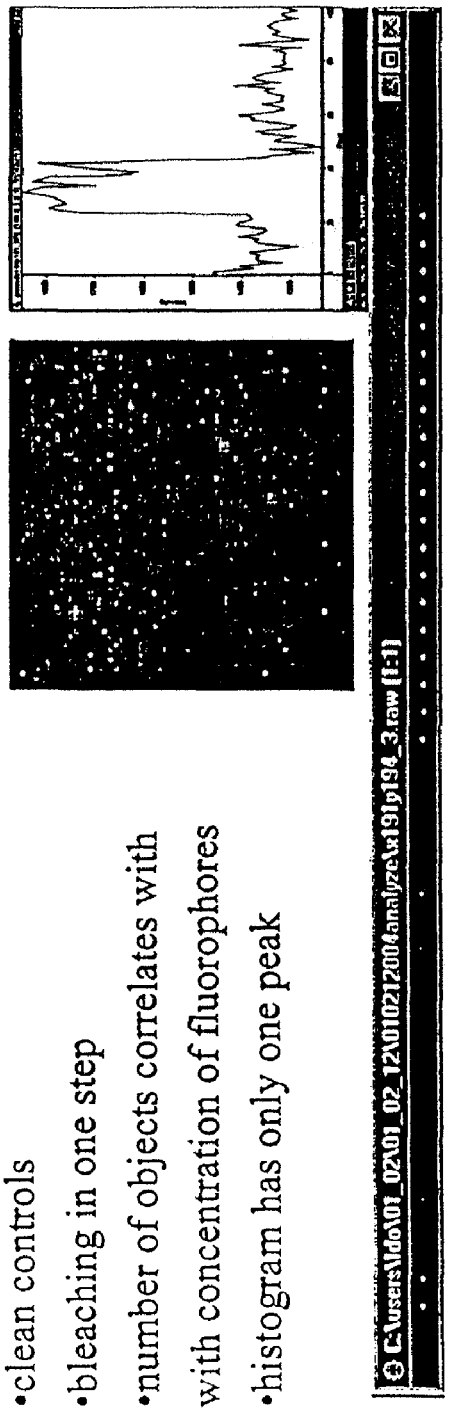
FIG. 6 shows low background signal from free nucleotides in solution and detection of signals from incorporated nucleotides.
Figure 6:
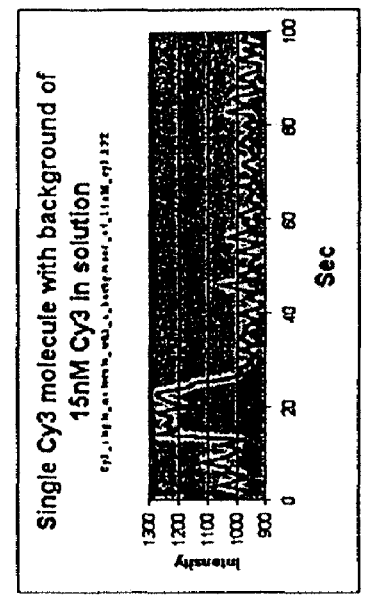
Figure 6:
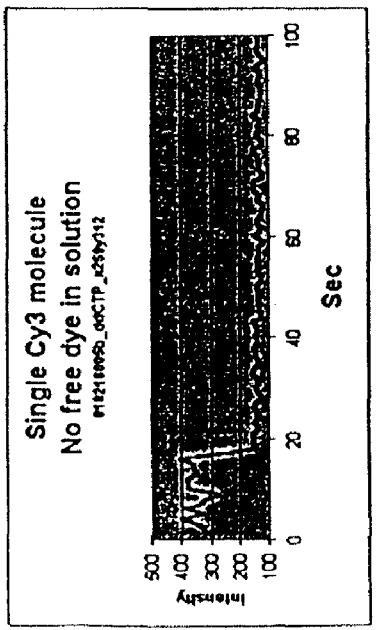

As shown in FIG. 6, TIR illumination of polynucleotide-attached slide produced a low background and allowed detection of signals only from immobilized labels. The refraction index of the fused silica glass and the oil beneath the surface is about 1.46. The refraction index of the liquid above the glass is about 1.33 to 1.35. At the interface of the glass and the water the illumination ray was refracted. If the illumination is very shallow, 70-75 degree from the surface orthogonal, the refracted light was reflected back and not continued in the liquid phase as the critical angel for total internal reflection is about 65-67 degrees (TetaCitical=sin$^-1$(n1/n2)).

The illumination process, called evanescent illumination, leaves a decay field near the interface which illuminates only about 150 nm into the liquid phase. Fluorophores dyes can be excited by this field. So only the dyes which are near the surface will emit. Furthermore, free labeled nucleotide molecules in the solution will move around due to Brownian motion. The fast movement of these free molecules produces only a smear signal because the integration time is in the order of hundred millisecond. Thus, the total internal reflection illumination leads to a low back ground from the free molecules, and only signals from the immobilized dyes are detected.

3. Detection of Single Molecules

FIG. 6 shows detection of signals from single Cy3 molecule with no free dye in solution versus signals from single Cy3 molecule with background of 15 nM Cy3 in solution. Fluorescence image from incorporation of Cy3 labeled nucleotide is shown in the upper panels. The signals tend to bleach in a single step, see the upper graph. When there are free labeled nucleotides in the solution (15 nM free dye), the background signal is stronger (lower right panel) than the background signal in the absence of free labeled nucleotides in the solution. But the signal from the incorporated single molecule can still be detected. The ability to detect single molecule in the presence of free dye enables one to follow incorporation of nucleotide into an immobilized DNA template in real time.

The upper left panel of FIG. 6 showed typical images of single molecules (see the bright spots). When the intensity of a spot is traced in real time (upper right panel), one can see that it appears (incorporation event or sticking to the surface event) and disappears (bleaching or detaching event). The same results are also illustrated in the middle long thin panel of FIG. 6. This panel shows successive images of a small area around the spot that was being traced. The fluorescent signal appeared and disappeared after every few seconds (every frame is a second exposure).

Example 5

Determining Nucleotide Incorporation Based on Correlation of Fluorescence Spots

Figure 4:
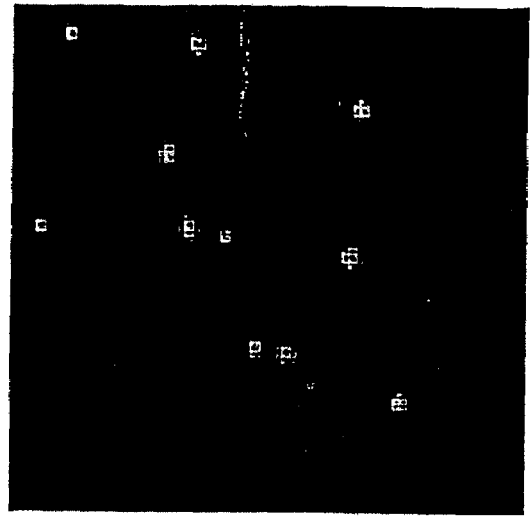
FIG. 4 shows results which indicate that DNA polymerase incorporating labeled nucleotide into the immobilized primer is visualized with single molecule resolution.
Figure 4:
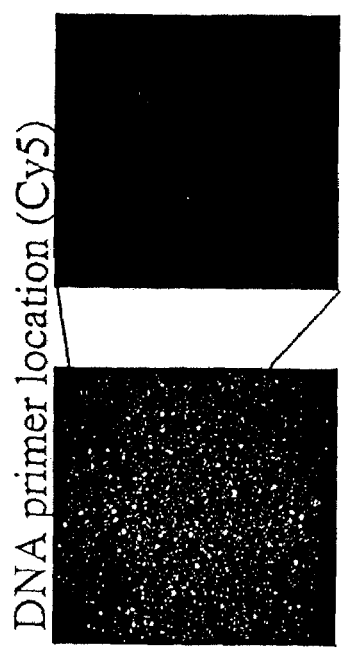
Figure 4:
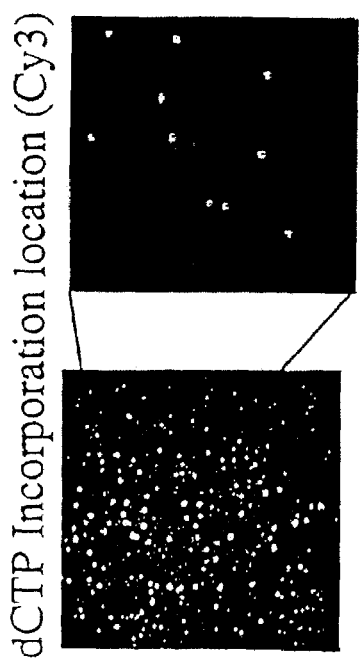

A correlation was observed between the position of the immobilized DNA template on the surface (indicated by the fluorescently labeled primer) and the incorporation of nucleotide to the surface. In FIG. 4, image of the immobilized DNA which was hybridized to the Cy5 labeled primer was shown in the upper two panels (the middle panel is a magnified image of a small area in the left panel). The small dots in the image represent likely positions of the DNA templates immobilized on the surface. The fluorescence signals were then bleached out by a long radiation (about 1 minute) at 635 nm with a 10 mW laser diode. Subsequently, the polymerase and the nucleotides (including the Cy3-labeled dCTP) were added, and the mixture incubated at room temperature for about an hour. After washing, a second image of the surface was taken. This time a new set of fluorescence-labeled points appeared (see lower left two panels). The results indicate that the two sets of fluorescently-labeled points are correlated (see right panel). It is noted that the significant overlap (about 40%) between DNA primer location (Cy5) and dCTP Incorporation location (Cy3) cannot be a random result. Under the concentrations of labeled DNA primers used in the experiment, the probability for this correlation to occur randomly calculated to be about $10^{-50}$. Rather, the correlation is due to incorporation of the Cy3 labeled nucleotides into the immobilized, Cy5 labeled primer.

Figure 7:
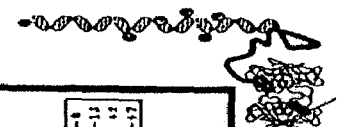
FIG. 7 shows results from experiments and simulation of multiple bleaching.
Figure 7:
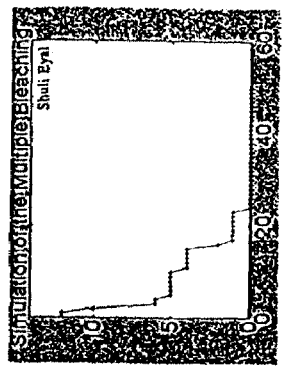
Figure 7:
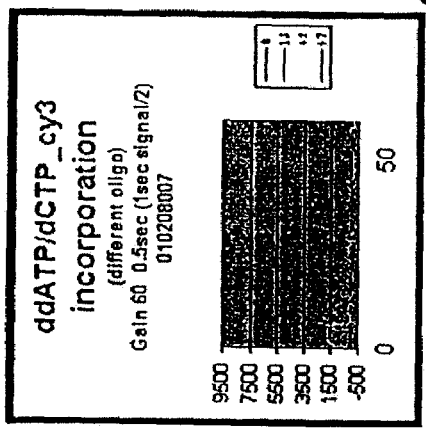
Figure 7:
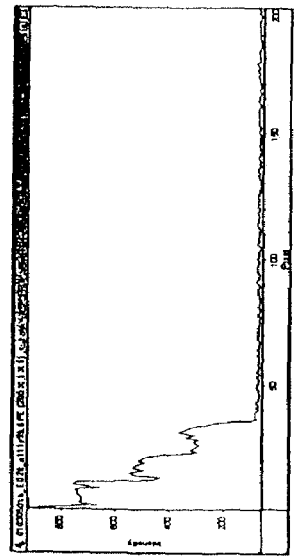
Figure 7:
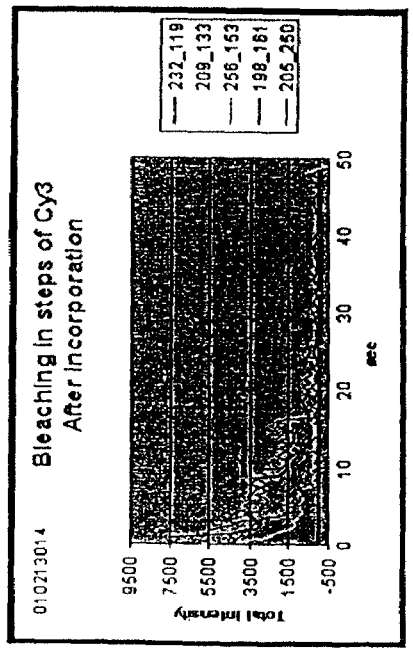

Incorporation of labeled nucleotide into the immobilized template is also demonstrated by the multi-incorporation data shown in FIG. 7. When the intensity of the spots in FIG. 4 were measured, a multistep bleaching is observed (FIG. 7, upper left panel). Simulation of the multiple bleaching is shown in the upper right panel. The results are what should be expected if few molecules are located in the same place up to the optical resolution. This indicates that the polymerase can incorporate a few labeled nucleotides into the same DNA template. In a control experiment, ddATP, dCTP-Cy3 and dGTP were used to extend Cy5-labeled primer PMu50Cy5, Cy5 5'-gctggcggatgac-3' (SEQ ID NO:4) along the Mu50 oligonucleotide template (SEQ ID NO 3). This allows only one Cy3-labeled nucleotide to be incorporated into the primer because the first codon in the template sequence after the primer is CGT. Incorporation of ddATP immediately after the incorporation of dCTP-Cy3 terminates the elongation. As shown in the lower right panel, there is no multibleaching.

It is noted that because the concentration of the DNA template on the surface was so low, it is unlikely that more than one copy of the DNA template were present on each spot. Further, multiple bleaching is not common when the polymerase was not present (data not shown). In particular, there is no correlation between primer location and fluorescence signal from the surface when the polymerase was not present (see, e.g., FIG. 13, middle panel).

Example 6

Dynamics of Nucleotide Incorporation

Figure 8:
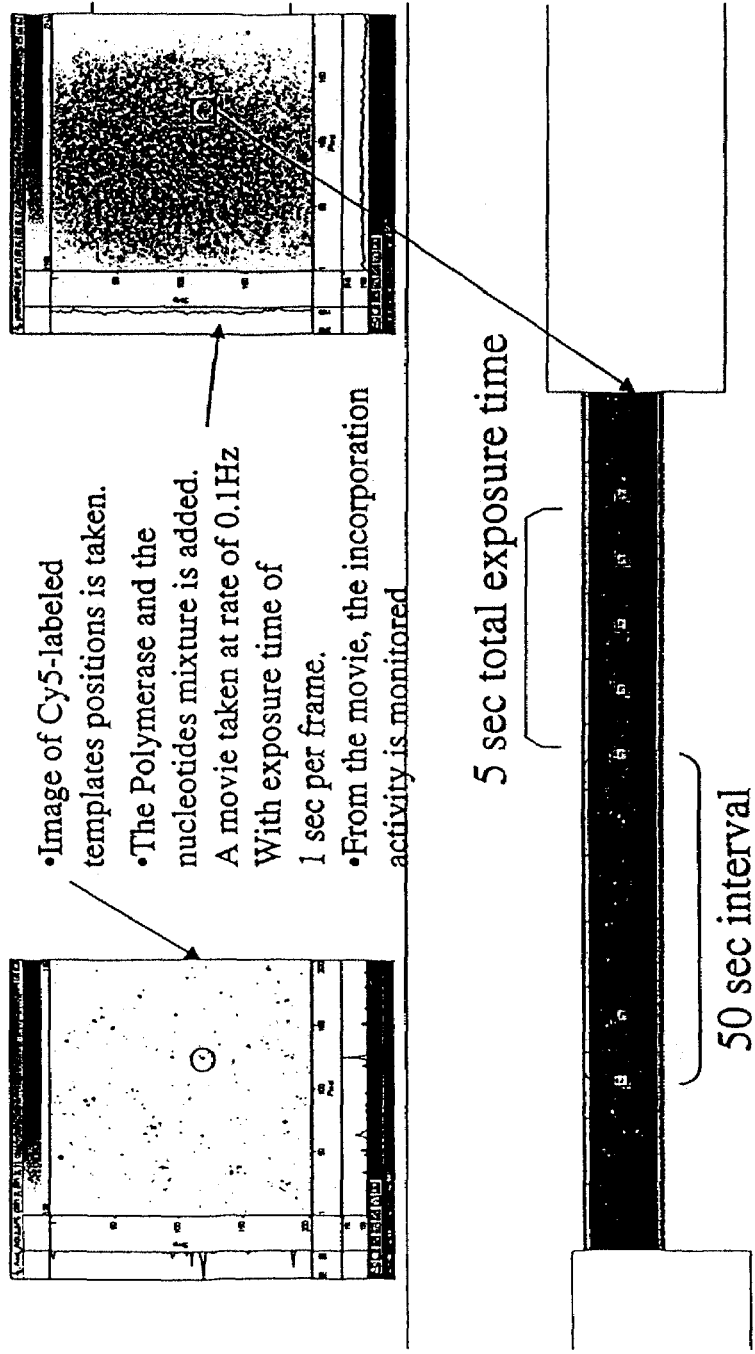
FIG. 8 shows dynamics of incorporation of labeled nucleotides into the immobilized primer.

FIG. 8 shows a time course of incorporation events during the DNA polymerase reaction. In this experiment, the DNA template and Cy5-labeled primer complex was immobilized to the substrate surface as described above, and its position was imaged. The DNA Polymerase was then added along with the nucleotides of which one was labeled with Cy3.

As indicated in the figure, the substrate was imaged every 10 sec, with a 1 sec exposure. Every spot with immobilized DNA template (as indicated by the labeled primer) was monitored as a function of time. A series of small images of these spots were placed along a strip resulting in a movie showing the "activities" at each point.

Figure 9:
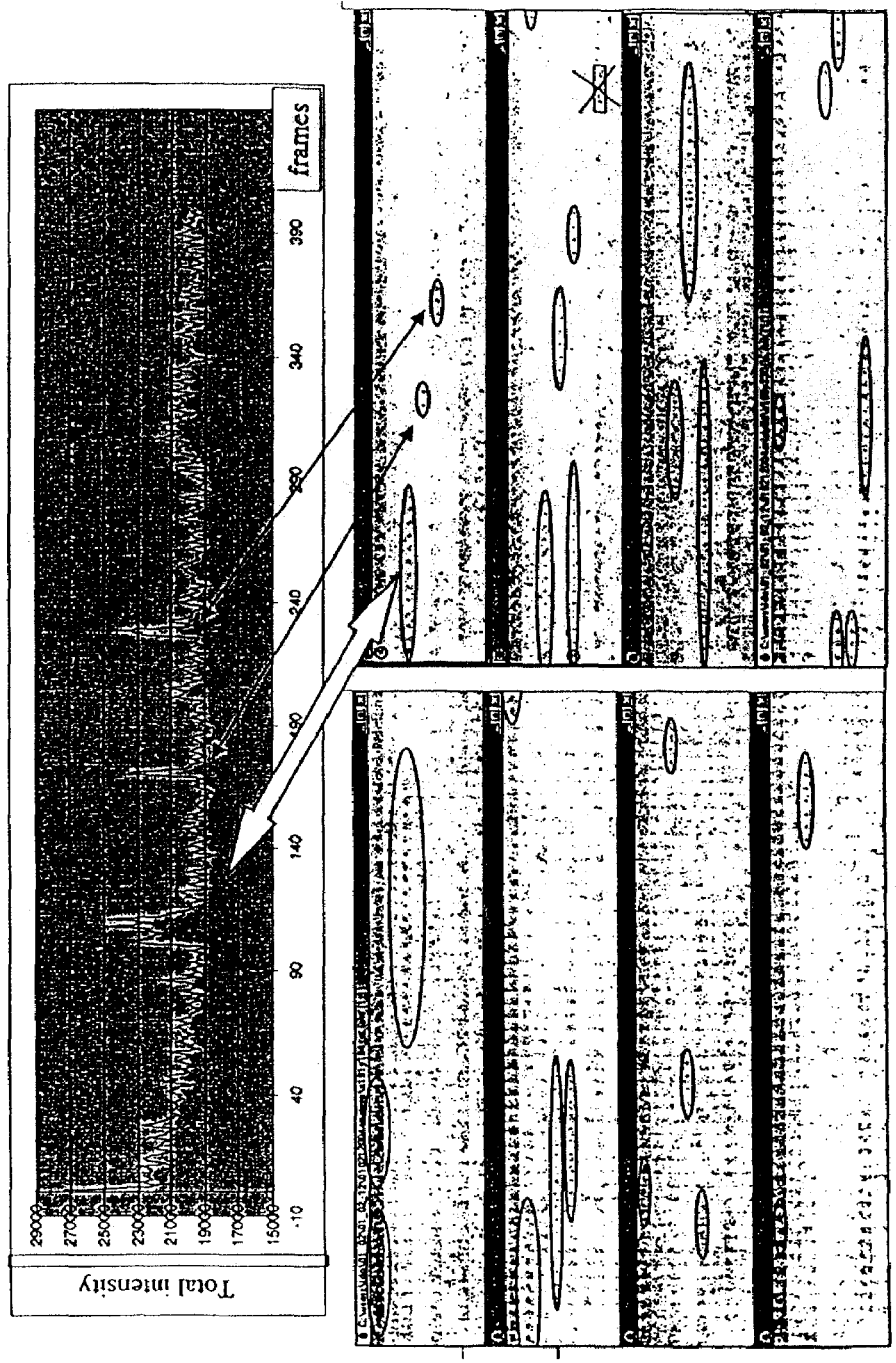
FIG. 9 shows multiple incorporation events of labeled nucleotides over a period of time.

Repeated incorporation of nucleotide into the DNA template was shown in FIG. 9. Using more dyes will enable us to read the sequence of the DNA directly in an asynchronous manner. FIG. 9 shows the dynamic incorporation events at 8 different spots. The digital information recorded in these movies indicate that repeated incorporation events occurred at various time points. The data also demonstrated the feasibility of monitoring primer extension activities on single DNA molecules.

Figure 10:
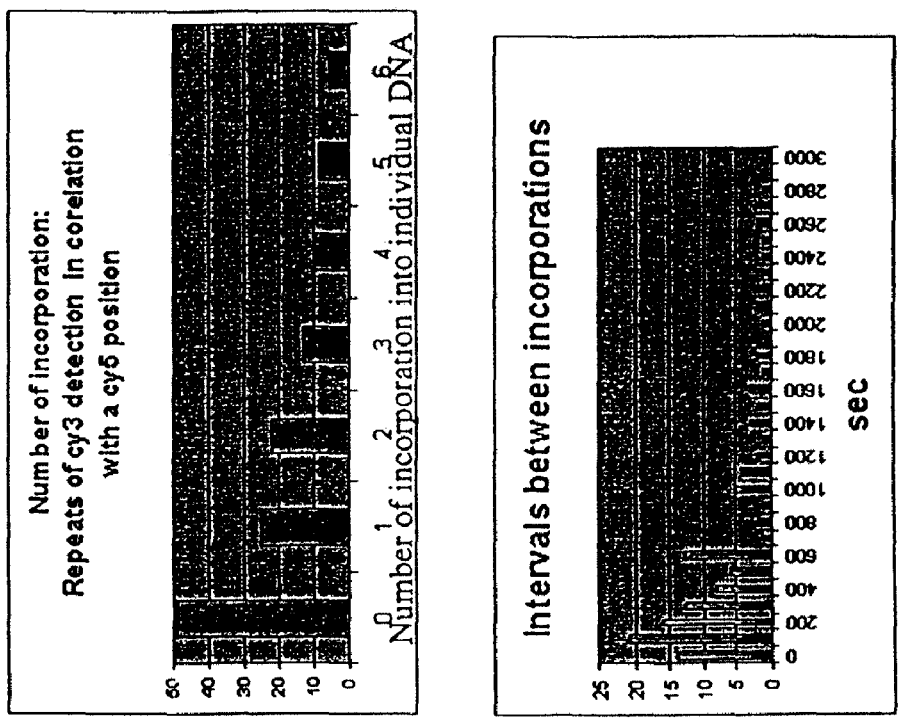
FIG. 10 shows statistics of incorporation of labeled nucleotides over a period of time.

FIG. 10 shows a histogram of the number of incorporation events on single spots and a histogram of the time between incorporation events. From the histograms one can see that a few nucleotides were incorporated into single DNA molecules. The low numbers of events in which more then three nucleotides were incorporated indicate that there is some mechanism that prevents high number of incorporation into the DNA under the experimental conditions. The reason could be that photo-damage to the DNA in the surrounding area of the illuminated dye might produce toxic radicals. Changing the reaction conditions and reagents could increase the numbers of incorporated nucleotides dramatically.

Example 7

Base-by-base Sequence Analysis

This experiment was performed to confirm selectivity of the polymerase and to illustrate feasibility of determining the sequence of a polynucleotide template with base-by-base scheme.

Figure 11:
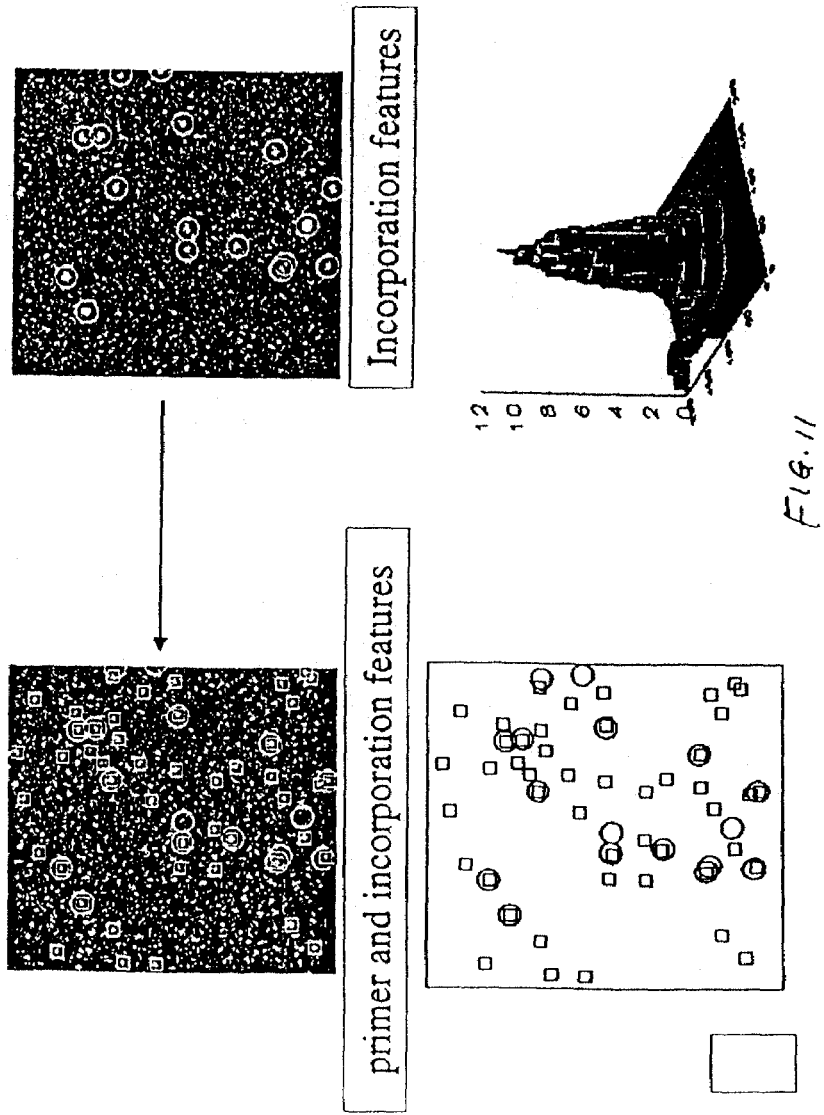
FIG. 11 shows correlation between location of labeled primer and location of incorporation of labeled nucleotides.

First, fidelity of the polymerase in incorporation was confirmed by analyzing correlation between location of immobilized primer and location of nucleotide incorporation with a correlation graph. FIG. 11 shows correlation between primer location and polymerase activity location. The position of each point was determined with a sub pixel resolution. Images for the primer location and the incorporation position were taken first. If there is a correlation between the two, there is a pick in the correlation graph. Otherwise no pick was observed. As shown in the figure, the two images correlate with each other.

Figure 12:
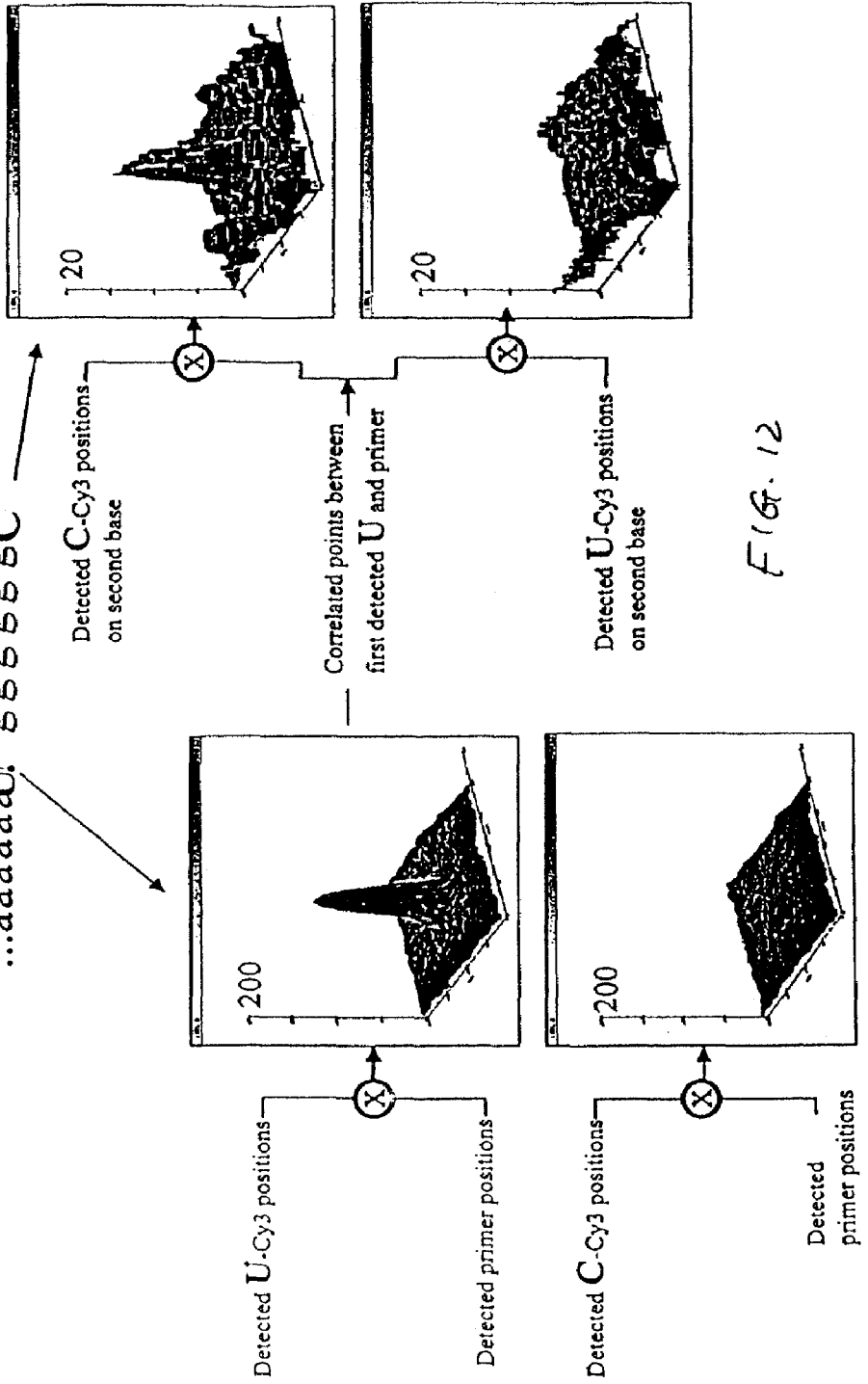
FIG. 12 shows correlation graphs for incorporation of two labeled nucleotides, using a 6TA6GC oligonucleotide template (SEQ ID NO:6) and a p7G primer (SEQ ID NO:2). Partial sequences of the template, 5'-GccccccAtttttt-3' (SEQ ID NO:7), and the extended product, 5'-aaaaaaUggggggC (SEQ ID NO:8), are also shown in the Figure.

Results demonstrating base-by-base analysis of the sequence of a immobilized template at single molecule resolution is shown in FIG. 12. The data indicated that at least two bases of the template were determined by flowing in and out reagents along with different types of labeled nucleotides (e.g., dCTP-Cy3, dUTP-Cy3, etc.). Here, a 6TA6GC oligonucleotide template (SEQ ID NO:6) was immobilized to the fused silica slide. A Cy3-labeled p7G primer (SEQ ID NO:2) was annealed to the template. As illustrated in the Figure, the primer was first extended up to the A residue with non-labeled dATP nucleotides. Then, dUTP-Cy3 nucleotide was incorporated and imaged. Images taken at this time show high correlation (see the upper left correlation graph). After bleaching the dyes, dCTP-Cy3 was applied to the sample. Images taken at this time show low correlation (see the lower left correlation graph). Thereafter, non-labeled dGTP was added to fill the CCCCC gap till the G residue in the sequence. At this time, incorporation of a dCTP-Cy3 nucleotide was examined again. This time there was a correlation between the dCTP-cy3 positions and the primer positions in general, and in particular there was a correlation with the position of the incorporated dUTP in the first incorporation cycle. Thereafter, dUTP-Cy3 was added. Correlation was found between the labeled primer position and signal from dUPT-Cy3, but no correlation was found between the new dUPT-Cy3 positions and the position that has incorporated dUTP in the first incorporation cycle (lower right graph). The interpretation is that not all the primers were extended in the first dUTP incorporation cycle, that those which did not get extended could incorporate dUTP in the second incorporation cycle, and that those which did incorporate dUTP in the first cycle could not incorporate dUTP again in the second cycle. The results indicate that on those spots which have incorporated the first U residue there were also incorporations of a C but not a U residue. Thus, identity of a second base can be determined with the experimental scheme, although the yield for the second base (upper right graph) was not as good as for the first base (upper left graph).

In a control experiment, after filling in with A residues, dCTP-Cy3 (wrong nucleotide for the first base) was added. Correlation between Cy3-labeled primer position and C-Cy3 was low (data not shown). In another control, after filling in the string of A residues, the U residue, G residues, and U-Cy3 (wrong residue for the second base) was added. The correlation observed from the results in this experiment was low (at the noise level; data not shown). Using different oligonucleotide templates, the experiment scheme was repeated for successive incorporations of other combinations of two or more nucleotides (data not shown). The results confirmed correct incorporation of the first labeled nucleotide with high signal-to-noise ratio and subsequent incorporations of more nucleotides with a relatively lower signal-to-noise ratio. Taken together, these data indicate that the observed results (e.g., as shown in FIG. 12) are not due to artifacts, but rather demonstrate efficacy of base-by-base analysis of the experimental scheme.

Example 8

Two Color Incorporation: Fluorescence Resonance Energy Transfer

Figure 13:
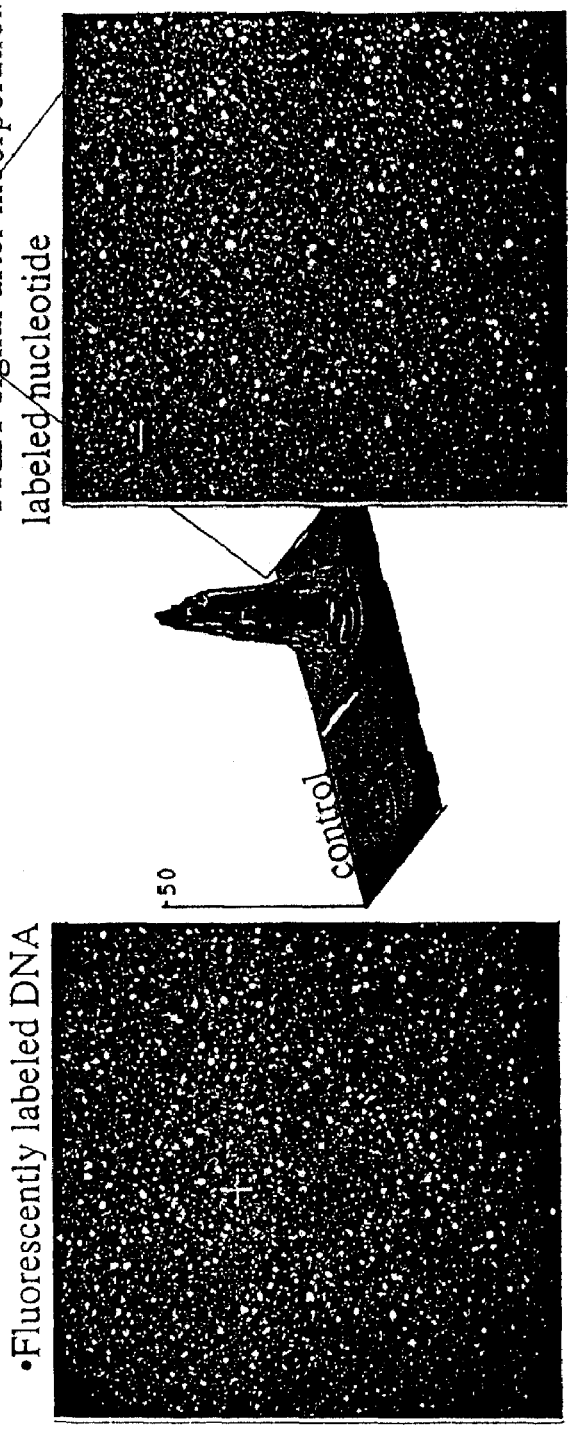
FIG. 13 shows detection of fluorescence resonance energy transfer (FRET) when two different labels are incorporated into the same primer. The polynucleotide template used here is the 7G7A oligonucleotide (SEQ ID NO:5), but only part of the sequence, 5'-AttctttGcttcttAttctttGcttcttAttctttG-3' (SEQ ID NO:9), is shown in the Figure.

This experiment demonstrate incorporation of two different fluorescent labels into the same immobilized polynucleotide template through detection of fluorescence resonance energy transfer (FRET). In this experiment, two fluorescent labels were used (Cy5 and Cy3), and FRET from dUTP-Cy3 (donor) to dCTP-Cy5 (acceptor) was examined at the single molecule level as shown in FIG. 13.

Image of the DNA template with the labeled primer is shown in the left panel. Detection of FRET after incorporation of the two labels is provided in the right image. Correlation between the template location and the incorporation signals is shown in the middle graph. As indicated, there is a high correlation between the template location and the incorporated nucleotide location. A control experiment was performed in which no polymerase is present. Results from the control experiment produced a low correlation between the template location and location of labeled nucleotides. FRET experiment provides particularly high signal to noise ratio as there is almost no signal from nonspecific incorporation of dyes to the surface.

Figure 14:
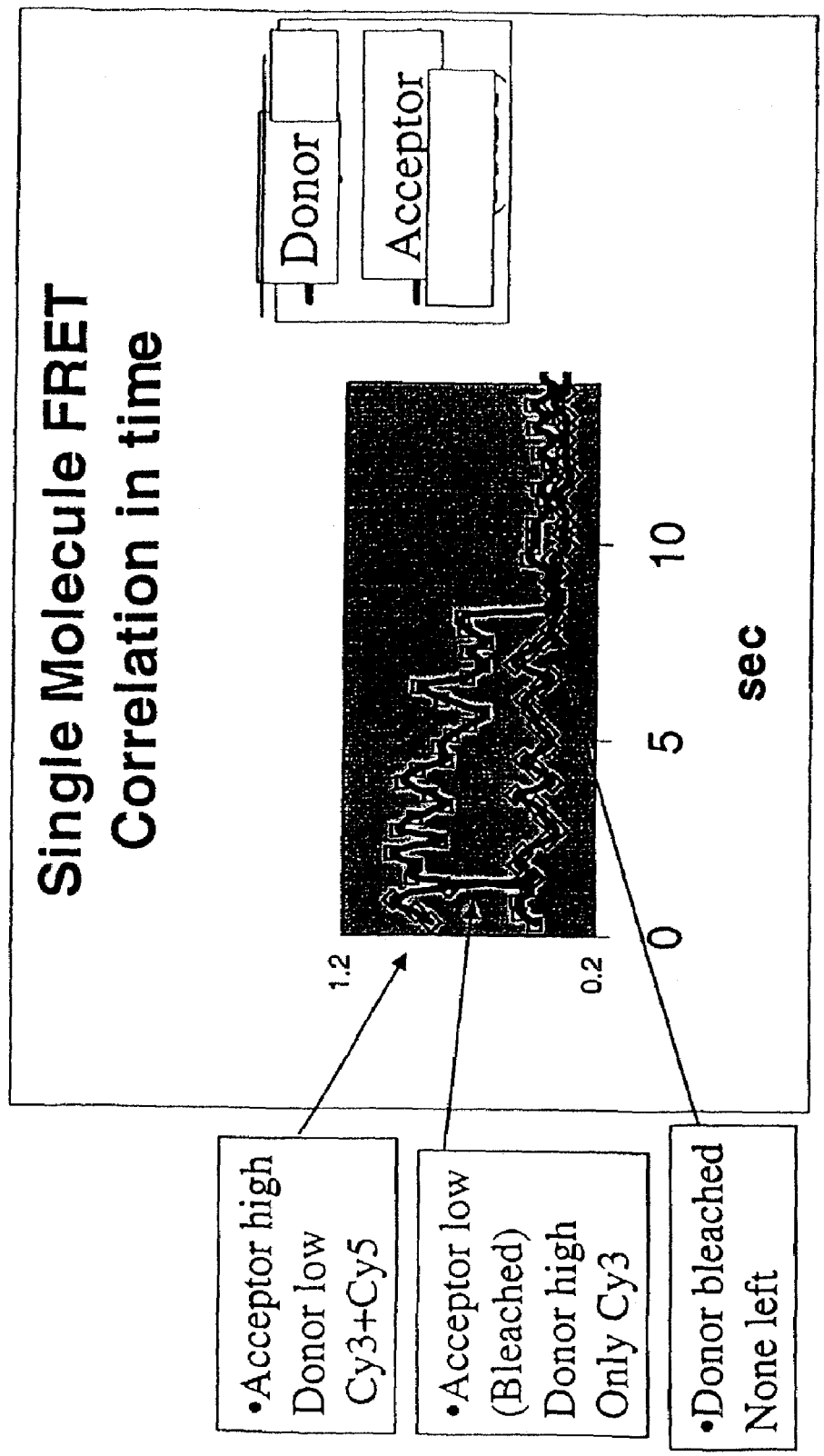
FIG. 14 shows correlation of single molecule FRET signals over a period of time.
Figure 15:
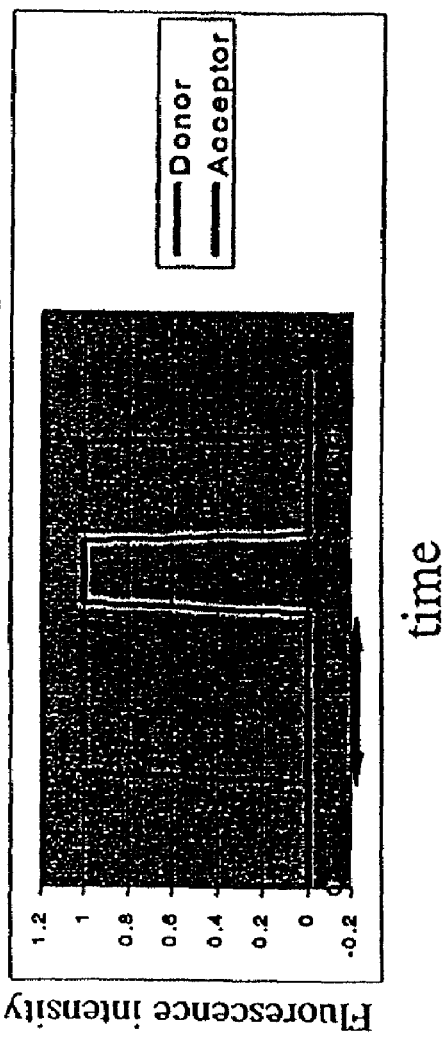
FIG. 15 shows the expected signals from an experiment in which two colors, donor and acceptor, are incorporated one after the another. Partial sequences of the template, 5'-GccccccAtttttt-3' (SEQ ID NO:7), and the extended product, 5'-aaaaaaUggggggC (SEQ ID NO:8), are also shown in the Figure.

When the two labels were incorporated into a primer at close vicinity, i.e., at a few nanometers apart, a single molecule FRET signal was detected (FIG. 14). To detect the FRET signal, the optic setup was altered. A image splitter was added so that the same area was imaged twice(Optical Insights LTD, micro imager device). In one channel, a fluorescence filter detected only the donor (cy3) fluorescence. In the other channel, a filter for the acceptor (Cy5) was placed. With this setup individual spots were examined after incorporation. FIG. 15 further indicates that the FRET detection scheme allows measurement of incorporation rate with a nice signal to noise ratio.

What is claimed is:

1. A method of analyzing sequence of a target polynucleotide, comprising:
   (a) providing a primed target polynucleotide comprising a substantially complementary fluorescently labeled primer and a target polynucleotide, the primed target polynucleotide being immobilized to a substrate comprising a polyelectrolyte coated multilayer surface, wherein the target polynucleotide is randomly attached to the polyelectrolyte multilayer coated surface with single molecule resolution;
   (b) adding a first fluorescently labeled nucleotide to the surface of the substrate under conditions whereby the first nucleotide is added to the primer;
   (c) determining whether a fluorescence signal from the fluorescently labeled nucleotide is present in at least one molecule of the primed target polynucleotide on the surface of the substrate, wherein the presence of the signal from the fluorescently labeled nucleotide indicates that the fluorescent nucleotide is added to the primer;
   (d) removing the fluorescent signal from the fluorescently labeled nucleotide; and
   (e) repeating steps (b)-(d) with a further fluorescently labeled nucleotide, thereby analyzing the sequence of the target polynucleotide, wherein if the primer label and the nucleotide label are the same, detecting and then bleaching the fluorescent signal from the primer label prior to adding the first fluorescently labeled nucleotide.

2. The method of claim 1, wherein step (a) comprises providing a plurality of different primed target polynucleotides immobilized to different portions of the substrate.

3. The method of claim 1, wherein steps (b)-(d) are performed with at least four different types of fluorescently labeled nucleotides.

4. The method of claim 1, wherein steps (b)-(e) are performed until the identity of each base in the target polynucleotide has been identified.

5. The method of claim 1, wherein presence or absence of fluorescence signal from the fluorescently labeled nucleotide is determined with total internal reflection fluorescence (TIRF) microscopy.

6. The method of claim 1, wherein the first and further nucleotide are labeled with the same fluorescent label.

7. The method of claim 1, wherein said substrate is a fused silica slide.

8. The method of claim 1, wherein said polyelectrolyte multilayer is terminated with a polyanion.

9. The method of claim 8, wherein said polyanion bears pendant carboxylic acid groups.

10. The method of claim 9, wherein said target polynucleotide is biotinylated, and said surface is coated with streptavidin.

11. The method of claim 10, wherein said surface is coated with biotin prior to coating with streptavidin.

12. The method of claim 1, wherein said removing is by photobleaching.

13. The method of claim 1, wherein the substrate is in fluid communication with a microfluidic device, wherein the first and further labeled nucleotides are added to or removed from the substrate through the microfluidic device.

14. The method of claim 13, wherein the microfluidic device comprises
   (a) a flow cell comprising the substrate; and
   (b) an inlet port and an outlet port, said inlet port and outlet port being in fluid communication with said flow cell for flowing fluids into and through said flow cell.

15. The method of claim 14, wherein the substrate is a microfabricated synthesis channel.

16. The method of claim 13, further comprising a light source to illuminate the surface of said substrate and a detection system to detect a signal from said surface.

17. The method of claim 13, further comprising an appropriately programmed computer for recording an identity of a nucleotide when said nucleotide is added to said primer or to a nucleotide previously added to the primer.

18. A method of analyzing sequence of a target polynucleotide, comprising:
   (a) providing a primed target polynucleotide comprising a substantially complementary fluorescently labeled primer and a target polynucleotide, the primed target polynucleotide being immobilized to a substrate comprising a coated surface, wherein the target polynucleotide is randomly attached to the surface with single molecule resolution;
   (b) adding four types of nucleotides to the surface of the substrate under conditions whereby nucleotides are added to the primer dynamically, at least one type of nucleotide being fluorescently labeled; and
   (c) monitoring a time course of fluorescent signal from addition of at least one fluorescent nucleotide to the primer, thereby analyzing the sequence of the target polynucleotide, wherein if the primer label and the nucleotide label are the same, detecting and then bleaching the signal from the primer label prior to adding the four types of nucleotides.

19. The method of claim 18, wherein said monitoring step comprises taking images in the time course with total internal reflection fluorescence microscopy.

20. The method of claim 19, wherein the images are taken at a rate faster than the rate at which the fluorescently labeled nucleotide is added to the primer.

21. The method of claim 19, wherein fluorescence signal from addition of the fluorescently labeled nucleotide is detectable in the presence of fluorescent signal from unincorporated fluorescently labeled nucleotides.

22. The method of claim 18, wherein concentrations of the nucleotides are alternated by fluid exchange with a microfluidic device.

23. The method of claim 18, wherein the four types of nucleotides are each labeled with a different label.

24. The method of claim 18, wherein the surface is coated with a polyelectrolyte multilayer.

* * * * *